US 7,417,739 B2

(12) United States Patent
Doshoda et al.

(10) Patent No.: US 7,417,739 B2
(45) Date of Patent: Aug. 26, 2008

(54) SPECULAR GLOSS SIMULATION DEVICE, SPECULAR GLOSS SIMULATION METHOD, CONTROL PROGRAM FOR SPECULAR GLOSS SIMULATION DEVICE AND STORAGE MEDIUM THEREOF

(75) Inventors: Hiroshi Doshoda, Chiba (JP); Yoichi Miyake, Sakura (JP)

(73) Assignee: Sharp Kabushiki Kaisha, Osaka (JP)

( * ) Notice: Subject to any disclaimer, the term of this patent is extended or adjusted under 35 U.S.C. 154(b) by 358 days.

(21) Appl. No.: 11/259,166

(22) Filed: Oct. 27, 2005

(65) Prior Publication Data

US 2006/0092412 A1 May 4, 2006

(30) Foreign Application Priority Data

Oct. 29, 2004 (JP) ............................. 2004-316933
Jul. 20, 2005 (JP) ............................. 2005-210525

(51) Int. Cl.
*G01N 21/55* (2006.01)
(52) U.S. Cl. .................... 356/445; 356/425; 358/500
(58) Field of Classification Search ......... 356/445–448, 356/429–431, 238.1, 238.2, 600; 703/2, 703/5
See application file for complete search history.

(56) References Cited

U.S. PATENT DOCUMENTS 5,596,425 A * 1/1997 Usui et al. .................. 358/500

FOREIGN PATENT DOCUMENTS

| JP | 4-20846 A | 1/1992 |
| JP | 2003-329586 A | 11/2003 |
| JP | 2004-317131 A | 11/2004 |

OTHER PUBLICATIONS

Object Shape and Reflectance Modeling from Observation, International Conference on Computer Graphics and Interactive Techniques, Proceedings of the 24th annual conference on Computer graphics and interactive techniques, pp. 379-387, Year of Publication: 1997, ISBN:0-89791-896-7, Yoichi Sato, Mark D. Wheeler, and Katsushi Ikeuchi.*

(Continued)

*Primary Examiner*—Tarifur R Chowdhury
*Assistant Examiner*—Jonathon D Cook
(74) *Attorney, Agent, or Firm*—Birch, Stewart, Kolasch & Birch, LLP

(57) ABSTRACT

The present invention realizes a specular gloss simulation device which can accurately simulate specular glossiness of an image even if the image has a low density and low glossiness by measuring, in a given geometry, luminance of a sample having a base material and a colorant material layer formed on the base material and then simulating a specular reflection light amount in an other geometry from the measured luminance. A specular gloss simulation device is provided with a lower layer reflection light component calculating section for calculating a lower layer reflection light component, an internal reflection light component creating section for creating an internal reflection light component, a surface reflection light component creating section for creating a surface reflection light component, and a specular reflection light amount calculating section for obtaining a specular reflection light amount of the sample by adding up the components thus created by each section.

18 Claims, 23 Drawing Sheets

OTHER PUBLICATIONS

Steven A. Shafer, "Using color to separate Reflection Componenets" Color Research and apllication, pp. 210-218, vol. 10, No. 4 Winter 1985, © 1985 by John Wiley & Sons, Inc.

Gregory J. Ward, "Measuring and Modeling Anisotropic Reflection", Computer Graphics vol. 26, No. 2, Jul. 2, 1992, pp. 265-272, SIGGRAPH '92 Chicago, Jul. 26-31, 1992.

W. Newman, "Illumination for Computer Generated Pictures", Communications of the ACM, vol. 18, No. 6, pp. 311-317, Jun. 1975 © 1975, Accociation for Computing Machinery, Inc.

Michael Oren and Shree K. Nayer "Generalization of the Lambertain Model ans Implications for Machine Vision", International Journal of Cmputer Vision, vol. 14, pp. 227-251, 1995. © 1995 Kluwer Academic Publishers, Boston.

K.E. Torrance and E.M.Sparrow "Theory for Off-Specular Reflection From Roughened Surfaces", Journal of the optical society of America, vol. 57, No. 9, pp. 1105-1114, 1967.

\* cited by examiner

INCIDENT LIGHT ANGLE  REFLECTION LIGHT ANGLE

FIG. 26

UPPER LAYER DATA INPUT

| REFRACTIVE INDEX OF UPPER LAYER MATERIAL | R20 |
| TRANSMITTANCE OF UPPER LAYER MATERIAL | R21 |
| ROUGHNESS OF SURFACE | R22 |
| EVENNESS IN DENSITY | R23 |

LOWER LAYER SAMPLE SET

OK (R24)   CANCEL (R25)

FIG. 27

GEOMETRY DESIGNATION FOR FITTING PROCESS

|  | INCIDENT LIGHT ANGLE | REFLECTION LIGHT ANGLE |
|---|---|---|
| FIRST NON-SPECULAR REFLECTION GEOMETRY | R30 | R31 |
| SECOND NON-SPECULAR REFLECTION GEOMETRY | R37 | R38 |
| SPECULAR REFLECTION GEOMETRY | R32 | R33 |

OK (R34)   CANCEL (R35)   BACK (R36)

SPECULAR GLOSS SIMULATION DEVICE, SPECULAR GLOSS SIMULATION METHOD, CONTROL PROGRAM FOR SPECULAR GLOSS SIMULATION DEVICE AND STORAGE MEDIUM THEREOF

This Nonprovisional application claims priority under 35 U.S.C. § 119(a) on Patent Applications Nos. 316933/2004 and 210525/2005 filed in Japan respectively on Oct. 29, 2004, and Jul. 20, 2005, the entire contents of which are hereby incorporated by reference.

FIELD OF THE INVENTION

The present invention relates to a specular gloss simulation device, a specular gloss simulation method, a control program for the specular gloss simulation device and storage medium thereof. The specular gloss simulation method is for simulating a specular gloss of an image formed by a printing method such as an electrophotographic printing method, an inkjet printing method, an offset printing method, or a letterpress printing method.

BACKGROUND OF THE INVENTION

Gloss is one quality evaluation item of an image sample produced by various techniques. In general, the gloss depends largely upon geometry (that is a positional relationship of a light source, a sample (hereinafter, the image sample is denoted simply as sample) and a light receiver) under which observation is carried out. The larger a zenith angle 1 in a light source incidence direction (in which the light comes from the light source) and a zenith angle 2 in a light reflection direction (in which the light goes to the light receiver) as illustrated in FIG. 2, the stronger the gloss that a person feels. In order to evaluate this gloss quantitatively as glossiness, presently a glossimeter adopts some limited kinds of arrangements (JIS Z 8741) such as a combination of a zenith angle 45° in the direction, in which the light enters toward a sample 3 and a zenith angle 60° in the light reflection direction. This arrangement is standardized in, for example JIS (Japanese Industrial Standards), and the like.

However, this technique gives glossiness that can be merely a kind of standardized measure, but can not provide quantitative data enough for evaluating a property of deviation reflection. In order to solve this problem, a gonio-spectro photometer system (gonio-photo spectrometer) and the like, which is generally used in painting industry, is used. This makes it possible to obtain quantitative data of the property of deviation reflection. However, the quantitative measurement using this gonio-spectro photometer system of an angle of deviation takes very long to obtain the measurement and can handle only limited varieties of shapes of a sample. Accordingly, this measurement is not so suitable for practical use.

In recent years, in a field of remote sensing, BRDF (Bidirectional Reflectance Distribution Function) is draws attention. This is devised based on Shafter's Dichromatic Reflection Model (refer to Document 1). In the Dichromatic Reflection Model, as illustrated in FIG. 3, reflection light from a surface of an object is made of two components called (i) a surface reflection (light component reflected on a surface) 4 and (ii) an internal reflection (light component reflected inside) 5. The surface reflection 4 is a light beam reflected on a surface of the sample 3 due to a difference in refractive indexes of the sample 3 and the air and has color of a light source 6. The light that enters inside the sample 3 is repeatedly refracted, absorbed, and scattered among dye particles 3A, whereby the light is absorbed into the dye particles 3A depending on the wavelength. Accordingly, the internal reflection light 5, which is a reflection from the sample 3, has a color of the sample 3. Various proposed models of the BRDF are used according to respective purposes.

Document 2 discloses a method for evaluating a property of deviation inside reflection. This method simulates an amount of specular reflection light, by using BRDF. With this method, it is also possible to simulate glossiness in geometry other than existing geometry.

However, in the above method, the amount of the specular reflection light received by a glossimeter is examined only by the surface reflection in the Dichromatic Reflection Model and the specular glossiness is calculated by the BRDF. In an image made of a concentrated colorant material and thus producing high gloss, it is possible to ignore the internal reflection light component in the Dichromatic Reflection Model and a reflection light component from a base material positioned under a colorant material layer. However, in a case of an image whose color density from a colorant material is low, the reflection light component of an lower layer cannot be ignored. Moreover, in case of a low gloss image, the internal reflection light component cannot be ignored. Therefore, a correct value cannot be calculated with the above method.

(Document 1)

COLOR Research and application, Vol. 10, No. 4, pp. 210-218, 1985

(Document 2)

Japanese Unexamined Patent Publication 2003-329586 (published on Nov. 19, 2003)

SUMMARY OF THE INVENTION

The present invention is accomplished in view of the aforementioned problems, and an object of the present invention is to realize a specular gloss simulation device and a specular gloss simulation method which can accurately simulate, by using a Bidirectional Reflectance Distribution Function model, specular glossiness of an image even if the image has a low density or low glossiness.

In order to attain the object, a specular gloss simulation device according to the present invention for simulating specular gloss by measuring, in a given geometry, luminance of a sample that has a base material and a colorant material layer formed on the base material, and then simulating a specular reflection light amount in an other geometry from the thus measured luminance, is provided with: a lower layer reflection light component creating section for calculating a lower layer reflection light component from base material luminance, where the base material luminance is luminance of only the base material measured in a plurality of geometries, and the lower layer reflection light component is a component being reflected on the base material and transmitting through and out of the colorant material layer; an internal reflection light component creating section for measuring luminance of the sample in the given geometry, and for creating an internal reflection light component from the measured luminance and the lower layer reflection light component, where the internal reflection light component is a component being reflected from an interior of the colorant material layer; a surface reflection light component creating section for measuring luminance of the sample in the given geometry, and for creating a surface reflection light component from the measured luminance, the lower layer reflection light component, and the internal reflection light component, where the surface reflection light component is a component being reflected on a surface of the colorant material layer; and a specular reflection light amount calculating section for obtaining a specular reflection light amount of the sample from the components thus created by the lower layer reflection light component creating section, internal reflection light component creating section, and surface reflection light component creating section.

Moreover, in order to attain the object, another specular gloss simulation device according to the present invention for simulating specular gloss by measuring, in a given geometry, luminance of a sample that has a base material and a colorant material layer formed on the base material, and then simulating a specular reflection light amount in an other geometry from the thus measured luminance, is provided with: a lower layer reflection light component creating section for calculating a lower layer reflection light component from base material luminance, where the base material luminance is luminance of only the base material measured in a plurality of geometries, and the lower layer reflection light component is a component being reflected on the base material and transmitting through and out of the colorant material layer; an internal reflection light component creating section for creating an internal reflection light component from luminance of the sample and the lower layer reflection light component, where the internal reflection light component is a component being reflected from an interior of the colorant material layer, and the luminance of the sample is measured in the given geometry; a surface reflection light component creating section for creating a surface reflection light component from the luminance of the sample, the lower layer reflection light component, and the internal reflection light component, where the surface reflection light component is a component being reflected on a surface of the colorant material layer, and the luminance of the sample is measured in the given geometry; and a specular reflection light amount calculating section for obtaining a specular reflection light amount of the sample from the components thus created by the lower layer reflection light component creating section, internal reflection light component creating section, and surface reflection light component creating section.

With the above arrangement, the simulation of the specular gloss is carried out by obtaining the specular reflection light amount of the sample by more effectively using the Bidirectional Reflectance Distribution Function model, taking the lower layer reflection light component and the internal reflection light component, as well as the surface reflection light component, into consideration. This makes it possible to calculate out the specular gloss with high accuracy for low-density image sample and low-gloss image sample for which accurate calculation of the specular gloss cannot be done with the conventional art.

In order to attain the object, still another specular gloss simulation device according to the present invention for simulating specular gloss by measuring, in a given geometry, luminance of a sample that has a base material and a colorant material layer which is formed on the base material and contains colorant material particles, and then simulating a specular reflection light amount in an other geometry from the thus measured luminance, is provided with: a lower layer reflection light component creating section for calculating lower layer reflection light components in the given geometry and the other geometry from base material luminance, where the base material luminance is luminance of only the base material measured in a plurality of geometries, and the lower layer reflection light component is a component being reflected on the base material and transmitting through and out of the colorant material layer; an upper layer reflection light component creating section for calculating a diffuse reflection light component, a colorant material particle reflection light component, and a surface reflection light component in the other geometry from the luminance of the sample measured in the given geometry and the lower layer reflection light component in the given geometry, the lower layer reflection light component being calculated out by the lower layer reflection light component creating section, where the diffuse reflection light component is a component being diffused among the colorant material particles contained in the colorant material layer and transmitting out of the colorant material layer, the colorant material particle reflection light component is a component being reflected on the colorant material particles, and the surface reflection light component is a component being reflected on a surface of the colorant material layer; and a specular reflection light amount calculating section for calculating out a specular reflection light amount of the sample in the other geometry from the components in the other geometry which are thus calculated out by the lower layer reflection light component creating section and the upper layer reflection light component creating section. With the above arrangement, the simulation of the specular gloss is carried out by obtaining the specular reflection light amount of the sample by effectively using the Bidirectional Reflectance Distribution Function model, taking the lower layer reflection light component of the base material and the diffuse reflection light component and colorant material particle reflection light component of the colorant material layer, as well as the surface reflection light component of the colorant material layer, into consideration. This makes it possible to calculate out the specular gloss with high accuracy for low-density image sample and low-gloss image sample for which accurate calculation of the specular gloss cannot be done with the conventional art.

In order to attain the object, a specular gloss simulation method according to the present invention for simulating specular gloss by simulating a specular reflection light amount of a sample having a base material and a colorant material layer formed on the base material, is arranged to include: (i) creating a lower layer reflection light component by calculating out the lower layer reflection light component from base material luminance where the base material luminance is luminance of only the base material measured in a plurality of geometries which are varied in incident light angle and reflection light angle by a constant angle, the lower layer reflection light component is a component being reflected on the base material and transmitting through and out of the colorant material layer; (ii) creating an internal refection light component by simulating, by using a Bidirectional Reflectance Distribution Function model, the internal refection light component in the other geometry from an internal reflection light component calculated out from luminance of the sample measured in one non-specular reflection geometry and the lower layer reflection light component, where the internal reflection light component is a component being reflected from an interior of the colorant material layer; (iii) creating a surface reflection light component by simulating, by using a Bidirectional Reflectance Distribution Function model, the surface reflection light component in the other geometry from a surface reflection light component calculated out from luminance of the sample measured in one non-specular reflection geometry, the lower layer reflection light component, and the internal reflection light component, where the surface reflection light component is a component being reflected on a surface of the colorant material layer; and (iv) calculating out a specular reflection light amount of the sample from the lower layer reflection light component, internal reflection light component, and surface reflection light component thus obtained.

The specular gloss simulation device of the present invention is used for simulating, by using the Bidirectional Reflectance Distribution Function model, a specular reflection light amount of a sample in each geometry, the sample having, as a sample image, the colorant material layer on the base material, where the base material may be paper, an OHP film or the like, and the colorant material layer contains toner, pigment ink, dye ink or the like. From the thus simulated specular reflection light amount, the specular gloss of the sample is simulated in the method according to the present invention.

With the above arrangement, the simulation of the specular gloss is carried out by obtaining the specular reflection light amount of the sample by effectively using the Bidirectional Reflectance Distribution Function model, taking the lower layer reflection light component and the internal reflection light component, as well as the surface reflection light component, into consideration. This makes it possible to calculate out the specular gloss with high accuracy for low-density image sample and low-gloss image sample for which accurate calculation of the specular gloss cannot be done with the conventional art.

In order to attain the object, a specular gloss simulation method according to the present invention for simulating specular gloss by simulating a specular reflection light amount of a sample having a base material and a colorant material layer which is formed on the base material and contains colorant material particles, is arranged to include: (i) creating lower layer reflection light components in the given geometry and the other geometry by calculating out the lower layer reflection light components from base material luminance where the base material luminance is luminance of only the base material measured in a plurality of geometries, the lower layer reflection light component is a component being reflected on the base material and transmitting through and out of the colorant material layer; (ii) calculating out a diffuse reflection light component, a colorant material particle reflection light component, and a surface reflection light component from the luminance of the sample measured in the given geometry and the lower layer reflection light component in the given geometry, the lower layer reflection light component being calculated out in the step (i), where the diffuse reflection light component is a component being diffused among the colorant material particles contained in the colorant material layer and transmitting out of the colorant material layer, the colorant material particle reflection light component is a component being reflected on the colorant material particles, and the surface reflection light component is a component being reflected on a surface of the colorant material layer; and (iii) calculating out a specular reflection light amount of the sample in the other geometry from the diffuse reflection light component, the lower layer reflection light component in the other geometry, which is thus calculated in the step (i) and the colorant material particle reflection light component, and the surface reflection light component thus calculated in the step (ii).

With the above arrangement, the simulation of the specular gloss is carried out by obtaining the specular reflection light amount of the sample by effectively using the Bidirectional Reflectance Distribution Function model, taking the lower layer reflection light component of the base material and the diffuse reflection light component and colorant material particle reflection light component of the colorant material layer, as well as the surface reflection light component of the colo-rant material layer, into consideration. This makes it possible to calculate out the specular gloss with high accuracy for low-density image sample and low-gloss image sample for which accurate calculation of the specular gloss cannot be done with the conventional art.

For a fuller understanding of the nature and advantages of the invention, reference should be made to the ensuing detailed description taken in conjunction with the accompanying drawings.

BRIEF DESCRIPTION OF THE DRAWINGS

FIG. 20(b) is a graph illustrating a result of an example 2 (specular glossiness simulation by using a toner sample having low concentration).

FIG. 26 is a diagram schematically illustrating an example of a data input screen displayed on a display section of the specular glossiness simulation device as illustrated in FIG. 25.

FIG. 27 is a diagram schematically illustrating another example of a data input screen displayed on a display section of the specular glossiness simulation device as illustrated in FIG. 25.

DESCRIPTION OF THE EMBODIMENTS

First Embodiment

Referring to FIG. 1 through FIG. 12, the following will describe one embodiment of the present invention. In the present embodiment, a specular gloss simulation device is described in which specular gloss is simulated by measuring luminance of a sample in a given geometry (having predetermined incident light angle and reflection light angle, and then a specular reflection light amount is simulated in a different geometry from the thus measured luminance, the sample including paper (base material) and a toner image (colorant material layer) formed on the paper according to an electrophotographic method. In the present embodiment, one of the specular reflection geometries and one of the non-specular reflection geometries are selected as the given geometries, and gonio data of these given geometries are measured.

First, the specular gloss simulation device of the present embodiment is described in regard to the dichromatic reflection (BRDF) model theory for the simulation of specular gloss of a sample. Here, description of the BRDF model will be given through the case where it is used to calculate reflection light components of the sample having the bilayer structure in which a colorant material layer is formed on a base material.

Figure 4:
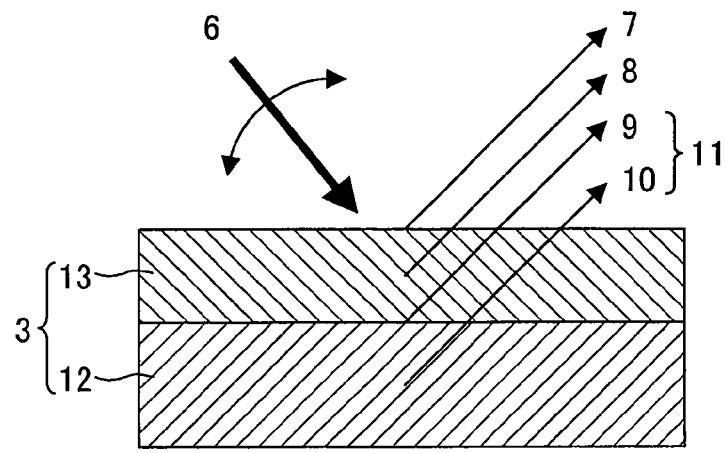
FIG. 4 is a diagram schematically illustrating a method of dividing reflection light components of a sample having a structure with two layers, according to the embodiment 1.

FIG. 4 schematically illustrates how the reflection light components of the bilayer sample are split into individual components. As illustrated in FIG. 4, a sample 3 includes an upper layer portion 13 made of a toner image (colorant material layer), and a lower layer portion 12 made of a base material such as paper or a transparent film. According to the dichromatic reflection (BRDF) model theory, the reflection light components of the light from a light source 6 include a surface reflection light component (Lrs) 7 and an internal reflection light component (Lri) 8, both from the upper layer portion 13, and a surface reflection light component 9 and an internal reflection light component 10, both from the lower layer portion 12. The composite light of these components becomes the reflected light from the sample 3. In order to calculate the reflected light components 7 through 10 according to the BRDF model, more than one unmeasurable parameter needs to be estimated.

However, since the measurement of the internal reflection light component 10 reflected from the lower layer portion 12 is difficult, the present invention combines the internal reflection light component 10 with the surface reflection light component 9 also from the lower layer portion 12, and uses the sum of these reflection light components as a lower layer reflection light component (Lru) 11. By calculating the lower layer reflection light component 11 based on measurement data obtained only from the lower layer portion 12, a specular reflection light amount can be accurately calculated for a wide variety of samples images according to the BRDF model. By thus calculating the lower layer reflection light component 11 with the surface reflection light component 7 and internal reflection light component 8 from the upper layer portion 13, an accurate specular reflection light amount can be obtained.

As the mathematical models effective for calculating the respective reflection light components, the present invention can use the following BRDF models (1) through (4).

(1) Ward Model

Reference: Ward G. J., Measuring and modeling anisotropic reflection, Computer Graphics Vol. 26, No. 2, pp. 265-272, 1992.

(2) Phong Model

Reference: B. Phong, Illumination for computer-generated pictures, Communications of the ACM, Vol. 18, No. 6, pp. 311-317, 1975.

(3) Oren-Nayar Model

Reference: Michael Oren and Shree K. Nayar, Generalization of the Lambertian Model and Implications for Machine Vision, International Journal of Computer Vision, Vol. 14, pp. 227-251, 1995.

(4) Torrance-Sparrow Model

Reference: K. E. Torrance and E. M. Sparrow, Theory for Off-Specular Reflection From Roughened Surfaces, J. Opt. Soc. Am. Vol. 57, No. 9, pp. 1105-1114, 1967.

Of these mathematical models, the Ward model and the Phong model have been proposed based on isotropic scattering of light, whereas the Oren-Nayar model and the Torrance- Sparrow model are based on non-isotropic scattering of light. In the present embodiment, the Torrance-Sparrow model is adopted as the mathematical model for calculating the surface reflection light component 7, and the Oren-Nayar model is adopted as the mathematical model for calculating the internal reflection light component 8. This is because more accurate values can be obtained when non-isotropic scattering of light is taken into consideration, though it involves complex equations.

Figure 5:
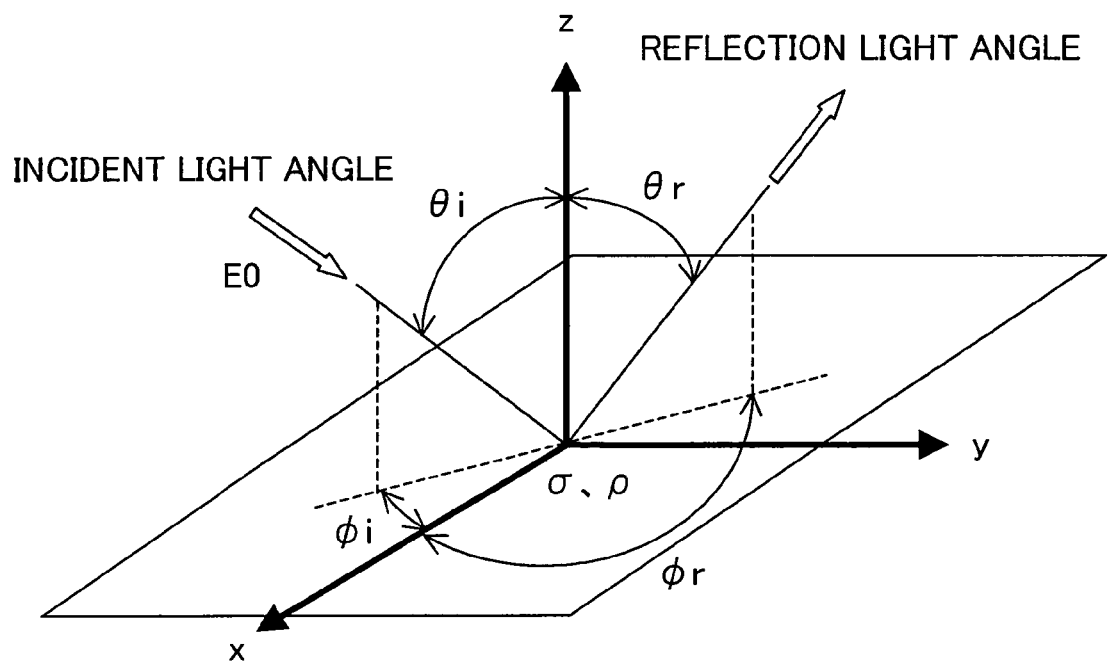
FIG. 5 is a diagram schematically illustrating a geometric arrangement in a BRDF model.
Figure 6:
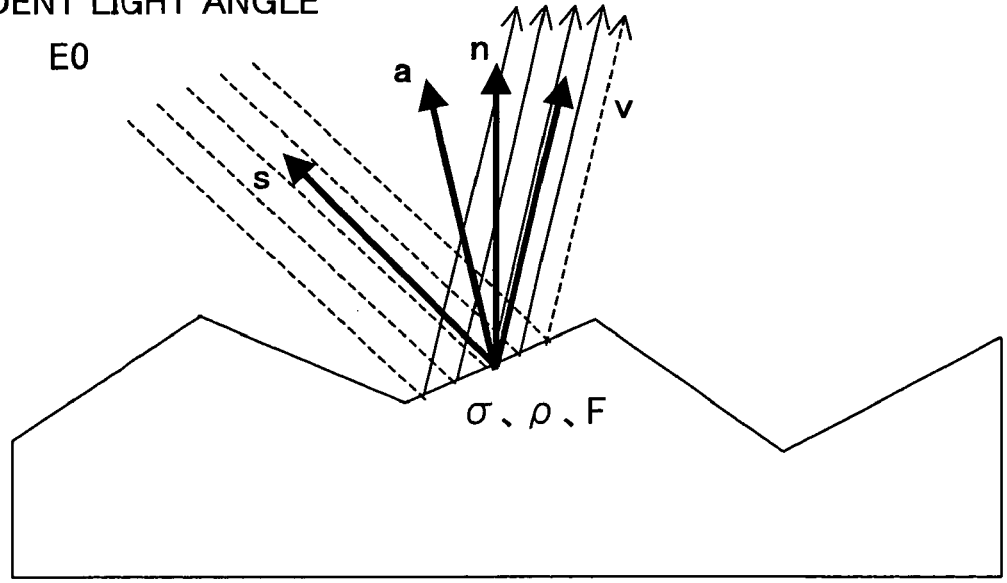
FIG. 6 is a diagram schematically illustrating a geometric definition of a surface of a material in the BRDF model.

FIG. 5 represents a geometric arrangement according to the BRDF model. FIG. 6 represents geometric definitions of object surfaces according to the BRDF model. While FIG. 2 only represents a specular reflection geometry (θi=θr, øi+ør=180° in FIG. 5), FIG. 5 represents a three dimensional multi-angle geometry with the xyz axes (common geometry including the specular reflection geometry). FIG. 6 represents an approximation model that has been proposed for sample surfaces in the modeling of non-isotropic scattering of light according to the Oren-Nayar model and the Torrance-Sparrow model. It is assumed here that the sample has a non-planer surfaces with microscopic irregularities (roughness) made up with facets. Here, steric effect and steric hindrance due to an aggregation of such facets are taken into consideration when the reflection luminance is expressed.

In calculating the internal reflection light component Lri using the Oren-Nayar model, mathematical value LrON is calculated first according to Equation (1) below.

$$LrON = \frac{\sigma}{\pi} E0\cos\theta i [C1(\sigma) + \cos(\phi r - \phi i)C2(\alpha; \beta; \phi r - \phi i; \sigma)\tan\beta) + \quad (1)$$

$$(1 - |\cos(\phi r - \phi i)|)C3(\alpha; \beta; \sigma)\tan\left(\frac{\alpha + \beta}{2}\right) +$$

$$0.17\frac{\rho^2}{\pi} E0\cos\theta i \frac{\sigma^2}{\sigma^2 + 0.13}\left[1 - \cos(\phi r - \phi i)\left(\frac{2\beta}{\pi}\right)^2\right]$$

$$C1 = 1 - 0.5\frac{\sigma^2}{\sigma^2 + 0.33}$$

$$C2 = \begin{cases} 0.45\frac{\sigma^2}{\sigma^2 + 0.09}\sin\alpha & \text{(if } \cos(\phi r - \phi i) \geq 0\text{)} \\ 0.45\frac{\sigma^2}{\sigma^2 + 0.09}\sin\alpha & \left(\sin\alpha - \left(\frac{2\beta}{\pi}\right)^3\right) \text{ (if not)} \end{cases}$$

$$C3 = 0.125\left(\frac{\sigma^2}{\sigma^2 + 0.09}\right)\left(\frac{4\alpha\beta}{\pi^2}\right)^2$$

In Equation (1), θi is the zenith angle in the light source direction, øi is the azimuth angle in the light source direction, θr is the zenith angle in the light reflection direction, ør is the azimuth angle in the light reflection direction, σ is the roughness variable of the surface profile, E0 is the radiant luminance incident on the sample, ρ is the refractive index of the microscopic surface of the sample surface, α=max [θr, θi], and β=min [θr, θi] (see FIG. 5, FIG. 6).

In calculating the surface reflection light component Lrs according to the Torrance-Sparrow model, mathematical value LrTS is calculated first according to Equation (2) below.

$$LrTS = E0\frac{FGAF}{\cos\theta r \cos\theta a}ce^{-\frac{\theta a^2}{2\sigma^2}} \quad (2)$$

$$GAF = \max\left[0, \text{Min}\left[1, \frac{2<s,n><a,n>}{<s,a>}, \frac{2<v,n><a,n>}{<v,a>}\right]\right]$$

$$c = \int_{\theta a=0}^{\frac{\pi}{2}} \int_{\phi a=0}^{2\pi} e^{-\frac{\theta a^2}{2\sigma^2}}\sin\theta a d\phi a d\theta a$$

In Equation (2), F is the Fresnel reflection index, n is the normal vector of the sample 3, s is the vector of the light source direction, v is the vector of the light reflection direction, a is the bisector vector of s and v, θr is the zenith angle of the light reflection direction, θa is the zenith angle of vector a, øa is the azimuth angle of vector a, σ is the roughness variable of the surface profile, and E0 is the radiant luminance incident on the sample. Further, in Equation (2), <x, y> (x, y are arbitrary numbers) is the inner products of the vectors (see FIG. 5, FIG. 6).

Now, referring to the flow chart in FIG. 8, a method will be described by which the amount of specular reflection light is calculated for each geometry from a measured value of luminance in a predetermined geometry using the above technique.

First, to calculate an lower layer reflection light component Lru, the transmittance of only the upper layer portion (toner image) 13 of a sample for which the specular reflection light component is to be calculated is calculated (step S1). The measurement geometry here includes a light source, a sample, and a light receiver positioned along a straight line. In such a geometry, the light source shines right above the sample. That light which is received by the light receiver located right under the sample is measured with a transmission density meter as light having transmitted the sample. Then, the transmission density Dt for only the upper layer portion 13 is obtained by calculating a differential between a sample with a toner image formed thereon (a sample made up of the upper layer portion 13 and the lower layer portion 12) and a sample made up of only the lower layer portion (paper) 12. A transmittance Tt for only the upper layer portion 13 (in other words, the toner image) is given by Tt=10^(−Dt).

Throughout the following steps, the refractive index (literature value) of resin which is a main component of toner is used as the refractive index of the upper layer portion (toner image) 13. With current measuring theory, it is impossible to measure the refractive index of a toner layer on paper. This is why the refractive index of the upper layer portion 13 is not measured, and the refractive index (literature value) of resin which is a main component of the toner is used instead, in the present embodiment. Actual measurement would yield a substantially identical value.

Next, a sample with no upper layer portion 13, that is, a sample with only the lower layer portion 12 (in the present embodiment, paper or transparent film still carrying no toner image formed thereon) is prepared. With the light source incidence direction and the light reflection direction of the sample with only the lower layer portion 12 being resolved at high resolution, gonio data is then measured (step S2). The "Gonio data" indicates angle dependence of the luminance of scattered light from a sample which is measured with a goniospectro photometer. Here, CIE 1976 L*a*b* (CIE: Commission International de l'Eclairage. L* is a lightness, and a* indicates redness-greenness and b* indicates yellowness-blueness) color space is used for the measurement. Therefore, the value of L* is employed as the gonio data.

Figure 7:
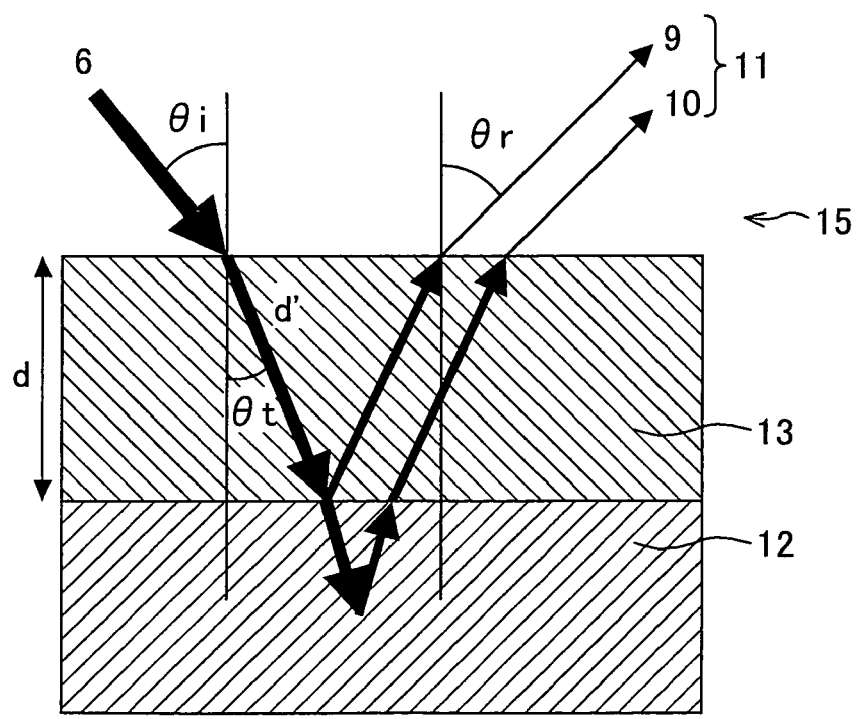
FIG. 7 is a diagram schematically illustrating a refraction phenomenon of light and attenuation of an amount of light, which are taken into consideration when an lower layer reflection light component is calculated in the embodiment 1.

The lower layer reflection light component Lru is calculated from this data (step S3). FIG. 7 is a diagram schematically illustrating a refraction phenomenon of light and attenuation of an amount of light, which are taken into consideration when the lower layer reflection light component Lru is calculated. Light incident to the sample at an incident light angle θi refracts at the interface between an air layer 15 and the upper layer portion 13. This refraction phenomenon obeys Fresnel's theory. The angle θt after the refraction is given by Fresnel's law (n1×sin θi=n2×sin θt, where n1 is the refractive index of a pre-incidence medium, and n2 the refractive index of a post-incidence medium). Light is attenuated at the interface due to the refraction as it passes through the toner layer. The Fresnel transmittance Tn of that light is given by equation (3):

$$Tn = \left[\left(\frac{n2\cos\theta t}{n1\cos\theta i}\right)\left(\frac{2n1\cos\theta i}{n2\cos\theta i + n1\cos\theta t}\right)^2 + \left(\frac{n2\cos\theta t}{n1\cos\theta i}\right)\left(\frac{2n1\cos\theta i}{n1\cos\theta i + n2\cos\theta t}\right)^2\right]/2 \quad (3)$$

As light passes through the upper layer portion 13, the light is attenuated by the upper layer portion 13 before reaching the lower layer portion 12. The attenuation obeys the Beer-Lambert law (−logT=a×d, where a is the absorption coefficient of a colorant material layer, d is the thickness of the colorant material layer, and T is the transmittance). The length of the optical path in the upper layer portion 13 traveled by the light before reaching the lower layer portion 12 changes with the incident light angle. The apparent transmittance Tt' in accordance with the changes in the length of the optical path is given by −logTt'=a×(d/cos θi). Light attenuation is evaluated in terms of the apparent transmittance.

From the above description, the amount of incident light reaching the lower layer portion 12 is calculated by evaluating the attenuation of the amount of light from the apparent transmittance Tt' in accordance with the Fresnel transmittance Tn and the changes in the length of the optical path. The calculation also takes into consideration the changes of the incident light angle of the light to the lower layer portion 12 caused by the refraction. A similar optical phenomenon occurs when the reflection from the lower layer portion 12 travels back to the air layer. Therefore, the lower layer reflection light component Lru is calculated by calculating from the gonio data of the sample with only the lower layer portion (paper) measured in S2 for all incident light angles and light reflection angles with the two refractions and an attenuation of light (see FIG. 7) taken into consideration. If the incident light angle θt after the refraction has decimal places, the angle is interpolated by proration from the preceding and succeeding angle values. There are no particular limitations on angle resolution in the process. Here, the resolution is 1° because the measuring device has a maximum angle resolution of 1°. To calculate the specular reflection light component more precisely, the angle resolution is preferably 1° or less.

As described in the foregoing, the incident direction of light to the upper layer portion is obtained from the refractive index. In addition, since the light is absorbed and attenuated by the upper layer portion, the degree of attenuation is evaluated from a transmittance. In other words, from the refractive indexes are calculated the optical path involving the refractions at the air layer and the upper layer portion and the subsequent incidence and the optical path involving the reflection from the lower layer portion (paper) and the further refractions at the upper layer portion and the air layer. The attenuation of the light is evaluated from the transmittance in accordance with these optical paths. This value is subjected to a computation (multiplied by the gonio data of the sample with only the lower layer portion (paper)) to obtain the lower layer reflection light component Lru.

Next, to calculate the internal reflection light component Lri, the luminance value Lra (L* of CIE 1976 L*a*b*) of the sample is measured in one certain geometry which contains almost zero surface reflection light component (step S4). This geometry is termed the non-specular reflection geometry. Generally, the more the geometry differs from specular reflection, the smaller the surface reflection light component. The non-specular reflection geometry selected here therefore preferably has a large light source incident light angle and includes a light source incidence position and a light receiving position in close proximity.

For the present embodiment, an exemplary geometry is selected where the light source incident light angle θi is 45° (φi=0°) and the light reflection angle θr is −60° (φr=0°). The lower layer reflection light component Lru calculated in the same geometry is subtracted from the luminance value Lra measured in the geometry. Further, the surface reflection light component Lrs is approximated to 0. The remaining reflection light component is designated the internal reflection light component Lri. The internal reflection light component Lri thus obtained is subjected to fitting using an Oren-Nayar model (step S5). Fitting here means that an unknown parameter is calculated, and the internal reflection light component is obtained for each geometry, so that the internal reflection light component calculated from the luminance value Lra measured in the selected non-specular reflection geometry can be represented with an Oren-Nayar model.

The roughness variable σ (see FIG. 5) indicating the roughness of the surface used in the above process is a parameter defining the range of the reflection light component in the physical model. The variable is virtually meaningless and therefore fixed (for example, at 1 or 0.5) in the present case. E0 (see FIG. 5) is irradiance incident to the sample. Here, since the measured value space is CIE 1976 L*a*b* space, and L* is employed, E0=100π. From these values, the reflectance ρ of a small plane on the sample surface is estimated. The reflectance ρ of the small plane on the sample surface is never negative in the physical model; only positive values are employed.

Inserting these numeric values to equation (1), the parameters required by the Oren-Nayar model are estimated. Thus, an Oren-Nayar model calculated value LrON is determined. The magnitude of the Oren-Nayar model calculated value LrON is also subjected to fitting by estimating the reflectance parameter ρ for the small plane on the sample surface. It is therefore possible to calculate the internal reflection light component Lri for each geometry without any particular scaling of the Oren-Nayar model calculated value LrON. That is, the calculated LrON corresponds to the internal reflection light component Lri (Lri=LrON).

Finally, to calculate the surface reflection light component Lrs, the luminance value Lrb in one specular reflection geometry is measured (step S6). The geometry is termed the specular reflection geometry. The specular reflection geometry selected here is such that the light source incident light angle is 45° (φi=0°), and the light reflection angle is 45° (φr=180°). Note that the present invention is not limited to these angles. The lower layer reflection light component Lru calculated in the same geometry and the internal reflection light component Lri are subtracted from the luminance value Lrb (L* of CIE 1976 L*a*b*) measured in this geometry. The remaining reflection light component is designated the surface reflection light component Lrs. The surface reflection light component Lrs thus obtained is subjected to fitting using a Torrance-Sparrow model (step S7). Fitting here means obtaining, by using a Torrance-Sparrow model, the surface reflection light component and the colorant material particle reflection light component in each specular reflection geometry from the surface reflection light component calculated from the luminance value Lrb measured in the selected specular reflection geometry and the colorant material particle reflection light component. The Torrance-Sparrow model involves no estimation parameters. Inputting request parameters determines a Torrance-Sparrow model calculated value LrTS.

However, the surface reflection light component Lrs (=Lrb) cannot be expressed by the Torrance-Sparrow model calculated value LrTS itself. The Torrance-Sparrow model calculated value LrTS needs be scaled. Accordingly, the value of a shape parameter k that satisfies Lrs=Lrb=k×LrTS is calculated, and the magnitude of the Torrance-Sparrow model calculated value LrTS capable of reproducing the surface reflection light component Lrs is regulated. In the process, F is set to 1 to obtain surface reflection in the specular reflection geometry. The surface reflection light component Lrs for each specular reflection geometry is calculated as described above.

With these steps, the lower layer reflection light component Lru, the internal reflection light component Lri, and the surface reflection light component Lrs are individually calculated. By adding these calculated values in the same specular reflection geometry, the specular reflection light component (amount of specular reflection light) Lr is obtained (step S8).

In the aforementioned specular gloss simulation method, S1 to S3 are lower layer reflection light component forming steps, S4 to S5 are internal reflection light component forming steps, S6 to S7 are surface reflection light component forming steps, and S8 is a specular reflection light amount calculating step.

Figure 1:
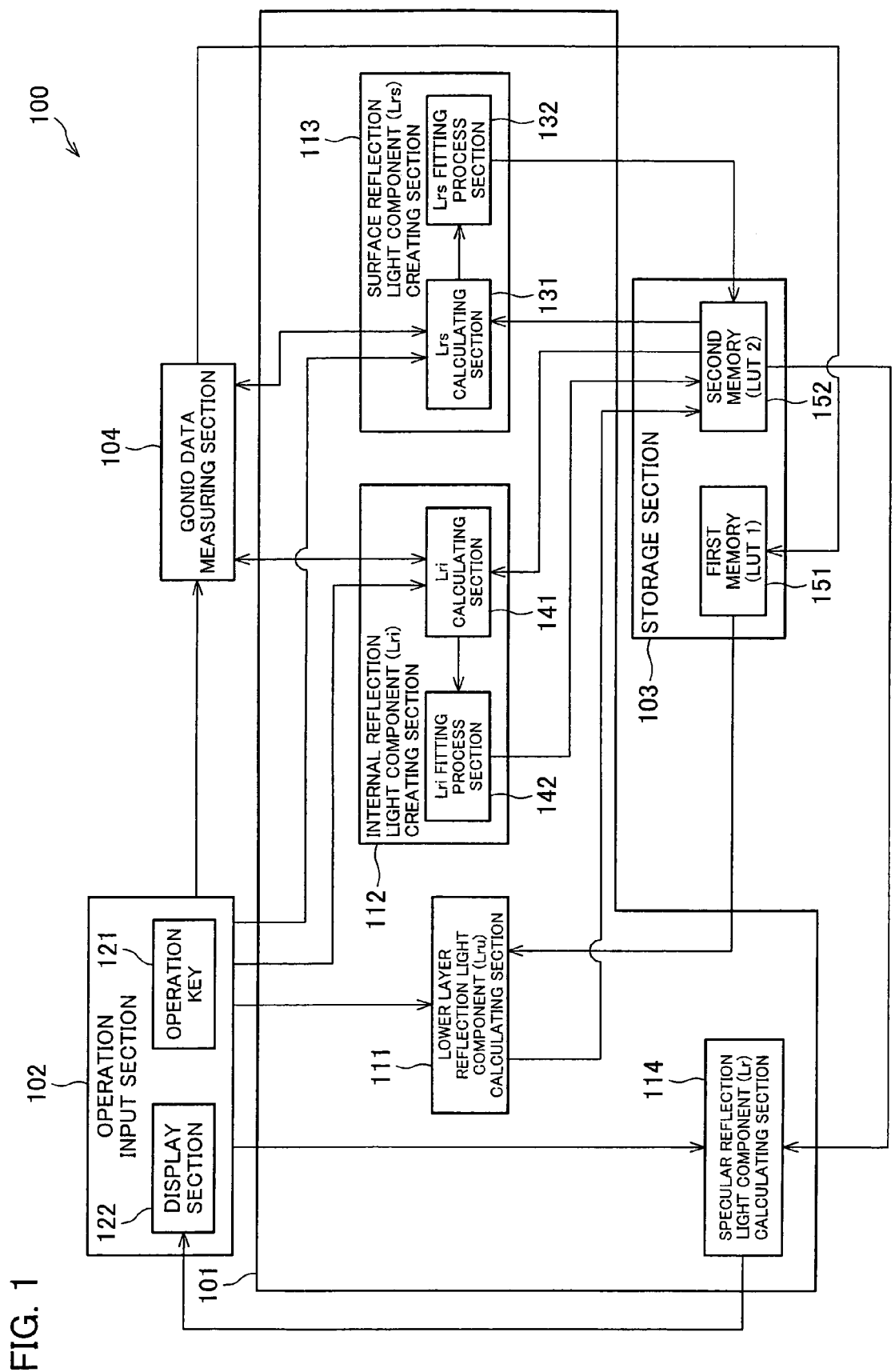
FIG. 1 is a block diagram of an arrangement of a specular gloss simulation device, according to an embodiment 1 of the present invention.
Figure 2:
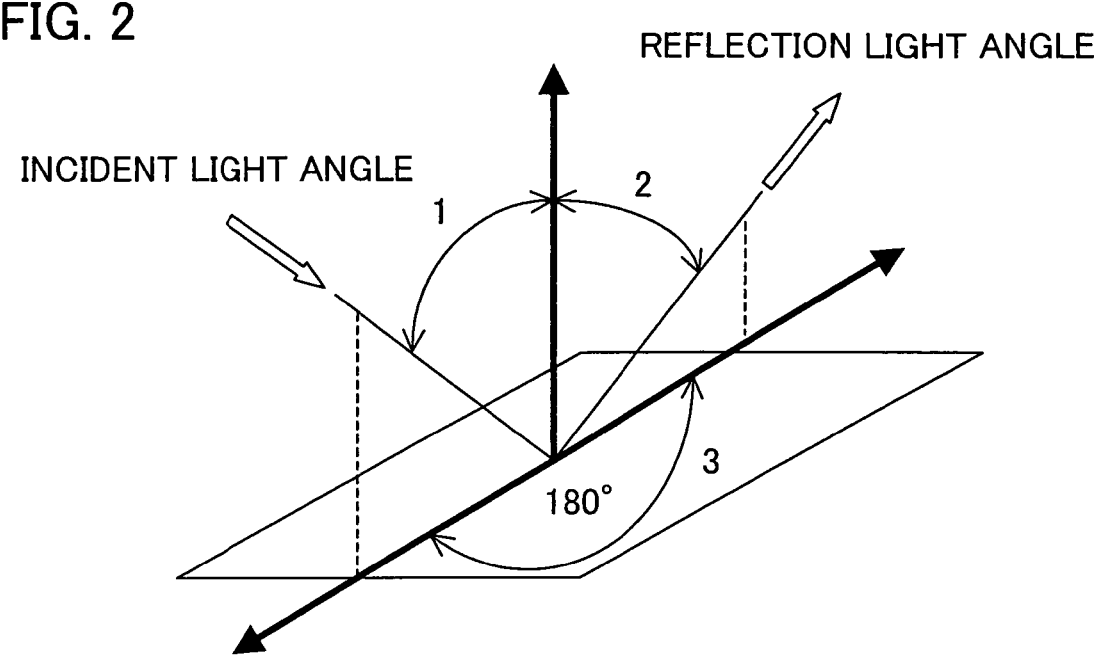
FIG. 2 is a diagram schematically illustrating specular reflection geometry.
Figure 3:
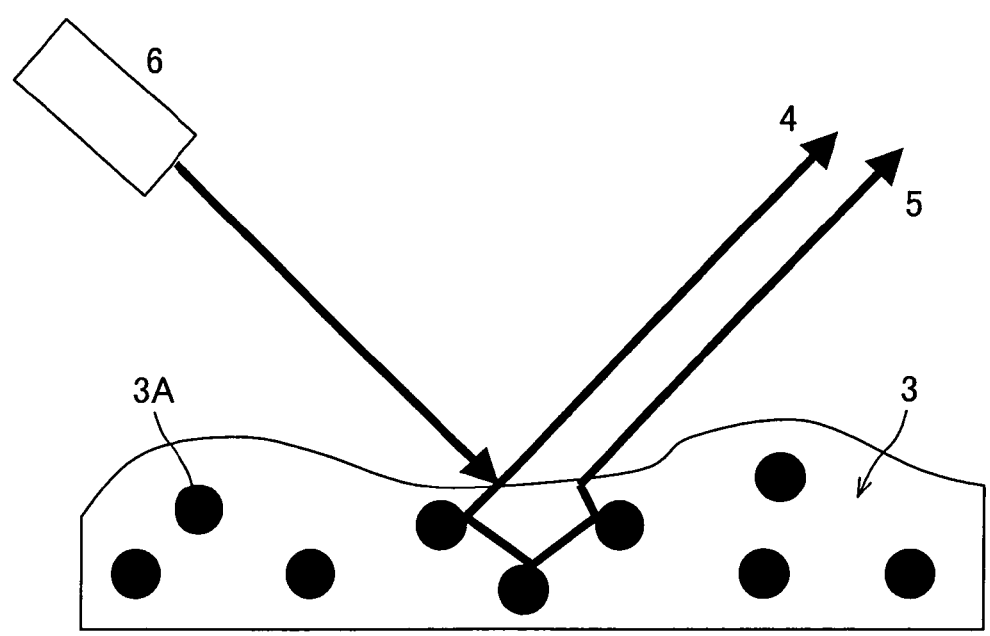
FIG. 3 is an explanatory diagram schematically illustrating a Dichromatic Reflection Model.

Next, an arrangement of a specular gloss simulation device according to the present invention is described below. The specular gloss simulation device according to the present embodiment calculates out the specular reflection light component of each specular reflection geometry by performing the process illustrated in the flowchart of FIG. 8. From the specular reflection light components thus obtained, the specular gloss simulation device simulates the specular gloss. In FIG. 1, an arrangement of a specular gloss simulation device 100 according to the present invention is illustrated.

As illustrated in FIG. 1, the specular gloss simulation device 100 is provided mainly with a calculating section 101, an operation input section 102, a storage 103, a gonio data measuring section 104. The calculating section 101 calculates out a specular reflection light component from (a) data of refractive index and transmittance (which has been inputted via the operation input section 102) of the upper layer portion (toner image) 13, (b) non-specular reflection geometry/specular reflection geometry being designated via the operation input section 102, and (c) gonio data being measured by the gonio data measuring section 104.

The calculating section 101 is provided with a lower layer reflection light component calculating section (lower layer reflection light component creating section) 111, an internal reflection light component creating section 112, a surface reflection light component creating section 113, and a specular reflection light component calculating section (specular reflection light amount calculating section) 114.

The lower layer reflection light component calculating section 111 is used for calculating a lower layer reflection light components (Lru) in each geometry.

The internal reflection light component creating section is used for calculating an internal reflection light component (Lri) from a measured gonio data in one non-specular reflection geometry, and performing fitting process to fit the thus calculated internal reflection light component (Lri) to the Oren-Nayar model thereby to obtain an internal reflection light component (Lri) in each geometry.

The surface reflection light component creating section 113 is used for calculating a surface reflection light component (Lrs) from a measured gonio data in one specular reflection geometry, and performing fitting process to fit the thus calculated surface reflection light component (Lrs) to the Torrance-Sparrow model thereby to obtain a surface reflection light component (Lrs) in each specular reflection geometry.

The specular reflection light component calculating section (specular reflection light amount calculating section) 114 is used for calculating a specular reflection light component (specular reflection light amount) (Lr) by adding up the lower layer reflection light component (Lru), internal reflection light component (Lri), and surface reflection light component (Lrs) thus obtained via the respective sections. The specular reflection light component calculating section 114 adds up the reflection light components of the same specular reflection geometry thereby to calculate out the specular reflection light component in each specular reflection geometry.

Moreover, the internal reflection light component creating section 112 is provided with an Lri calculating section 141 for calculating the internal reflection light component (Lri) from the measured gonio data in one non-specular reflection geometry, and an Lri fitting process section 142 for performing fitting process to fit the thus calculated internal reflection light component (Lri) to the Oren-Nayar model thereby to obtain the internal reflection light component in each geometry.

Moreover, the surface reflection light component creating section 113 is provided with an Lrs calculating section 131 for calculating the surface reflection light component (Lrs) from the measured gonio data in one specular reflection geometry, and an Lrs fitting process section 132 for performing fitting process to fit the thus calculated surface reflection light component (Lrs) to the Torrance-Sparrow mode thereby to obtain the surface reflection light component (Lrs) in each specular reflection geometry.

The operation input section 102 is used for inputting various numerical values necessary for the calculation of the specular reflection light component, and for displaying a result of calculation performed by the calculating section 101. The operation input section 102 includes operation keys 121 for inputting numerical values and/or the like, and a display section 122 for displaying items such as information inputted via the operation keys 121, the result of calculation, and/or the like.

The storage section 103 is used for storing therein a result of the measurement performed by the gonio data measuring section 104, and the result of the calculation performed by the calculating section 101. The storage section 103 is provided with a first memory 151 (LUT 1) and a second memory 152 (LUT 2). The first memory 151 is for storing therein gonio data of a sample measured by the deviation angle measuring section 104, the sample having a lower layer portion (paper) 12 only. The second memory 152 is for storing therein each reflection light component calculated out by the calculating section 101.

The gonio data measuring section 104 measures gonio data of the sample having the lower layer portion (paper) 12 only, and gonio data of a sample having a two-layered structure, that is, having the lower layer portion 12 and an upper layer portion (toner image) 13. The gonio data measuring section 104 has an angular resolution of 1°, by which the gonio data measuring section 104 is able to measure the gonio data per degree. For simulating the specular glossiness by using the specular gloss simulation device 100, the gonio data of the sample having the lower layer portion (paper) 12 only is measured per degree, meanwhile for the sample having the lower layer portion 12 and the upper layer portion 13, it is only required to measure the gonio data of one specular reflection geometry and one non-specular reflection geometry.

Next, how to simulate the specular gloss in each specular reflection geometry of a sample by using the specular gloss simulation device 100 is described below, referring to FIGS. 1 and 8.

Figure 8:
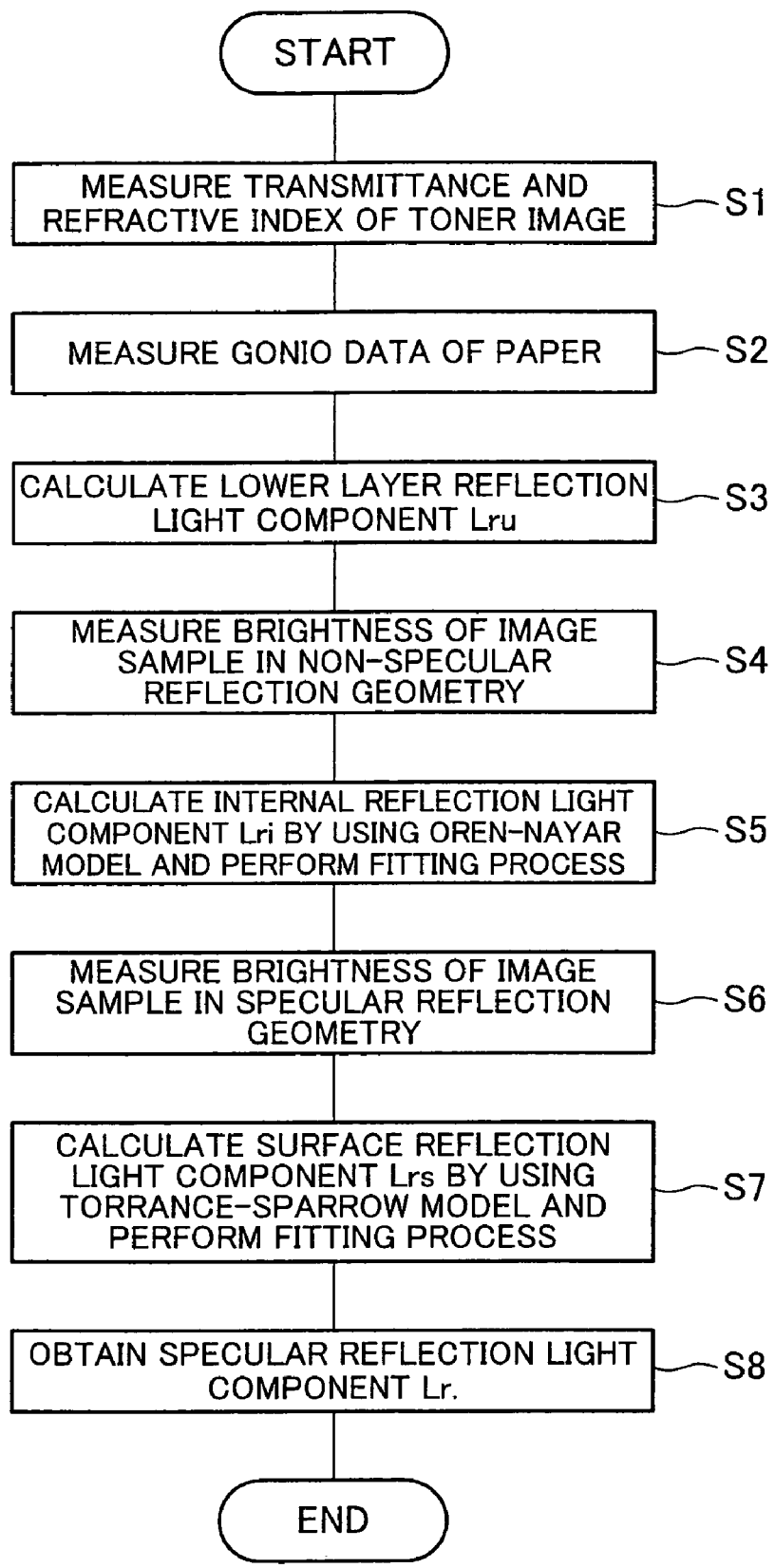
FIG. 8 is a flow chart of a process for calculating a specular reflection light component in each geometry from a measured value of luminance in a predetermined geometry in the embodiment 1.

Firstly, transmittance and refractive index of an upper layer portion of a sample (toner image) are measured (at S1 in FIG. 8). The transmittance and refractive index are to be inputted into the specular gloss simulation device 100 in order to measure the specular gloss component. Transmittance Tt is calculated out from Equation Tt=10^(−Dt), where Dt is a transmission density of only the upper layer portion. The transmission density is worked out by obtaining a difference between transmission density of the sample on which the toner image is formed (i.e., the sample having the lower layer portion 12 and the upper layer portion 13) and that of the sample having the lower layer portion (paper) 12 only. A transmission density meter is used to measure the transmission density of the sample on which the toner image is formed (i.e., the sample having the lower layer portion 12 and the upper layer portion 13) and that of the sample having the lower layer portion (paper) 12 only.

The measurement of the transmission density may be carried out with a X-rite model 820 transmission densitometer made by X-rite Inc.

In the following process a refractive index (literature value) of a resin which is a main component of the toner is used as the refractive index of the upper layer portion (toner image) 13.

Figure 9:
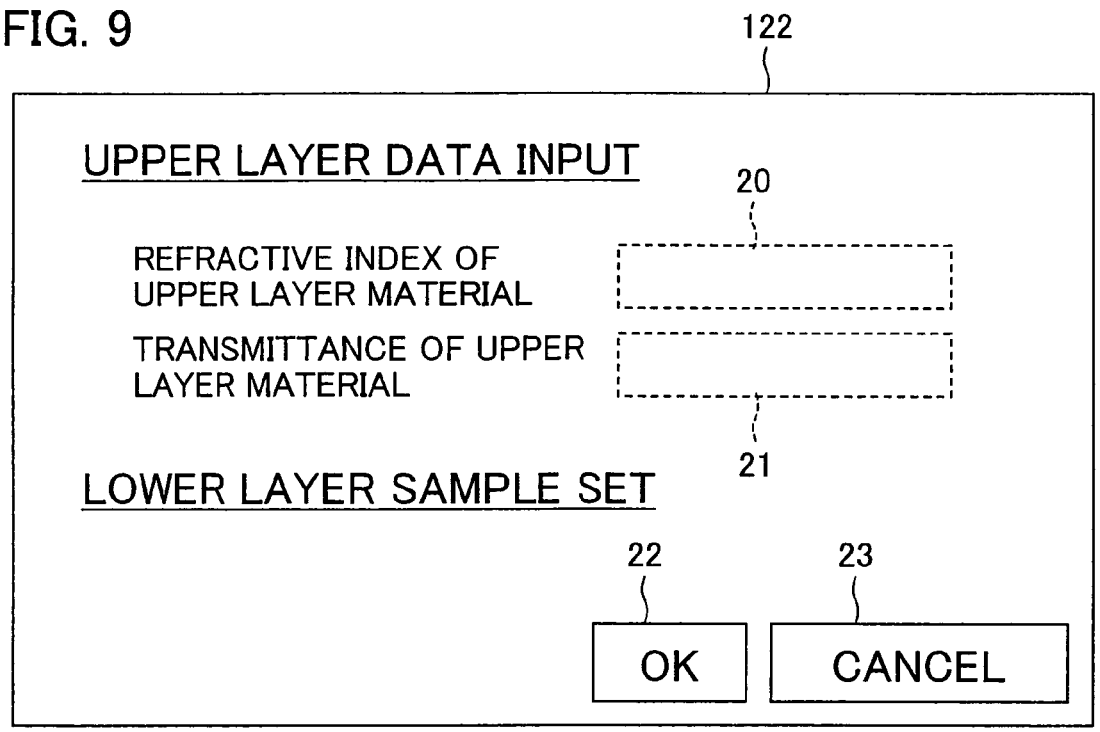
FIG. 9 is a diagram schematically illustrating an example of a data input screen displayed on a display section of the specular glossiness simulation device as illustrated in FIG. 1.

Next, the transmittance and the refractive index of the upper layer portion 13 of the sample thus measured by the above methods are inputted via the operation keys 121 of the operation input section 102. FIG. 9 illustrates an example of a data input screen displayed on the display section 122 of the specular gloss simulation device 100. On the data input screen illustrated in FIG. 9, an input item 20 for the refractive index of the sample to be measured and an input item 21 for transmittance of the sample to be measured are displayed. Further, an OK key 22, and a cancel key 23 are displayed on the data input screen illustrated in FIG. 9, which are touch-panel keys. Via the operation keys 121, the transmittance and the refractive index thus obtained by the above methods are inputted respectively into the input items 20 and 21 on the display section 122. If the cancel key 23 is pressed on this data input screen, a measurement mode is terminated with the data input screen inactivated.

Then, a base material made of the same material as that of the base material of the sample to be measured (i.e., the sample having only the lower layer portion) is put in the gonio data measuring section 104 of the specular gloss simulation device 100, then the OK key 22 is pressed. In this way, the gonio data measuring section 104 measures the gonio data (CIE 1976*a*b*L*) of the sample having only the lower layer portion (at S2 in FIG. 8). The gonio data thus measured is stored in the first memory 151 of the storage section 103.

As the gonio data measuring section 104, gonio-photo spectrometer GSP-2S (made by Murakami Shikisai) may be used, for example. Moreover, the gonio data measurement of the sample having only the lower layer portion has the angular resolution of 1° with respect to the light source incident light angle and reflection light angle. Therefore, the first memory 151 stores the gonio data in association with the incident light angle and the reflection light angle, the gonio data being measured at the incident light angle and the reflection light angle per degree.

Next, based on the refractive index theory and attenuation theory, the lower layer reflection light component calculating section 111 calculates the lower layer reflection light component (Lru) in each geometry from the refractive index and transmittance of the upper layer portion which are inputted via the operation input section 102, and the gonio data stored in the first memory 151 (at S3 in FIG. 8). The lower layer reflection light component (Lru) thus calculated is then stored in the second memory 152 in the storage section 103.

After that, a similar process is carried out for a given non-specular reflection geometry selected. Information on the non-specular reflection geometry is inputted via the operation input section 102, and then the gonio data in the non-specular reflection geometry is measured (at S4 in FIG. 8). From the gonio data thus measured, the internal reflection light component (Lri) of the non-specular reflection geometry is calculated out. Then, fitting process carried out in which the internal reflection light component (Lri) of the non-specular reflection geometry is applied in the Oren-Nayar model, thereby to obtain the internal reflection light component (Lri) in each geometry (at S5 in FIG. 8).

Further, a similar process is carried out for a given specular reflection geometry selected. Information on the specular reflection geometry is inputted via the operation input section 102, and then the gonio data in the specular reflection geometry (at S6 in FIG. 8). From the gonio data thus measured, the surface reflection light component (Lrs) of the specular reflection geometry is calculated out. Then, fitting process is carried out in which the surface reflection light component (Lrs) of the specular reflection geometry is fitted to the Torrance-Sparrow model, thereby to obtain the surface reflection light component (Lrs) in each specular reflection geometry (at S7 in FIG. 8).

Figure 10:
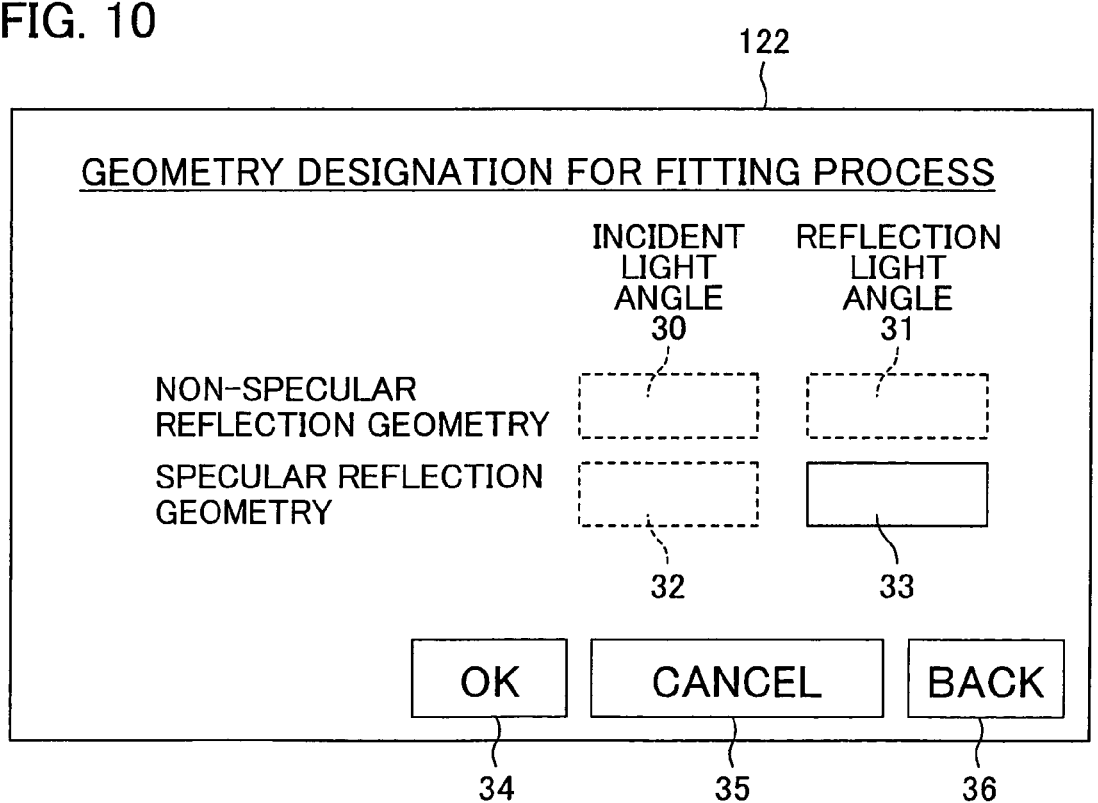
FIG. 10 is a diagram schematically illustrating another example of a data input screen displayed on a display section of the specular glossiness simulation device as illustrated in FIG. 1.

FIG. 10 gives an example of the data input screen displayed on the display section 122, for the input of the information regarding the selected non-specular reflection geometry and specular reflection geometry. The present invention is not limited to the arrangement exemplified here in which the information of the non-specular reflection geometry and specular reflection geometry are inputted on the same screen. The data input screen illustrated in FIG. 10 is provided with an input item 30 for the incident light angle of the non-specular reflection geometry, an input item 31 of the refection angle of the non-specular reflection geometry, an input item 32 for the incident light angle of the specular reflection geometry, and an input item 33 of the refection angle of the specular reflection geometry. Further, the data input screen illustrated in FIG. 10 is provided with an OK key 34, a cancel key 35, and a back key 36, which are touch-panel keys. When the cancel key 35 is pressed, the measurement mode is terminated with the data input screen inactivated. When the back key 36 is pressed, the display screen goes back to the data input screen illustrated in FIG. 9.

By the input items regarding the non-specular reflection geometry, the geometry for the fitting process for the internal reflection light component (Lri) is designated. By the input items regarding the specular reflection geometry, the geometry for the fitting process for the surface reflection light component (Lrs) is designated. The incident light angle and reflection light angle of the non-specular reflection geometry should be designated separately. However, the incident light angle and reflection light angle of the specular reflection geometry are identical, therefore, a value inputted in one of the input items (e.g., the input item 32 for the incident light angle) is also displayed in the other one of the input items (e.g., the input item 33 for the reflection light angle). That is, it is only required to input the value either one of the input items for the specular reflection geometry.

After the input of the information regarding the non-specular reflection geometry and specular reflection geometry, and the sample on which the toner image is formed is placed on the gonio data measuring section 104, the OK key 34 is pressed, so that the processes of S4 to S7 are carried out. Thereby, the lower layer reflection light component (Lru), internal reflection light component (Lri), surface reflection light component (Lrs) in each geometry is calculated out. These values are then stored in the second memory 152 in association with the geometries.

The following will describe, in a specific manner, how the internal reflection light components (Lri) of all geometries are calculated.

First, in a display section 122 that displays a data input screen shown in FIG. 10, the data of an incident light angle and a light reflection angle of the input non-specular reflection geometry is supplied to an Lri calculating section 141, and is then supplied to a gonio data measuring section 104. In the gonio data measuring section 104, gonio data (Lra) of the geometry thus input is measured and the data as a result of the measurement is supplied to the Lri calculating section 141.

In the Lri calculating section 141, the data of the lower layer reflection light component (Lru) calculated using the same geometry is selected and retrieved from the second memory 152, and the lower layer reflection light component (Lru) is subtracted from the gonio data (Lra). Furthermore, in this instance, the surface reflection light component (Lrs) is approximated to 0 and the remaining reflection light components are used as the internal reflection light component (Lri).

The data of the internal reflection light component (Lri) calculated by the Lri calculating section 141 is supplied to the Lri fitting process section 142. In the Lri fitting process section 142, the supplied internal reflection light component (Lri) is subjected to fitting with the Oren-Nayar model. With this, the internal reflection light component (Lri) of each geometry is figured out, and the data thus figured out is stored in the second memory 152.

The following will specifically describe how the surface reflection light components (Lrs) of all specular reflection geometries are calculated.

First, in the display section 122 that displays a data input screen shown in FIG. 10, the data of an incident light angle and a light reflection angle of the input specular reflection geometry is supplied to the Lrs calculating section 131, and is then supplied to the gonio data measuring section 104. In the gonio data measuring section 104, the gonio data (Lrb) of the geometry thus input is measured, and the data as a result of the measurement is supplied to the Lrs calculating section 131.

In the Lrs calculating section 131, the data of the lower layer reflection light component (Lru) calculated using the same geometry and the data of the internal reflection light component (Lri) measured using the same geometry are selected and retrieved from the second memory 152, and the lower layer reflection light component (Lru) and the internal reflection light component (Lri) are subtracted from the gonio data (Lrb).

The data of the surface reflection light component (Lrs), which has been calculated as above, is supplied to the Lrs fitting processing section 132. In the Lrs fitting process section 132, the surface reflection light component thus supplied is subjected to fitting with the Torrance-Sparrow model. With this, the surface reflection light components (Lrs) of all specular reflection geometries are calculated, and the data obtained by the calculation is stored in the second memory 152.

As a result of the processes above, the second memory 152 stores the lower layer reflection light components (Lru), internal reflection light components (Lri), and surface reflection light components (Lrs) of all specular reflection geometries. In the second memory 152, these components are associated with the corresponding geometries. The specular reflection light component calculating section 114 adds up the reflection light components corresponding to the same specular reflection geometry. With this, the specular reflection light components Lr of all specular reflection geometries are obtained (S8 in FIG. 8).

Figure 11:
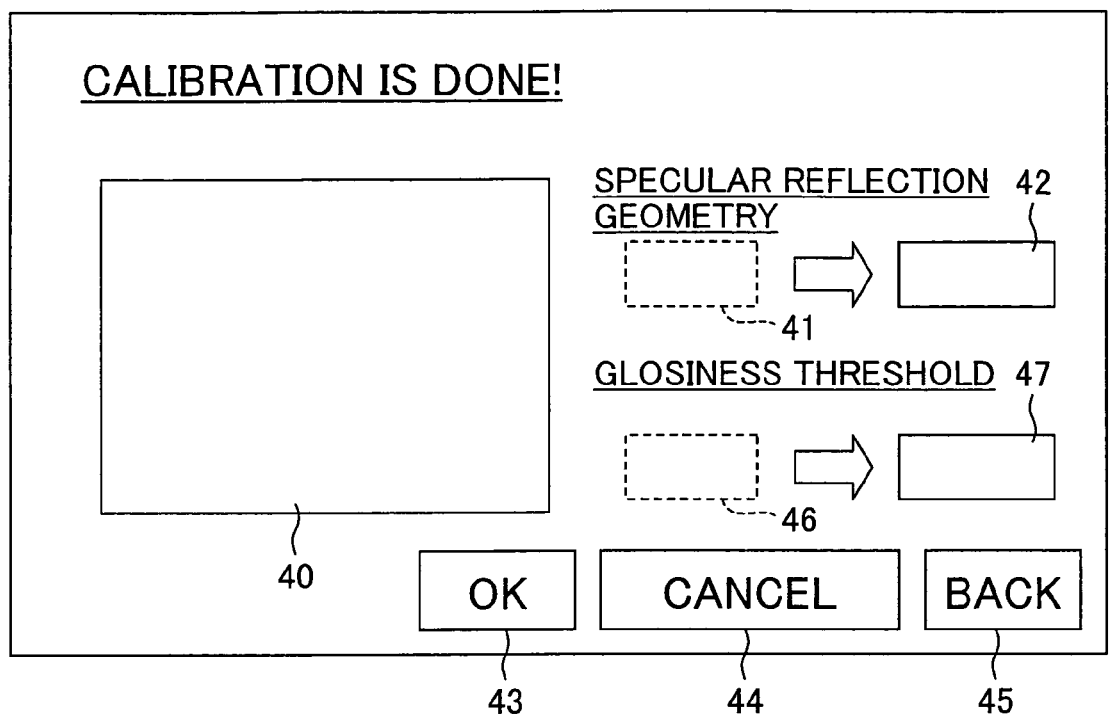
FIG. 11 is a diagram schematically illustrating an example of a screen displaying a result of a measurement, the result being displayed on a display section of the specular glossiness simulation device as illustrated in FIG. 1.

The data as a result of the measurement of the specular reflection light components Lr is supplied to the operation input section 102, and displayed on the display section 122. FIG. 11 shows an example of a screen of the display section 122 showing the measurement result.

As shown in FIG. 11, after the measurement of the specular reflection light components Lr, the display section 122 displays: a graph 40 of the specular reflection light components Lr; an input item 41 for the specular reflection geometry; a calculation result 42 of the specular reflection light component Lr of the geometry inputted in the input item 41; an input item 46 for the gloss threshold; a calculation result 47 of the specular reflection geometry that indicates the threshold inputted in the input item 46; an OK button 43; a cancel button 44; and a back button 45. The graph 40 of the specular reflection light components Lr shows the list of all specular reflection light components Lr, in a case where the incident light angles are in the range of 10° and 80°. It is therefore possible to see to what extent a sample specular reflection light component is dependent on the angle. The results shown in the graph 40 are calculated in the specular reflection light component calculating section 114 by adding up the lower layer reflection light components Lru, internal reflection light components Lri, and surface reflection light components Lrs of all specular reflection geometries stored in the second memory 152.

In the specular gloss simulation device 100, an arbitrary angle is input in the input item 41 of the specular reflection geometry shown in FIG. 11, and the OK button 43 is pushed. With this, the value of the specular reflection light component of the angle thus input is obtained. The calculated value of this case is equal to a point on the graph 40 of the specular reflection light components Lr.

In the meanwhile, a desired specular reflection light component (corresponding to the luminance, here) is inputted in the input item 46 for the gloss threshold and the OK button 43 is pushed. With this, an angle corresponding to the specular reflection light component thus input is displayed as the calculation result 47. The calculation result proves that angles corresponding to the specular reflection light components higher than the component thus input are higher than the displayed angle. In other words, the specular gloss simulation device 100 of the present embodiment makes it possible to calculate the specular reflection light components of all specular reflection geometries. Therefore, by varying the specular reflection geometry (incident and light reflection angles), it is possible to confirm in which case the specular reflection light component exceeds a predetermined value. This can be effectively used as a novel valuation standard for the gloss.

If the cancel button 44 in the result screen shown in FIG. 11 is pushed, the result screen finishes and the measurement mode is compulsorily terminated. If the back button 45 is pushed, the data input screen shown in FIG. 10 is shown again.

In a case where the specular reflection light component simulated as above is converted to the gloss in conformity to Japanese Industrial Standards, the gloss is figured out in such a manner that a relative value is calculated based on a value in the case of a standard plate (glass plate with a refractive index of 1.567) specified as a standard sample.

Figure 12:
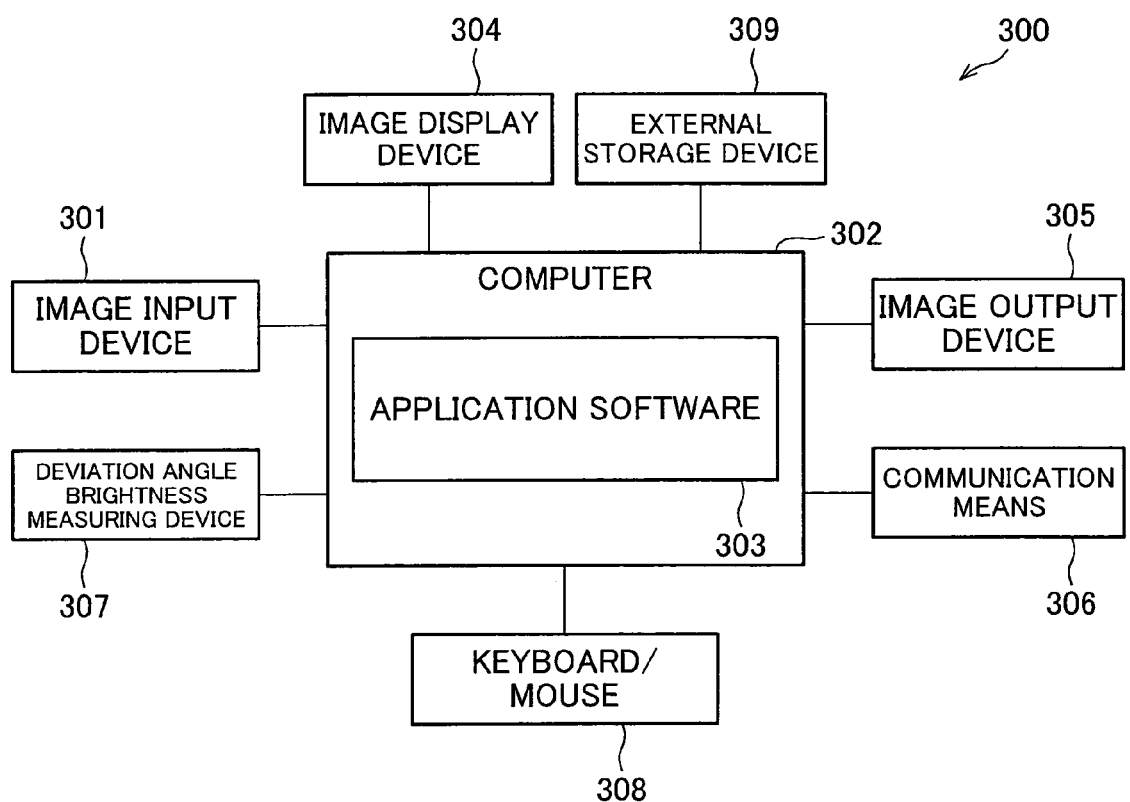
FIG. 12 is a block diagram of an arrangement of a computer system including a function of the specular glossiness simulation device as illustrated in FIG. 1.

The specular gloss simulation device 100 may be realized using a computer system. FIG. 12 shows a computer system 300 capable of executing the functions of the specular gloss simulation device 100.

The computer system 300 includes: an image input device 301 such as a flatbed scanner, film scanner, and digital camera; a computer 302 which performs various processes such as image processing, by loading a predetermined program (application software 303); an image display device 304, such as a CRT display and liquid crystal display, that displays processing results of the computer 302; and an image output device 305, such as a printer or the like, which outputs, on a piece of paper or the like, the processing result of the computer 302. The computer system 300 further includes: a network card or modem as communication means 306 for the connection with a server via a network; a gonio-photo spectrometer as a gonio data measuring device 307 that measures the gonio data; a keyboard/mouse 308 by which information input is performed to cause the computer 302 to conduct a desired process; an external storage device 309 as external storage means storing programs and data; or the like.

To perform the specular gloss simulation of the present invention by the computer system 300, the computer 302 functions as the calculating section 101, the gonio data measuring device 307 functions as the gonio data measuring section 104, and the keyboard/mouse 308 functions as the operation keys 121, and the image display device 304 functions as the display section 122. The storage section 103 may be provided in the external storage device 309 or in the computer 302.

The processing steps performed by the calculating section 101 of the specular gloss simulation device 100 of the present embodiment and by the sections 11-114 in the calculating section 101 are realized by causing computing means such as a CPU to execute a program stored in storage means such as ROM (Read Only Memory) or RAM, so as to control the input means such as a keyboard, output means such as a display, or a communication means such as an interface circuit. On this account, the functions and processes of the specular gloss simulation device 100 can be realized only by causing the computer having the aforesaid means to read a storage medium storing the program and execute the program. If the program is stored in a removable storage medium, the aforesaid functions and processes can be realized any computer.

The storage medium may be a program medium such as a memory (not illustrated) for executing processes on a microcomputer, e.g. ROM. Alternatively, the storage medium may be a program medium which is inserted into and read by a program reader provided as the external storage device 309.

In any event the stored program is preferably accessed and executed by a microprocessor. Once read out, the program is preferably downloaded to a program storage area of the microcomputer and executed. The program for the download is stored in the main body device in advance.

The aforesaid program medium is a storage medium arranged so that it can be separated from the main body. Examples of such a program medium include a tape, such as a magnetic tape and a cassette tape; a magnetic disk, such as a flexible disk and a hard disk; a disc, such as a CD/MO/MD/DVD; a card, such as an IC card (inclusive of a memory card); and a semiconductor memory, such as a mask ROM, an EPROM (erasable programmable read only memory), an EEPROM (electrically erasable programmable read only memory), or a flash ROM. All these storage media hold a program in a fixed manner.

Alternatively, if a system can be constructed which can connects to the Internet or other communications network, it is preferable if the program medium is a storage medium carrying the program in a flowing manner as in the downloading of a program over the communications network.

Further, when the program is downloaded over a communications network in this manner, it is preferable if the program for download is stored in a main body device in advance or installed from another storage medium.

Second Embodiment

Referring to FIG. 13 through FIG. 19, the following will describe a Second Embodiment of the present invention. The foregoing First Embodiment described the specular gloss simulation method that is applicable regardless of the size of the colorant material particles of the dye ink, pigment ink, or toner in the colorant material layer of the sample. However, the present embodiment describes a specular gloss simulation method and specular gloss simulation device for more accurately calculating specular gloss components of the sample when the colorant material particles contained in the colorant material layer have a relatively large diameter (i.e., when the colorant material particles are pigment such as pigment ink or toner). Examples of such pigment include pigment ink and toner.

First, the specular gloss simulation device of the present embodiment is described in regard to the dichromatic reflection (BRDF) model theory used for the simulation of specular gloss of a sample. Here, description of the BRDF model will be given through the case where it is used to calculate reflection light components of a sample having the bilayer structure of the base material and the colorant material layer in which toner (pigment) is contained as colorant material particles.

Figure 14:
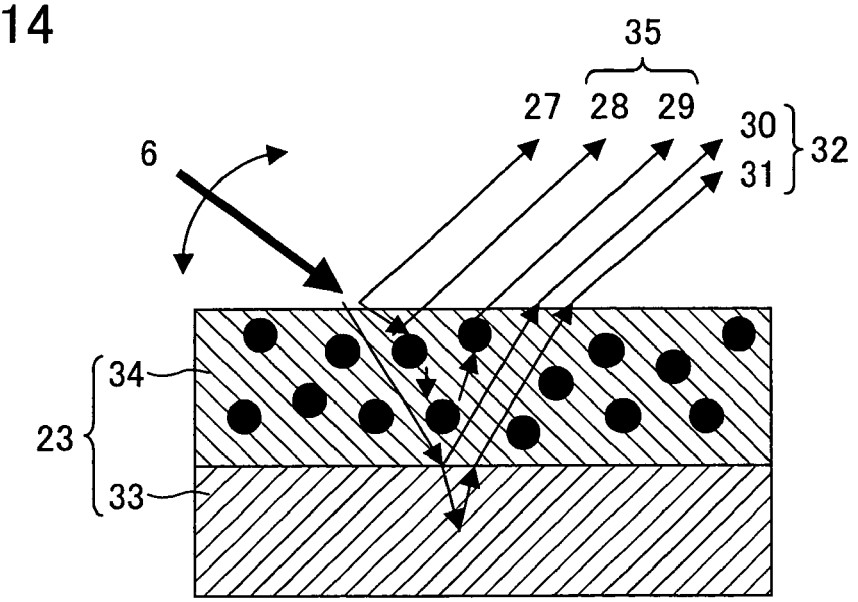
FIG. 14 is a diagram schematically illustrating a method of dividing reflection light components of a sample having a structure with two layers, according to the embodiment 2.

FIG. 14 schematizes how the reflection light components of the bilayer sample are split into individual components. As illustrated in FIG. 14, a sample 23 includes an upper layer portion 13 constituting a toner image (colorant material layer), and a lower layer portion 33 constituting a base material such as paper or a transparent film. According to the dichromatic reflection (BRDF) model theory, the reflection light components of the light from a light source 6 include: a surface reflection light component (Lrss) 27 and an internal reflection light component 35, both from the upper layer portion 34, and a surface reflection light component 30 and an internal reflection light component 31, both from the lower layer portion 33. The composite light of these components becomes the reflected light from the sample 23. In the present embodiment, the internal reflection light component 35 from the upper layer portion 34 can be further divided into a reflection light component (Lrsp) 28 directly reflected by the colorant material particles, and a diffuse reflection light component (Lrd) 29 produced by scattering of light between the colorant material particles. In order to calculate the reflected light components 27 through 31 by the BRDF model, more than one unmeasurable parameter needs to be estimated.

However, since the measurement of the internal reflection light component 31 reflected from the lower layer portion 33 is difficult, the present invention combines the internal reflection light component 31 with the surface reflection light component 30 also from the lower layer portion 33, and uses the sum of these reflection light components as a lower layer reflection light component (Lru) 32. By calculating the lower layer reflection light component 32 based on measurement data obtained only from the lower layer portion 33, a specular reflection light amount can be accurately calculated for a wide variety of samples images according to the BRDF model. By thus calculating the lower layer reflection light component 32 with the surface reflection light component 27, the reflection light component 28 of the colorant material particles, and the diffuse reflection light component 29 from the upper layer portion 34, an accurate specular reflection light amount can be obtained.

As the BRDF model effective as the mathematical models for calculating the respective reflection light components, the present invention can use the (1) Ward Model, (2) Phong Model, (3) Oren-Nayar Model, and (4) Torrance-Sparrow Model, which are described in the First Embodiment.

Of these mathematical models, the Ward model and the Phong model have been proposed based on isotropic scattering of light, whereas the Oren-Nayar model and the Torrance-Sparrow model are based on non-isotropic scattering of light. In the present embodiment, the Torrance-Sparrow model is adopted as the mathematical model for calculating the surface reflection light component 27 and the reflection light component 28 of the colorant material particles, and the Oren-Nayar model is adopted as the mathematical model for calculating the diffuse reflection light component 29 produced by scattering of light between the colorant material particles. This is because more accurate values can be obtained when non-isotropic scattering of light is taken into consideration, though it complicates the equations.

FIG. 5 represents a geometric arrangement according to the BRDF model. FIG. 6 represents geometric definitions of object surfaces according to the BRDF model.

In calculating the diffuse reflection light component Lrd using the Oren-Nayar model, mathematical value LrON is calculated first according to Equation (1) below.

$$LrON = \frac{\sigma}{\pi}E0\cos\theta i[C1(\sigma) + \cos(\phi r - \phi i)C2(\alpha; \beta; \phi r - \phi i; \sigma)\tan\beta) + \quad (1)$$

$$(1 - |\cos(\phi r - \phi i)|)C3(\alpha; \beta; \sigma)\tan\left(\frac{\alpha+\beta}{2}\right) +$$

$$0.17\frac{\rho^2}{\pi}E0\cos\theta i\frac{\sigma^2}{\sigma^2+0.13}\left[1 - \cos(\phi r - \phi i)\left(\frac{2\beta}{\pi}\right)^2\right]$$

$$C1 = 1 - 0.5\frac{\sigma^2}{\sigma^2+0.33}$$

$$C2 = \begin{cases} 0.45\frac{\sigma^2}{\sigma^2+0.09}\sin\alpha & (\text{if } \cos(\phi r - \phi i) \geq 0) \\ 0.45\frac{\sigma^2}{\sigma^2+0.09}\sin\alpha & \left(\sin\alpha - \left(\frac{2\beta}{\pi}\right)^3\right) \text{ (if not)} \end{cases}$$

$$C3 = 0.125\left(\frac{\sigma^2}{\sigma^2+0.09}\right)\left(\frac{4\alpha\beta}{\pi^2}\right)^2$$

In Equation (1), $\theta i$ is the zenith angle in the light source direction, $\phi i$ is the azimuth angle in the light source direction, $\theta r$ is the zenith angle in the light reflection direction, $\phi r$ is the azimuth angle in the light reflection direction, $\sigma$ is the roughness variable of the surface profile, $E0$ is the radiant luminance incident on the sample, $\rho$ is the refractive index of the microscopic surface of the sample surface, $\alpha=\max[\theta r, \theta i]$, and $\beta=\min[\theta r, \theta i]$ (see FIG. 5, FIG. 6). Note that, the mathematical formula used to calculate LrON in this embodiment is the same as that used in the First Embodiment.

In calculating the surface reflection light component Lrss and the reflection light component Lrsp of the colorant material particles according to the Torrance-Sparrow model, mathematical value LrTS (LrTSs and LrTSp) is calculated first according to Equation (2) below.

$$LrTS = E0\frac{FGAF}{\cos\theta r\cos\theta a}ce^{-\frac{\theta a^2}{2\sigma^2}} \quad (2)$$

$$GAF = \max\left[0, \text{Min}\left[1, \frac{2<s,n><a,n>}{<s,a>}, \frac{2<v,n><a,n>}{<v,a>}\right]\right]$$

$$c = \int_{\theta a=0}^{\frac{\pi}{2}}\int_{\phi a=0}^{2\pi}e^{-\frac{\theta a^2}{2\sigma^2}}\sin\theta a d\phi a d\theta a$$

In Equation (2), F is the Fresnel reflection index, n is the normal vector of the sample 3, s is the vector of the light source direction; v is the vector of the light reflection direction, a is the bisector vector of s and v, $\theta r$ is the zenith angle of the light reflection direction, $\theta a$ is the zenith angle of vector a, $\phi a$ is the azimuth angle of vector a, $\sigma$ is the roughness variable of the surface profile, and $E0$ is the radiant luminance incident on the sample. Further, in Equation (2), <x, y> (x, y are arbitrary numbers) is the inner products of the vectors (see FIG. 5, FIG. 6). The mathematical formula used to calculate LrTS in this embodiment is the same as that used in the First Embodiment.

Subsequently, referring to the flow chart in FIG. 13, a method will be described by which the amount of specular reflection light is calculated for each geometry from a measured value of luminance in a predetermined geometry using the above technique.

First, to calculate an lower layer reflection light component Lru, the transmittance of only the upper layer portion (toner image) 34 of a sample for which the specular reflection light component is to be calculated is calculated (step S11). The measurement geometry here includes a light source, a sample, and a light receiver positioned along a straight line. In such a geometry, the light source shines right above the sample. That light which is received by the light receiver located right under the sample is measured with a transmission density meter as light having transmitted the sample. Then, the transmission density Dt for only the upper layer portion 34 is obtained by calculating a differential between a sample with a toner image formed thereon (a sample made up of the upper layer portion 34 and the lower layer portion 33) and a sample made up of only the lower layer portion (paper) 33. A transmittance Tt for only the upper layer portion 34 (in other words, the toner image) is given by Tt=10^(-Dt).

Throughout the following steps, the refractive index (literature value) of resin which is a main component of toner is used as the refractive index of the upper layer portion (toner image) 34.

Next, a sample with no upper layer portion 34, that is, a sample with only the lower layer portion 33 (in the present embodiment, paper or transparent film still carrying no toner image formed thereon) is prepared. With the light source incidence direction and the light reflection direction of the sample with only the lower layer portion 33 being resolved at high resolution, gonio data is then measured (step S12). Here, CIE 1976 L*a*b* (CIE: Commission International de l'Eclairage. L* is a lightness, and a* indicates redness-greenness and b* indicates yellowness-blueness) color space is used for the measurement. Therefore, the value of L* is employed as the gonio data.

Figure 15:
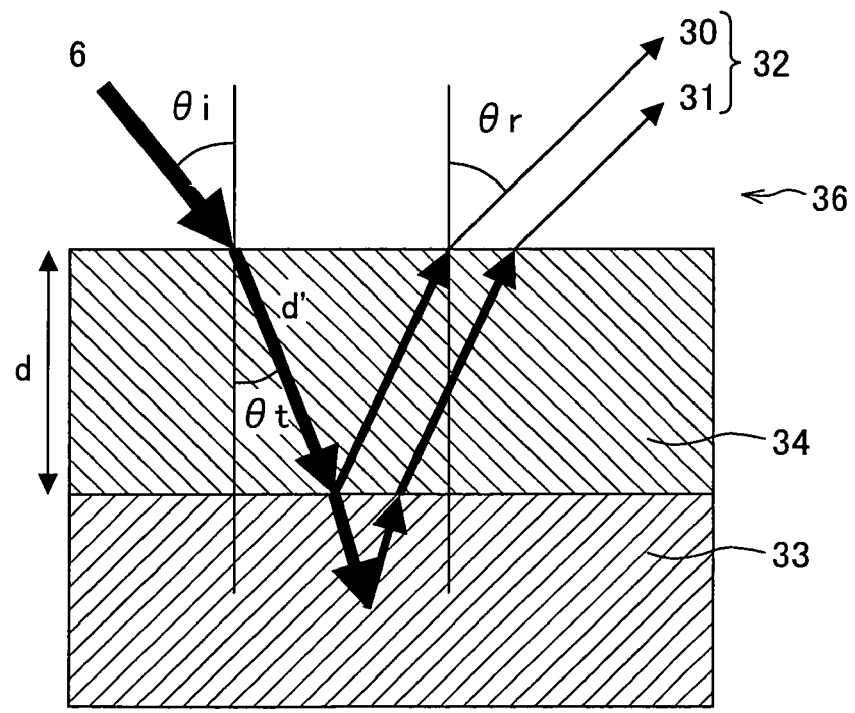
FIG. 15 is a diagram schematically illustrating a refraction phenomenon of light and attenuation of an amount of light, which are taken into consideration when an lower layer reflection light component is calculated in the embodiment 2.

The lower layer reflection light component Lru is calculated from this data (step S13). FIG. 15 is a diagram schematically illustrating a refraction phenomenon of light and attenuation of an amount of light, which are taken into consideration when the lower layer reflection light component Lru is calculated. Light incident to the sample at an incident light angle θi refracts at the interface between an air layer 36 and the upper layer portion 34. This refraction phenomenon obeys Fresnel's theory. The angle θt after the refraction is given by Fresnel's law (n1×sin θi=n2×sin θt, where n1 is the refractive index of a pre-incidence medium, and n2 the refractive index of a post-incidence medium). Light is attenuated at the interface due to the refraction as it passes through the toner layer. The Fresnel transmittance Tn of that light is given by equation (3):

$$Tn = \left[\left(\frac{n2\cos\theta t}{n1\cos\theta i}\right)\left(\frac{2n1\cos\theta i}{n2\cos\theta t + n1\cos\theta t}\right)^2 + \left(\frac{n2\cos\theta t}{n1\cos\theta i}\right)\left(\frac{2n1\cos\theta i}{n1\cos\theta i + n2\cos\theta t}\right)^2\right]/2 \quad (3)$$

As light passes through the upper layer portion 34, the light is attenuated by the upper layer portion 34 before reaching the lower layer portion 33. The attenuation obeys the Beer-Lambert law (−logT=a×d, where a is the absorption coefficient of a colorant material layer, d is the thickness of the colorant material layer, and T is the transmittance). The length of the optical path in the upper layer portion 34 traveled by the light before reaching the lower layer portion 33 changes with the incident light angle. The apparent transmittance Tt' in accordance with the changes in the length of the optical path is given by −logTt'=a×(d/cos θi). Light attenuation is evaluated in terms of the apparent transmittance.

From the above description, the amount of incident light reaching the lower layer portion 33 is calculated by evaluating the attenuation of the amount of light from the apparent transmittance Tt' in accordance with the Fresnel transmittance Tn and the changes in the length of the optical path. The calculation also takes into consideration the changes of the incident light angle of the light to the lower layer portion 33 caused by the refraction. A similar optical phenomenon occurs when the reflection from the lower layer portion 33 travels back to the air layer. Therefore, the lower layer reflection light component Lru is calculated by calculating from the gonio data of the sample with only the lower layer portion (paper) measured in S12 for all incident light angles and light reflection angles with the two refractions and an attenuation of light (see FIG. 15) taken into consideration. If the incident light angle θt after the refraction has decimal places, the angle is interpolated by proration from the preceding and succeeding angle values. There are no particular limitations on angle resolution in the process. Here, the resolution is 1° because the measuring device has a maximum angle resolution of 1°. To calculate the specular reflection light component more precisely, the angle resolution is preferably 1° or less.

Next, to calculate the diffuse reflection light component Lrd, the luminance value Lra (L* of CIE 1976 L*a*b*) of the sample is measured in one certain geometry which contains almost zero surface reflection light component (step S14). This geometry is termed the non-specular reflection geometry. Generally, the more the geometry differs from specular reflection, the smaller the surface reflection light component.

The non-specular reflection geometry selected here therefore preferably has a large light source incident light angle and includes a light source incidence position and a light receiving position in close proximity. For the present embodiment, an exemplary geometry is selected where the light source incident light angle θi is 45° (φi=0°) and the light reflection angle θr is −60° (φr=0°).

Next, the density distribution of the toner image sample is measured, and its roughness variable σp is calculated from the measured value (step S15). A specific method for the calculation of the roughness variable σp will be detailed later.

Subsequently, the lower layer reflection light component Lru calculated in the same geometry is subtracted from the luminance value Lra measured in S14. Further, the surface reflection light component Lrss and the colorant material particle reflection light component Lrsp are approximated to 0. The remaining reflection light component is designated the diffuse reflection light component Lrd. The diffuse reflection light component Lrd thus obtained is subjected to fitting using an Oren-Nayar model (step S16). Fitting here means that an unknown parameter is calculated, and the internal reflection light component is obtained for each geometry, so that the internal reflection light component calculated from the luminance value Lra measured in the selected non-specular reflection geometry can be represented with an Oren-Nayar model.

As the roughness variable σ (see FIG. 5) of the density distribution used in the above process is used a roughness variable σp calculated on the basis of the density distribution of the sample measured in S15. E0 (see FIG. 5) is irradiance incident to the sample. Here, since the measured value space is CIE 1976 L*a*b* space, and L* is employed, E0=100π. From these values, the reflectance ρ of a small plane on the sample surface is estimated. The reflectance ρ of the small plane on the sample surface is never negative in the physical model; only positive values are employed.

Inserting these numeric values to equation (1), the parameters required by the Oren-Nayar model are estimated. Thus, an Oren-Nayar model calculated value LrON is determined. The magnitude of the Oren-Nayar model calculated value LrON is also subjected to fitting by estimating the reflectance parameter ρ for the small plane on the sample surface. It is therefore possible to calculate the diffuse reflection light component Lrd for each geometry without any particular scaling of the Oren-Nayar model calculated value LrON. That is, the calculated LrON corresponds to the diffuse reflection light component Lrd (Lrd=LrON).

Next, to calculate the surface reflection light component Lrss and the colorant material particle reflection light component Lrsp, the luminance value Lrb in one specular reflection geometry is measured (step S17). The geometry is termed the specular reflection geometry. The specular reflection geometry selected here is such that the light source incident light angle is 45° (φi=0°), and the light reflection angle is 45° (φr=180°). The present invention is not limited to these angles.

Subsequently, the density distribution of the toner image sample is measured, and its roughness variable σp is calculated from the measured value. In addition, the surface shape of the sample is measured, and its roughness variable σs is calculated from the measured value (step S18). The roughness variable σp of the density distribution calculated in S15 issued here. A specific method for the calculation of the roughness variable σs of the surface shape will be detailed later.

Next, the lower layer reflection light component Lru calculated in the same geometry and the diffuse reflection light component Lrd are subtracted from the luminance value Lrb (L* of CIE 1976 L*a*b*) measured in S17. The remaining reflection light component is designated a combined component of the surface reflection light component Lrss and the colorant material particle reflection light component Lrsp.

Then, the model calculated value LrTS is calculated individually for the surface reflection light component Lrss and the colorant material particle reflection light component Lrsp using a Torrance-Sparrow model (step S19).

The roughness variable σ for the Torrance-Sparrow model used in the process is a parameter defining the range of the reflection light component in the physical model. Therefore, for the surface reflection light component Lrss, the roughness variable σs of the surface shape obtained in S18 is employed. For the colorant material particle reflection light component Lrsp, the roughness variable σ of the density distribution obtained in S18 is employed. E0 (see FIG. 5) is 100π similarly to the Oren-Nayar model. F is set to 1 to obtain surface reflection in the specular reflection geometry. The Torrance-Sparrow model involves no estimation parameter. Inputting request parameters determines a Torrance-Sparrow model calculated value LrTS (that is, the Torrance-Sparrow model calculated value LrTSs for the surface reflection light component Lrss and the Torrance-Sparrow model calculated value LrTSp for the colorant material particle reflection light component Lrsp).

Next, fitting is carried out by obtaining respective allocations from the model calculated values LrTSs and LrTSp so as to achieve the measured luminance value (step S20). Specifically, a shape parameter k that satisfies Lrb=k×LrTSs+(1−k)× LrTSp is calculated, and an allocation ratio of the surface reflection light component Lrss and the colorant material particle reflection light component Lrsp is determined. Thus, the surface, reflection light component Lrss and the colorant material particle reflection light component Lrsp for each specular reflection geometry are calculated.

With these steps, the lower layer reflection light component Lru, the diffuse reflection light component Lrd, the surface reflection light component Lrss, and the colorant material particle reflection light component Lrsp are individually calculated. By adding these calculate values in the same specular reflection geometry, the specular reflection light component (amount of specular reflection light) Lr is obtained (step S21).

The aforementioned specular gloss simulation method takes every kind of image (low gloss image, low density image, etc.) into consideration, and therefore assumes separating a sample on which measurement is to be made into an upper layer portion and an lower layer portion. However, special measurement samples (high density, high gloss samples) may be treated differently. The specular reflection light component Lr may be calculated using only the reflection light component from only the upper layer portion (the surface reflection light component Lrss, the colorant material particle reflection light component Lrsp, and the diffuse reflection light component Lrd). This is because in this case, the lower layer reflection light component Lru is too small to affect the specular reflection light component Lr.

In the aforementioned specular gloss simulation method, S1 to S13 are lower layer reflection light component forming steps, S14 to S16 are internal reflection light component forming steps, S17 to S19 are surface reflection light component forming steps, S19 is a shape parameter calculating step, and S20 is a specular reflection light amount calculating step.

Figure 16:
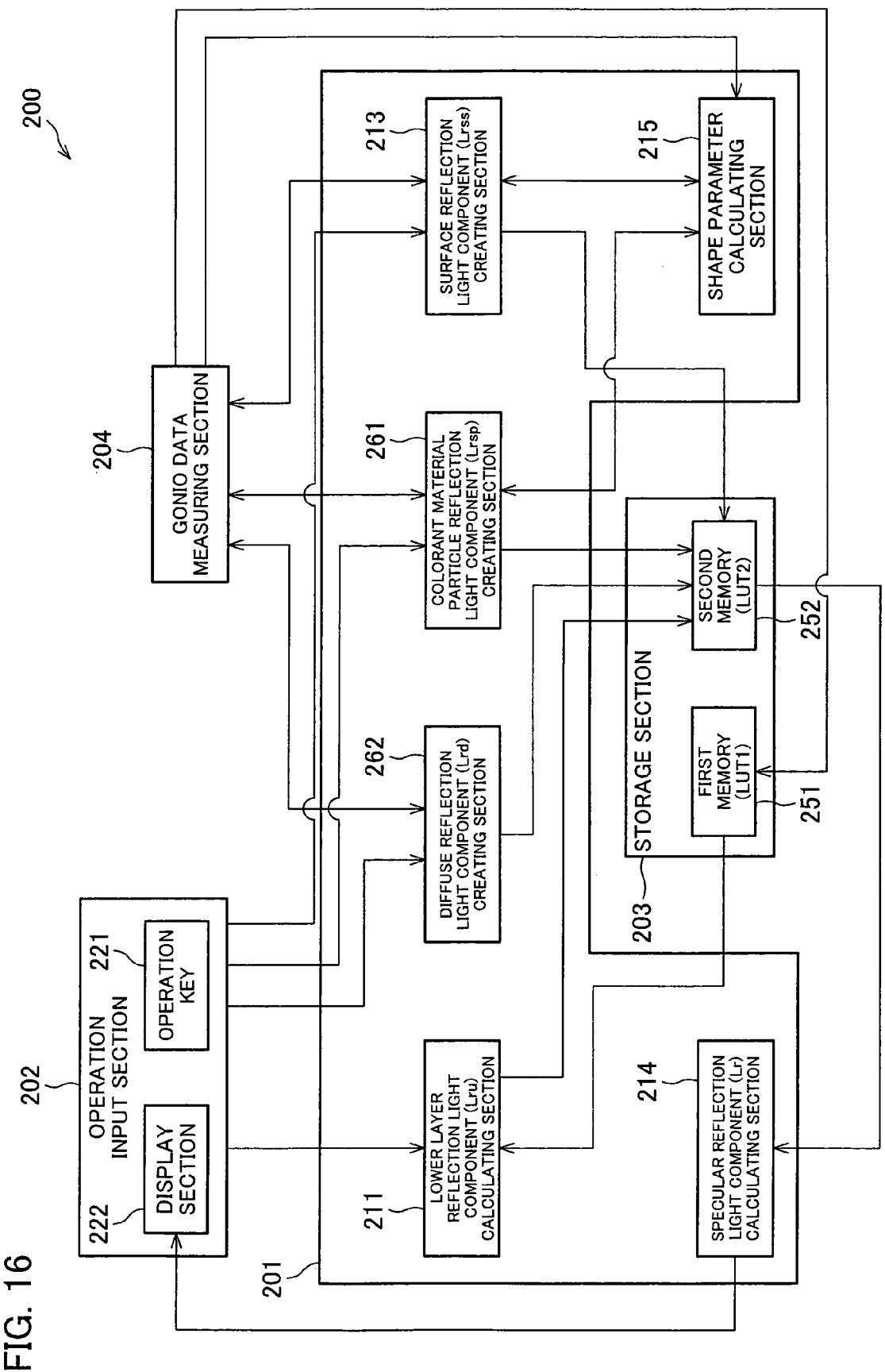
FIG. 16 is a block diagram of an arrangement of a specular gloss simulation device, according to the embodiment 2 of the present invention.

Next, an arrangement of a specular gloss simulation device according to the present invention is described below. The specular gloss simulation device according to the present embodiment calculates out the specular reflection light component of each specular reflection geometry by performing the process illustrated in the flowchart of FIG. 13. From the specular reflection light components thus obtained, the specular gloss simulation device simulates the specular gloss. In FIG. 16, an arrangement of a specular gloss simulation device 200 according to the present invention is illustrated.

As illustrated in FIG. 16, the specular gloss simulation device 200 is provided mainly with a calculating section 201, an operation input section 202, a storage 203, and a gonio data measuring section 204.

The calculating section 201 calculates out a specular reflection light component from (a) data of refractive index and transmittance, the variable of the density distribution on the sample, the variable of the surface coarseness of the sample (which has been inputted via the operation input section 202) of the upper portion (toner image) 34, (b) non-specular reflection geometry/specular reflection geometry being designated via the operation input section 202, and (c) gonio data being measured by the gonio data measuring section 204.

The calculating section 201 is provided with a lower layer reflection light component calculating section (lower layer reflection light component creating section) 211, a diffuse reflection light component creating section (internal reflection light component creating section) 262, a surface reflection light component creating section 213, and a specular reflection light component calculating section (specular reflection light amount calculating section) 214. The lower layer reflection light component calculating section 211 is used for calculating a lower layer reflection light components (Lru) in each geometry. The diffuse reflection light component creating section 262 is used for calculating an internal reflection light component (Lri) from a measured gonio data in one non-specular reflection geometry, and performing fitting process to fit the thus calculated internal reflection light component (Lri) to the Oren-Nayar model thereby to obtain the diffuse reflection light component (Lrd) which is an internal reflection light component in each geometry. The surface reflection light component creating section 213 is used for calculating a surface reflection light component (Lrss) from a measured gonio data in one specular reflection geometry, and performing fitting process to fit the thus calculated surface reflection light component (Lrs) to the Torrance-Sparrow model thereby to obtain a surface reflection light component (Lrss) in each specular reflection geometry. The specular reflection light component calculating section (specular reflection light amount calculating section) 214 is used for calculating a specular reflection light component (specular reflection light amount) (Lr) by adding up the reflection light components thus obtained via the respective sections. The specular reflection light component calculating section 214 adds up the reflection light components of the same specular reflection geometry thereby to calculate out the specular reflection light component in each specular reflection geometry.

In the present embodiment, the internal reflection light component 35 is considered such that it is made up with the colorant material particle reflection light component (Lrsp) 28 and the diffuse reflection light component (Lrd) 29. The colorant material particle reflection light component (Lrsp) 28 is calculated from the colorant material particle reflection light component (Lrsp) 28 based on the gonio data measured in one specular reflection geometry. Therefore, the calculating section 201 is further provided with a colorant material particle reflection light component creating section 261 for calculating the colorant material particle reflection light component (Lrsp) 28 from gonio data measured in one specular reflection geometry, and performing fitting process to fit the thus calculated colorant material particle reflection light component (Lrsp) 28 to the Torrance-Sparrow model thereby to create the colorant material particle reflection light component (Lrsp) 28 in each specular reflection geometry.

Moreover, the colorant material particle reflection light component creating section 261 is provided with an Lrsp calculating section (not shown) for calculating the colorant material particle reflection light component from the measured gonio data in one specular reflection geometry, and an Lrsp fitting process section (not shown) for performing fitting process to fit the thus calculated colorant material particle reflection light component (Lrsp) to the Torrance-Sparrow mode thereby to obtain the colorant material particle reflection light component (Lrsp) in each specular reflection geometry. Moreover, the diffuse reflection light component creating section 262 is provided with an Lrd calculating section (not shown) for calculating the diffuse reflection light component from the gonio data measured in one non-specular reflection geometry, and an Lrd fitting process section (not shown) for performing fitting process to fit the thus calculated diffuse reflection light component to the Oren-Nayar model thereby to obtain the diffuse reflection light component in each geometry.

Moreover, the surface reflection light component creating section 213 is provided with an Lrss calculating section (not shown) for calculating the surface reflection light component (Lrss) from the measured gonio data in one specular reflection geometry, and an Lrss fitting process section (not shown) for performing fitting process to apply the thus calculated surface reflection light component (Lrss) in the Torrance-Sparrow mode thereby to obtain the surface reflection light component (Lrss) in each specular reflection geometry.

In the present embodiment, the measured gonio data in one specular reflection geometry is allocated to the surface reflection light component (Lrss) and the colorant material particle reflection light component (Lrsp). Therefore, the calculating section 201 is provided with a shape-parameter calculating section 215 for determining how the measured gonio data is allocated to the surface reflection light component (Lrss) and the colorant material particle reflection light component (Lrsp).

The operation input section 202 is used for inputting various numerical values necessary for the calculation of the specular reflection light component, and for displaying a result of calculation performed by the calculating section 201. The operation input section 202 includes operation keys 221 for inputting numerical values and/or the like, and a display section 222 for displaying items such as information inputted via the operation keys 221, the result of calculation, and/or the like.

The storage section 203 is used for storing therein a result of the measurement performed by the gonio data measuring section 204, and the result of the calculation performed by the calculating section 201. The storage section 203 is provided with a first memory 251 (LUT 1) and a second memory 252 (LUT 2). The first memory 251 is for storing therein gonio data of a sample measured by the gonio data measuring section 204, the sample having a lower layer portion (paper) 33 only. The second memory 252 is for storing therein each reflection light component calculated out by the calculating section 201.

The gonio data measuring section 204 measures the gonio data of the sample having the lower layer portion (paper) 33 only, and the gonio data of the sample having the two-layered structure, that is, having the lower layer portion 33 and the upper layer portion (toner image) 34. The gonio data measuring section 204 has an angular resolution of 1°, by which the gonio data measuring section 204 is able to measure the gonio data per degree. For simulating the specular glossiness by using the specular gloss simulation device 200, the gonio data of the sample having the lower layer portion (paper) 33 only is measured per degree, meanwhile for the sample having the lower layer portion 33 and the upper layer portion 34, it is only required to measure the gonio data of one specular reflection geometry and one non-specular reflection geometry.

Next, how to simulate the specular gloss in each specular reflection geometry of a sample by using the specular gloss simulation device 200 is described below, referring to FIGS. 13 and 16.

Firstly, transmittance and refractive index of an upper layer portion of a sample (toner image) are measured (at S1 in FIG. 11). The transmittance and refractive index are to be inputted into the specular gloss simulation device 200 in order to measure the specular gloss component. Transmittance Tt is calculated out from Equation $Tt=10^{(-Dt)}$, where Dt is a transmission density of only the upper layer portion. The transmission density is worked out by obtaining a difference between transmission density of the sample on which the toner image is formed (i.e., the sample having the lower layer portion 33 and the upper layer portion 34) and that of the sample having the lower layer portion (paper) 33 only. A transmission density meter is used to measure the transmission density of the sample on which the toner image is formed (i.e., the sample having the lower layer portion 33 and the upper layer portion 34) and that of the sample having the lower layer portion (paper) 33 only. The measurement of the transmission density may be carried out with a X-rite model 820 transmission densitometer made by X-rite Inc.

In the following process a refractive index (literature value) of a resin which is a main component of the toner is used as the refractive index of the upper layer portion (toner image) 34.

Next, a shape of the toner layer surface is measured, by using a shape-measuring microscope VK-9500 (manufactured by KEYENCE corp.) and a variable of a toner layer surface coarseness is calculated based on height information (data regarding Z-axis direction, where a plane of the sample is an X,Y plane) obtained from the measurement. Slope of a microscopic surface of the toner layer surface is calculated based on the height information of an adjacent picture element. Then, after the slope of the microscopic surface is plotted in a histogram, a standard deviation of the slope of the microscopic surface is calculated within a range of $2\sigma$ (95.5% of the data) thereby to obtain the variable $\sigma s$ of roughness of colorant material layer.

Meanwhile, a transmission image (i.e. an image obtained from transmissive light) for the sample is obtained by using a CCD camera CS-3910 (manufactured by Tokyo Electronic Industry) and a transmission-use light source whose amount of light output is 200 W, and the variable of evenness in density is calculated from the obtained transmission image data. The sample is placed between the CCD camera and the transmission-use light source. In other words, where the sample is X,Y plane, the CCD camera and the transmission-use light source are placed in the Z-direction. Then, the transmission image is obtained. Density of the picture elements of thus obtained transmission image is plotted in a histogram. Then, a standard deviation of transmission density is calculated within a range of $2\sigma$ (95.5% of the data) thereby to obtain the variable $\sigma p$ of density distribution.

Figure 13:
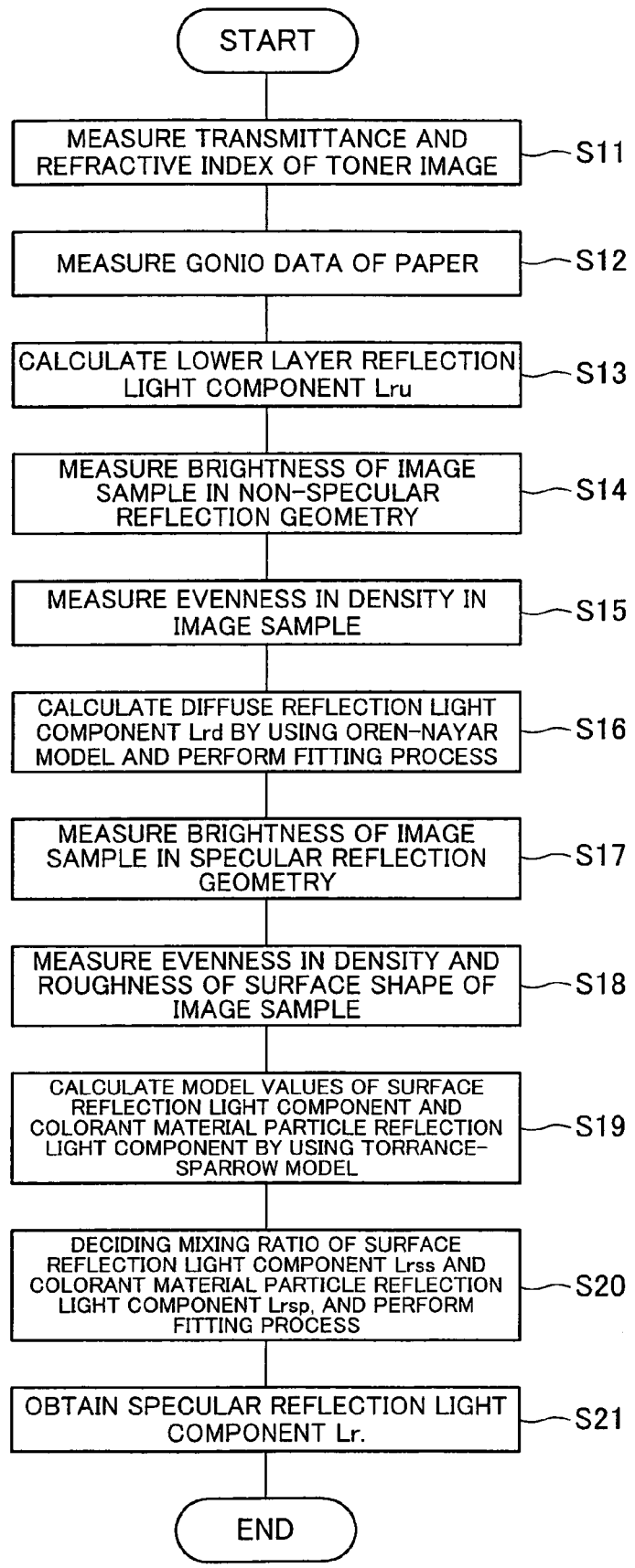
FIG. 13 is a flow chart of a process for calculating a specular reflection light component in each specular reflection geometry from a measured value of luminance in a predetermined geometry in an embodiment 2.

Here, the variable $\sigma p$ of the density distribution and the variable $\sigma s$ of roughness of surface shape of the sample are respectively measured in S15 and S17 of the flowchart of FIG. 13. When using the specular gloss simulation device 200 of the present invention for evaluating the specular gloss, the variables are measured in advance by using a separate device, and these variables are inputted at the same time the transmittance and the refractive index are inputted.

Figure 17:
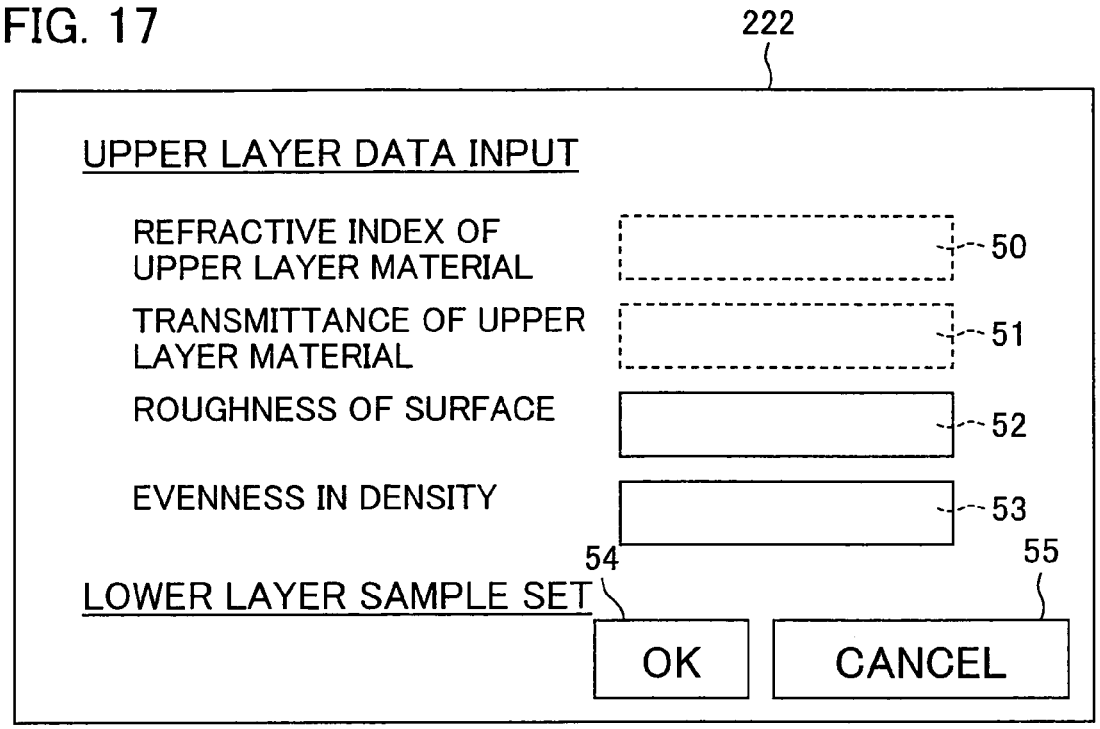
FIG. 17 is a diagram schematically illustrating an example of a data input screen displayed on a display section of the specular glossiness simulation device as illustrated in FIG. 16.

Next, the transmittance, the variables σp and σs and the refractive index of the upper portion 34 of the sample thus measured by the above methods are inputted via the operation keys 221 of the operation input section 202. FIG. 17 illustrates an example of a data input screen displayed on the display section 222 of the specular gloss simulation device 200. On the data input screen illustrated in FIG. 17, an input item 50 for the refractive index of the upper portion of the sample to be measured and an input item 51 for transmittance of the sample to be measured, an input item 52 for the variable of the roughness of the surface shape of the sample to be measured, and an input item 53 for the variable of density distribution of the sample to be measured are displayed. Further, an OK key 54, and a cancel key 55 are displayed on the data input screen illustrated in FIG. 17, which are touch-panel keys. Via the operation keys 221, the transmittance, the refractive index, and the variables σp and σs thus obtained by the above methods are inputted respectively into the input items 50 to 53 on the display section 222. If the cancel key 55 is pressed on this data input screen, a measurement mode is terminated with the data input screen inactivated.

Then, a base material made of the same material as that of the base material of the sample to be measured (i.e., the sample having the lower layer portion) is put in the gonio data measuring section 204 of the specular gloss simulation device 200, then the OK key 54 is pressed. In this way, the gonio data measuring section 204 measures the gonio data (CIE 1976*a*b*L*) of the sample having only the lower portion (at S12 in FIG. 13). The gonio data thus measured is stored in the first memory 251 of the storage section 203.

As the gonio data measuring section 204, gonio-photo spectrometer GSP-2S (made by Murakami Shikisai) may be used, for example. Moreover, the gonio data measurement of the sample having only the lower portion has the angular resolution of 1° with respect to the light source incident light angle and reflection light angle. Therefore, the first memory 251 stores the gonio data in association with the incident light angle and the reflection light angle, the gonio data being measured at the incident light angle and the reflection light angle per degree.

Next, based on the refractive index theory and attenuation theory, the lower layer reflection light component calculating section 211 calculates the lower layer reflection light component (Lru) in each geometry from the refractive index and transmittance of the upper layer portion which are inputted via the operation input section 202, and the gonio data stored in the first memory 251 (at S13 in FIG. 13). The lower layer reflection light component (Lru) thus calculated is then stored in the second memory 252 in the storage section 203.

After that, a similar process is carried out for a given non-specular reflection geometry selected. Information on the non-specular reflection geometry is inputted via the operation input section 202, and then the gonio data in the non-specular reflection geometry is measured (at S14 in FIG. 13). From the gonio data thus measured, the diffuse reflection light component (Lrd) of the non-specular reflection geometry is calculated out. Then, fitting process carried out in which the internal reflection light component (Lri) of the non-specular reflection geometry is applied in the Oren-Nayar model, thereby to obtain the diffuse reflection light component (Lrd) in each geometry (at S16 in FIG. 13). The variable σ of evenness in density for use in calculating the diffuse reflection light component (Lrd) is that variable σp of evenness in density of the sample which is inputted, in advance, via the operation input section 202.

Further, a similar process is carried out for a given specular reflection geometry selected. Information on the specular reflection geometry is inputted via the operation input section 102, and then the gonio data in the specular reflection geometry (at S17 in FIG. 13). From the gonio data thus measured, the surface reflection light component (Lrs) and the colorant material particle reflection light component (Lrsp) 28 of the specular reflection geometry are calculated out (at S19 in FIG. 13). In other words, a Torrance-Sparrow model calculation value LrTSs of the surface reflection light component Lrss and a Torrance-Sparrow model calculation value LrTSp of colorant material particle reflection light component Lrsp are calculated. The variable σ of the density distribution for use in calculating the colorant material particle reflection light component (Lrsp) is the variable σp of evenness in density of the sample. This variable is inputted, in advance, via the operation input section 202. The variable σ of the surface coarseness for use in calculating the surface reflection light component (Lrss) is the variable σs of the surface coarseness of the sample. This variable is also inputted, in advance, via the operation input section 202.

Then, fitting process is carried out in which the surface reflection light component (Lrs) and the colorant material particle reflection light component (Lrsp) of one specular reflection geometry are fitted to the Torrance-Sparrow model, thereby to obtain the surface reflection light component (Lrs) and the colorant material particle reflection light component (Lrsp) in each specular reflection geometry (at S20 in FIG. 13). In other words, the shape-parameter calculating section 215 finds allocation from the foregoing model calculation values LrTSs and LrTSp thereby to obtain, based on the allocation, the surface reflection light component Lrss and the colorant material particle reflection light component Lrsp in each specular reflection geometry.

Figure 18:
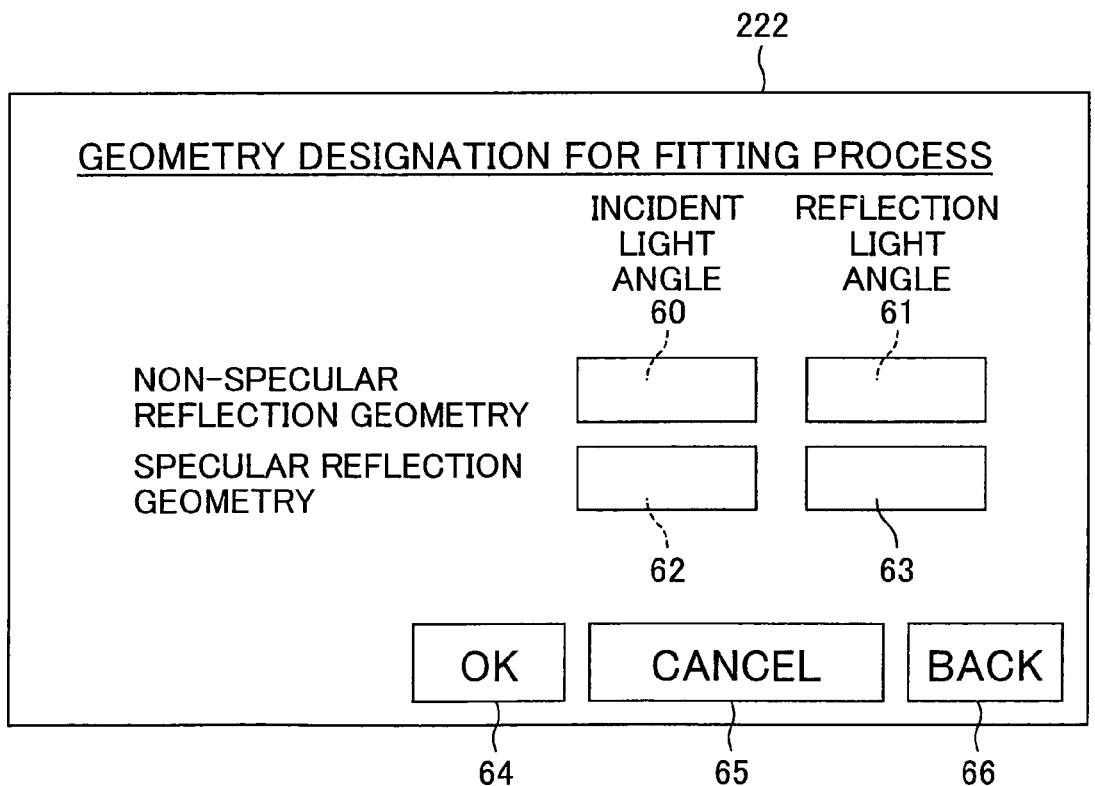
FIG. 18 is a diagram schematically illustrating another example of a data input screen displayed on a display section of the specular glossiness simulation device as illustrated in FIG. 16.

FIG. 18 gives an example of the data input screen displayed on the display section 222, for the input of the information regarding the selected non-specular reflection geometry and specular reflection geometry. The present invention is not limited to the arrangement exemplified here in which the information of the non-specular reflection geometry and specular reflection geometry are inputted on the same screen. The data input screen illustrated in FIG. 18 is provided with an input item 60 for the incident light angle of the non-specular reflection geometry and an input item 61 of the refection angle of the non-specular reflection geometry, an input item 62 for the incident light angle of the specular reflection geometry and an input item 63 of the refection angle of the specular reflection geometry. Further, the data input screen illustrated in FIG. 18 is provided with an OK key 64, a cancel key 65, and a back key 66, which are touch-panel keys. When the cancel key 65 is pressed, the measurement mode is terminated with the data input screen inactivated. When the back key 66 is pressed, the display screen goes back to the data input screen illustrated in FIG. 17.

By the input items regarding the non-specular reflection geometry, the geometry for the fitting process for the diffuse reflection light component (Lrd) is designated. By the input items regarding the specular reflection geometry, the geometry for the fitting process for the surface reflection light component (Lrss) is designated. The incident light angle and reflection light angle of the non-specular reflection geometry should be designated separately. However, the incident light angle and reflection light angle of the specular reflection geometry are identical, therefore, a value inputted in one of the input items (e.g., the input item 62 for the incident light angle) is also displayed in the other one of the input items (e.g., the input item 63 for the reflection light angle). That is, it is only required to input the value either one of the input items for the specular reflection geometry.

After the input of the information regarding the non-specular reflection geometry and specular reflection geometry, and the sample on which the toner image is formed is placed on the gonio data measuring section 204, the OK key 64 is pressed, so that the processes of S14 to S20 are carried out (S15 and S17 are omitted since these steps are carried out in advance by using a separate device). Thereby, the lower layer reflection light component (Lru), diffuse reflection light component (Lrd), the surface reflection light component (Lrss), and the colorant material particle reflection light component (Lrsp) 28 in each geometry is calculated out. These values are then stored in the second memory 252 in association with the geometries.

The following will describe, in a specific manner, how the internal reflection light components (Lrd) of all geometries are calculated.

First, in the display section 222 that displays a data input screen shown in FIG. 18, the data of an incident light angle and a light reflection angle of the input non-specular reflection geometry is supplied to a Lrd calculating section (not illustrated), and is then supplied to the gonio data measuring section 204. In the gonio data measuring section 204, the gonio data (Lra) of the geometry thus input is measured, and the data as a result of the measurement is supplied to the Lrd calculating section.

In the Lrd calculating section, the data of the lower layer reflection light component (Lru) calculated using the same geometry is selected and retrieved from the second memory 252, and this lower layer reflection light component (Lru) is subtracted from the gonio data (Lra). Further, in this instance, the diffuse reflection light component (Lrd) is approximated to 0 and the remaining reflection light components are regarded as the internal reflection light component (Lrd).

The data of the diffuse reflection light component (Lrd) calculated by the Lrd calculating section is supplied to the Lrd fitting process section (not illustrated). In the Lrd fitting process section, the surface reflection light component thus supplied is subjected to fitting with the Oren-Nayar model. With this, the internal reflection light components (Lrs) of all geometries are calculated, and this data is stored in the second memory s52.

The following will specifically describe how the reflection light components (Lrsp) of colorant material particles and the surface reflection light components (Lrss), of all specular reflection geometries, are calculated.

First, in the display section 222 that displays a data input screen shown in FIG. 18, the data of an incident light angle and a light reflection angle of the input specular reflection geometry is supplied to an Lrss calculating section and a Lrsp calculating section (both not illustrated), and the data is then supplied to the gonio data measuring section 204. In the gonio data measuring section 204, the gonio data (Lrb) of the geometry thus input is measured and the data as a result of the measurement is supplied to the Lrss calculating section and the Lrsp calculating section.

In the Lrss calculating section, the data of the lower layer reflection light component (Lru) calculated using the same geometry and the data of the diffuse reflection light component (Lrd) calculated using the same geometry are selected and retrieved from the second memory 252. The lower layer reflection light component (Lru) and the diffuse reflection light component (Lrd) are subtracted from the gonio data (Lrb), and a model calculation value (LrTSs) is calculated using the Torrance-Sparrow model.

In the Lrsp calculating section, the data of the lower layer reflection light component (Lru) calculated using the same geometry and the data of the diffuse reflection light component (Lrd) calculated by the same geometry are selected and retrieved from the second memory 252. The lower layer reflection light component (Lru) and the diffuse reflection light component (Lrd) are subtracted from the gonio data (Lrb), and a model calculation value (LrTSp) is calculated using the Torrance-Sparrow model.

In the configuration parameter calculating section 215, a configuration parameter k that satisfies Lrb=k×LrTSs+(1−k)×LrTSp is calculated in reference to the model calculation values (LrTSs) and (LrTSp) thus calculated and the gonio data (Lrb), and a distribution ratio between the surface reflection light component (Lrss) and the reflection light component Lrsp of the colorant material particles is determined. With this, the surface reflection light component (Lrss) and the reflection light component (Lrsp) of the colorant material particles, of one specular reflection geometry, are determined.

The data of the surface reflection light component (Lrss) and the data of the reflection light component (Lrsp) of colorant material particles, which have been calculated as above, are sent to a Lrss fitting process section (not illustrated) and a Lrsp fitting process section (not illustrated), respectively. In the Lrss fitting process section and the Lrsp fitting process section, the surface reflection light component (Lrss) and reflection light component (Lrsp) thus supplied are subjected to the fitting with the Torrance-Sparrow model. With this, the surface reflection light components (Lrss) and the reflection light components (Lrsp) for all of the specular reflection geometry are calculated, and the data as a result of the calculation is stored in the second memory 252.

As a result of the processes above, the second memory 252 stores the lower layer reflection light components (Lru), the diffuse reflection light components (Lrd), and the reflection light components (Lrsp) of the colorant material particle, which are of all of the geometries. These components in the second memory 252 are associated with the corresponding specular reflection geometries. The specular reflection light component calculating section 214 adds up the reflection light components of the same specular reflection geometry. With this, the specular reflection light components Lr of all specular reflection geometries are obtained (S21 in FIG. 13).

Figure 19:
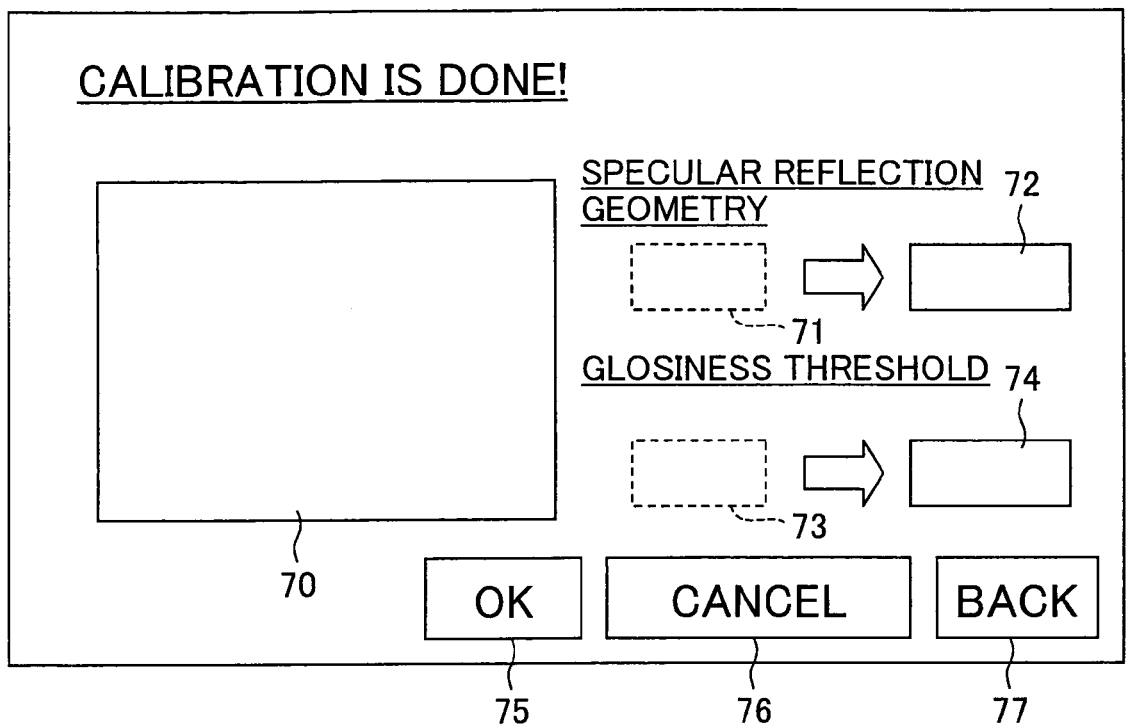
FIG. 19 is a diagram schematically illustrating an example of a screen displaying a result of a measurement, the result being displayed on a display section of the specular glossiness simulation device as illustrated in FIG. 16.

The data of the measurement result of the specular reflection light components Lr obtained above is sent to the operation input section 202, and displayed on the display section 222. FIG. 19 shows an example of the measurement result displayed on the display section 222.

As shown in FIG. 19, after the measurement of the specular reflection light components Lr, the display section 222 displays: a graph 70 of the specular reflection light components Lr; an input item 71 for the specular reflection geometry; a calculation result 72 of the specular reflection light component Lr of the geometry inputted in the input item 71; an input item 73 for the gloss threshold; a calculation result 74 of the specular reflection geometry that indicates the threshold inputted in the input item 73; an OK button 75; a cancel button 76; and a back button 77. The graph 70 of the specular reflection light components Lr shows the list of all specular reflection light components Lr, in a case where the incident light angles are in the range of 10° and 80°. It is therefore possible to see to what extent a sample specular reflection light component is dependent on the angle. The results shown in the graph 70 are calculated in the specular reflection light component calculating section 214 by adding up the lower layer reflection light components Lru, diffuse reflection light components Lrd, surface reflection light components Lrss, and reflection light components Lrsp of the colorant material particle, of all specular reflection geometries stored in the second memory 252.

In the specular gloss simulation device 200, an arbitrary angle is input in the input item 71 of the specular reflection geometry shown in FIG. 19, and the OK button 75 is pushed. With this, the value of the specular reflection light component of the angle thus input is, obtained. The calculated value of this case is equal to a point on the graph 70 of the specular reflection light components Lr.

In the meanwhile, a desired specular reflection light component (corresponding to the luminance, here) is inputted in the input item 73 for the gloss threshold and the OK button 75 is pushed. With this, an angle corresponding to the specular reflection light component thus input is displayed as the calculation result 74. The calculation result proves that angles corresponding to the specular reflection light components higher than the component thus inputted are greater than the displayed angle. In other words, the specular gloss simulation device 200 of the present embodiment makes it possible to calculate the specular reflection light components of all specular reflection geometries. Therefore, by varying the specular reflection geometry (incident and light reflection angles), it is possible to confirm in which case the specular reflection light component exceeds a predetermined value. This can be effectively used as a novel valuation standard for the gloss.

If the cancel button 76 in the result screen shown in FIG. 19 is pushed, the result screen finishes and the measurement mode is compulsorily terminated. If the back button 77 is pushed, the data input screen shown in FIG. 18 is shown again.

In a case where the specular reflection light component simulated as above is converted to the gloss in conformity to Japanese Industrial Standards, the gloss is figured out in such a manner that a relative value is calculated based on a value in the case of a standard plate (glass plate with a refractive index of 1.567) specified as a standard sample.

The specular gloss simulation device 200 may be realized using a computer system. The computer system may be similar to the computer system 300 (see FIG. 12) of Embodiment 1.

As in the case of Embodiment 1, the processing steps performed by the calculating section 201 of the specular gloss simulation device 200 of the present embodiment and the processing steps performed by the sections 21-215 in the calculating section 201 are realized by causing computing means such as a CPU to execute a program stored in storage means such as ROM (Read Only Memory) and RAM, so as to control the input means such as a keyboard, output means such as a display, or a communication means such as an interface circuit. On this account, the functions and processes of the specular gloss simulation device 200 can be realized only by causing the computer having the aforesaid means to read a storage medium storing the program and execute the program. If the program is stored in a removable storage medium, the aforesaid functions and processes can be realized on any computer.

Third Embodiment

Referring to FIG. 24 through FIG. 28, the following will describe a Third Embodiment of the present invention. The foregoing First Embodiment described the specular gloss simulation method that is applicable regardless of the size of the colorant material particles in the dye ink, pigment ink, or toner used for the colorant material layer of the sample. However, as in the Second Embodiment, the present embodiment describes a specular gloss simulation method and specular gloss simulation device for more accurately calculating specular gloss components of the sample when the colorant material particles contained in the colorant material layer have a relatively large diameter (i.e., when the colorant material particles are pigments such as pigment ink or toner). Examples of such pigments include pigment ink and toner. Note that, the present embodiment differs from the foregoing First and Second Embodiments in that one of the specular reflection geometries and two of the non-specular reflection geometries are selected as the given geometry, and gonio data of these geometries are measured.

First, the specular gloss simulation device of the present embodiment is described in regard to the dichromatic reflection (BRDF) model theory used for the simulation of specular gloss of a sample. Here, description of the BRDF model will be given through the case where it is used to calculate reflection light components of a sample having the bilayer structure of the base material and the colorant material layer in which toner (pigment) is contained as colorant material particles.

FIG. 14 schematizes how the reflection light components of the bilayer sample are split into individual components. As illustrated in FIG. 14, a sample 23 includes an upper layer portion 13 constituting a toner image (colorant material layer), and a lower layer portion 33 constituting a base material such as paper or a transparent film. According to the dichromatic reflection (BRDF) model theory, the reflection light components of the light from a light source 6 include: a surface reflection light component (Lrss) 27 and an internal reflection light component 35, both from the upper layer portion 34, and a surface reflection light component 30 and an internal reflection light component 31, both from the lower layer portion 33. The composite light of these components becomes the reflected light from the sample 23. In the present embodiment, the internal reflection light component 35 from the upper layer portion 34 can be further divided into a reflection light component (Lrsp) 28 directly reflected by the colorant material particles, and a diffuse reflection light component (Lrd) 29 produced by scattering of light between the colorant material particles. In order to calculate the reflected light components 27 through 31 by the BRDF model, more than one unmeasurable parameter needs to be estimated.

However, since the measurement of the internal reflection light component 31 reflected from the lower layer portion 33 is difficult, the present invention combines the internal reflection light component 31 with the surface reflection light component 30 also from the lower layer portion 33, and uses the sum of these reflection light components as a lower layer reflection light component (Lru) 32. By calculating the lower layer reflection light component 32 based on measurement data obtained only from the lower layer portion 33, a specular reflection light amount can be accurately calculated for a wide variety of samples images according to the BRDF model. By thus calculating the lower layer reflection light component 32 with the surface reflection light component 27, the reflection light component 28 of the colorant material particles, and the diffuse reflection light component 29 from the upper layer portion 34, an accurate specular reflection light amount can be obtained.

As the BRDF model effective as the mathematical models for calculating the respective reflection light components, the present invention can use the (1) Ward Model, (2) Phong Model, (3) Oren-Nayar Model, and (4) Torrance-Sparrow Model, which are described above in the First Embodiment.

Of these mathematical models, the Ward model and the Phong model have been proposed based on isotropic scattering of light, whereas the Oren-Nayar model and the Torrance-Sparrow model are based on non-isotropic scattering of light. In the present embodiment, the Torrance-Sparrow model is adopted as the mathematical model for calculating the surface reflection light component 27 and the reflection light component 28 of the colorant material particles, and the Oren-Nayar model is adopted as the mathematical model for calculating the diffuse reflection light component 29 produced by scattering of light between the colorant material particles. This is because more accurate values can be obtained when non-isotropic scattering of light is taken into consideration, though it complicates the equations.

FIG. 5 represents a geometric arrangement according to the BRDF model. FIG. 6 represents geometric definitions of object surfaces according to the BRDF model.

In calculating the diffuse reflection light component Lrd using the Oren-Nayar model, mathematical value LrON is calculated first according to Equation (1) below.

$$LrON = \frac{\sigma}{\pi} E0\cos\theta i[C1(\sigma) + \cos(\phi r - \phi i)C2(\alpha;\beta;\phi r - \phi i;\sigma)\tan\beta) + \quad (1)$$

$$(1 - |\cos(\phi r - \phi i)|)C3(\alpha;\beta;\sigma)\tan\left(\frac{\alpha+\beta}{2}\right) +$$

$$0.17\frac{\rho^2}{\pi} E0\cos\theta i \frac{\sigma^2}{\sigma^2 + 0.13}\left[1 - \cos(\phi r - \phi i)\left(\frac{2\beta}{\pi}\right)^2\right]$$

$$C1 = 1 - 0.5\frac{\sigma^2}{\sigma^2 + 0.33}$$

$$C2 = \begin{cases} 0.45\frac{\sigma^2}{\sigma^2 + 0.09}\sin\alpha & (\text{if } \cos(\phi r - \phi i) \geq 0) \\ 0.45\frac{\sigma^2}{\sigma^2 + 0.09}\sin\alpha & \left(\sin\alpha - \left(\frac{2\beta}{\pi}\right)^3\right) & (\text{if not}) \end{cases}$$

$$C3 = 0.125\left(\frac{\sigma^2}{\sigma^2 + 0.09}\right)\left(\frac{4\alpha\beta}{\pi^2}\right)^2$$

In Equation (1), $\theta i$ is the zenith angle in the light source direction, $\phi i$ is the azimuth angle in the light source direction, $\theta r$ is the zenith angle in the light reflection direction, $\phi r$ is the azimuth angle in the light reflection direction, $\sigma$ is the roughness variable of the surface profile, E0 is the radiant luminance incident on the sample, $\rho$ is the refractive index of the microscopic surface of the sample surface, $\alpha = \max[\theta r, \theta i]$, and $\beta = \min[\theta r, \theta i]$ (see FIG. 5, FIG. 6). Note that, the mathematical formula used to calculate LrON in this embodiment is the same as those used in the First and Second Embodiments.

In calculating the surface reflection light component Lrss and the reflection light component Lrsp of the colorant material particles according to the Torrance-Sparrow model, mathematical value LrTS (LrTSs and LrTSp) is calculated first according to Equation (2) below.

$$LrTS = E0\frac{FGAF}{\cos\theta r\cos\theta a}ce^{-\frac{\theta a^2}{2\sigma^2}} \quad (2)$$

$$GAF = \max\left[0, \text{Min}\left[1, \frac{2<s,n><a,n>}{<s,a>}, \frac{2<v,n><a,n>}{<v,a>}\right]\right]$$

$$c = \int_{\theta a=0}^{\frac{\pi}{2}}\int_{\phi a=0}^{2\pi} e^{-\frac{\theta a^2}{2\sigma^2}}\sin\theta a d\phi a d\theta a$$

In Equation (2), F is the Fresnel reflection index, n is the normal vector of the sample 3, s is the vector of the light source direction, v is the vector of the light reflection direction, a is the bisector vector of s and v, $\theta r$ is the zenith angle of the light reflection direction, $\theta a$ is the zenith angle of vector a, $\phi a$ is the azimuth angle of vector a, $\sigma$ is the roughness variable of the surface profile, and E0 is the radiant luminance incident on the sample. Further, in Equation (2), $<x, y>$ (x, y are arbitrary numbers) is the inner products of the vectors (see FIG. 5, FIG. 6). Note that, the mathematical formula used to calculate LrTS in this embodiment is the same as those used in the First and Second Embodiments.

Subsequently, referring to the flow chart in FIG. 24, a method will be described by which the amount of specular reflection light is calculated for each geometry from a measured value of luminance in a predetermined geometry using the above technique.

First, to calculate the lower layer reflection light component Lru, the transmittance of only the upper layer portion (toner image) 34 of a sample for which the specular reflection light component is to be calculated is calculated (step S21). The measurement geometry here includes a light source, a sample, and a light receiver positioned along a straight line. In such a geometry, the light source shines right above the sample. That light which is received by the light receiver located right under the sample is measured with a transmission density meter as light having transmitted the sample. Here, the transmission density Dt for only the upper layer portion 34 is obtained by making measurements on a sample with a toner image formed thereon (a sample made up of the upper layer portion 34 and the lower layer portion 33) and a sample made of only the lower layer portion (paper) 33 with a transmission density meter and calculating a differential between the former and the latter. A transmittance Tt for only the upper layer portion 34 (in other words, the toner image) is given by Tt=10^(−Dt).

Throughout the following steps, the refractive index (literature value) of resin which is a main component of toner is used as the refractive index of the upper layer portion (toner image) 34.

Next, a sample with no upper layer portion 34, that is, a sample with only the lower layer portion 33 (in the present embodiment, paper or transparent film still carrying no toner image formed thereon) is prepared. With the light source incidence direction and the light reflection direction of the sample with only the lower layer portion 33 being resolved at high resolution, gonio data is then measured (step S22). Here, CIE 1976 L*a*b* (CIE: Commission International de l'Eclairage. L* is a lightness, and a* indicates redness-greenness and b* indicates yellowness-blueness) color space is used for the measurement. Therefore, the value of L* is employed as the gonio data. There are no particular limitations on angle resolution in the process. In the present embodiment, the resolution is 1° because typical measuring devices have a maximum angle resolution of 1°. In other words, in the present embodiment, the gonio data is measured for all geometries in which the angles shown in FIG. 5 are shifted by 1°. To calculate the specular reflection light component more precisely, the angle resolution is preferably 1° or less.

The lower layer reflection light component Lru is calculated for each geometry from this data (step S23). FIG. 15 is a diagram schematically illustrating a refraction phenomenon of light and attenuation of an amount of light, which are taken into consideration when the lower layer reflection light component Lru is calculated. Light incident to the sample at an incident light angle $\theta i$ refracts at the interface between the air layer 36 and the upper layer portion 34. This refraction phenomenon obeys Fresnel's theory. The angle θt after the refraction is given by Fresnel's law (n1×sin θi=n2×sin θt, where n1 is the refractive index of a pre-incidence medium, and n2 is the refractive index of a post-incidence medium). Light is attenuated at the interface due to the refraction as it passes through the toner layer. The Fresnel transmittance Tn is given by equation (3):

$$Tn = \left[\left(\frac{n2\cos\theta t}{n1\cos\theta i}\right)\left(\frac{2n1\cos\theta i}{n2\cos\theta i + n1\cos\theta t}\right)^2 + \left(\frac{n2\cos\theta t}{n1\cos\theta i}\right)\left(\frac{2n1\cos\theta i}{n1\cos\theta i + n2\cos\theta t}\right)^2\right]/2 \quad (3)$$

As light passes through the upper layer portion 34, the light is attenuated by the upper layer portion 34 before reaching the lower layer portion 33. The attenuation obeys the Beer-Lambert law (-logT=a×d, where a is the absorption coefficient of a colorant material layer, d is the thickness of the colorant material layer, and T is the transmittance). The length of the optical path in the upper layer portion 34 traveled by the light before reaching the lower layer portion 33 changes with the incident light angle. The apparent transmittance Tt' in accordance with the changes in the length of the optical path is given by -logTt'=a×(d/cos θi). Light attenuation is evaluated in terms of the apparent transmittance.

From the above description, the amount of incident light reaching the lower layer portion 33 is calculated by evaluating the attenuation of the amount of light from the apparent transmittance Tt' in accordance with the Fresnel transmittance Tn and the changes in the length of the optical path. The calculation also takes into consideration the changes of the incident light angle of the light to the lower layer portion 33 caused by the refraction. A similar optical phenomenon occurs when the reflection from the lower layer portion 33 travels back to the air layer. Therefore, the lower layer reflection light component Lru is calculated by calculating from the gonio data of the sample with only the lower layer portion (paper) measured in S22 for all incident light angles and light reflection angles with the two refractions and an attenuation of light (see FIG. 15) taken into consideration. If the incident light angle θt after the refraction has decimal places, the angle is interpolated by proration from the preceding and succeeding angle values. There are no particular limitations on angle resolution in the process. Here, the resolution is 1° because the measuring device has a maximum angle resolution of 1°. To calculate the specular reflection light component more precisely, the angle resolution is preferably 1° or less.

Next, the luminance value Lra (L* of CIE 1976 L*a*b*) of the sample is measured in one certain geometry which contains almost zero surface reflection light component (step S24). This geometry is termed a first non-specular reflection geometry. Generally, the more the geometry differs from specular reflection, the smaller the surface reflection light component. The first non-specular reflection geometry selected here therefore preferably has a large light source incident light angle and includes a light source incidence position and a light receiving position in close proximity. For the present embodiment, an exemplary first non-specular reflection geometry is selected where the light source incident light angle θi is 45° (φi=0°) and the light reflection angle θr is −60° (φr =0°).

Further, in one certain geometry which contains a little surface reflection light component, the luminance value Lrc (L* of CIE 1976 L*a*b*) of the sample is measured (step S25). This geometry is termed a second non-specular reflection geometry. The second non-specular reflection geometry selected here is preferably between the first non-specular reflection geometry and the specular reflection geometry, not very similar to any of the two geometries, and substantially intermediate between the two. For the present embodiment, an exemplary second non-specular reflection geometry is selected where the light source incident light angle θi is 45° (φi=0°) and the light reflection angle θr is 0° (φr=0°).

Then, the luminance value Lrb (L* of CIE 1976 L*a*b*) of the sample is measured in one certain specular reflection geometry (step S26). This geometry is termed the specular reflection geometry. The specular reflection geometry selected here is such that the light source incident light angle is 45° (φi=0°) and the light reflection angle is 45° (φr=180°). The present invention is not limited to these angles.

Next, the density distribution of the toner image sample is measured, and its roughness variable σp is calculated from the measured value (step S27). Subsequently, the surface shape of the sample is measured, and its roughness variable σs is calculated from the measured value (step S28). A specific method for the calculation of the roughness variable σs of the surface shape and the roughness variable σp will be detailed later.

Subsequently, the luminance value Lra measured in S24, the luminance value Lrc measured in S25, and the luminance value Lrb measured in S26 is subjected to fitting using a Torrance-Sparrow model and an Oren-Nayar model (step S29). This fitting process is now detailed in the following.

Each of Lra, Lrb, and Lrc above is a sum of the surface reflection light component Lrss, the colorant material particle reflection light component Lrsp, the diffuse reflection light component Lrd, and the lower layer reflection light component Lru. Therefore, the components obtained by subtracting Lru from Lra, Lrb, or Lrc each correspond to the sum of Lrss, Lrsp, and Lrd (in other words, the upper layer reflection light component).

Here, to determine the allocation ratio of the surface reflection light component, the colorant material particle reflection light component, and the diffuse reflection light component in the upper layer reflection light component (in other words, the sum of Lrss, Lrsp, and Lrd), parameters kss, ksp, and kd are introduced. Note that $$kss + ksp + kd = 1 \quad (4)$$

In this case, using a Torrance-Sparrow model and an Oren-Nayar model, the upper layer reflection light component is given by equation (5):

$$Lrss + Lrsp + Lrd = kss \times LrTSs + ksp \times LrTSp + kd \times LrON \quad (5),$$

where LrTSs is a Torrance-Sparrow model calculated value for the surface reflection light component Lrss, LrTSp is a Torrance-Sparrow model calculated value for the colorant material particle reflection light component Lrsp, and LrON is an Oren-Nayar model calculated value for the diffuse reflection light component Lrd.

The roughness variable σ for the Torrance-Sparrow model used in the process is a parameter defining the range of the reflection light component in the physical model. Therefore, for the surface reflection light component Lrss, the roughness variable σs of the surface shape obtained in S28 is employed. For the colorant material particle reflection light component Lrsp, the roughness variable σp of the density distribution obtained in S27 is employed. In addition, the roughness variable σp of the density distribution obtained in S27 is employed as the roughness variable σ for the Oren-Nayar model. E0 (see FIG. 5) is irradiance incident to the sample. Here, since the measured value space is CIE 1976 L*a*b* space, and L* is employed, E0=100π. F is set to 1 to obtain surface reflection in the specular reflection geometry.

Then, Lru in the first non-specular geometry, calculated in step S23, is subtracted from the measured Lra. The remaining component (in other words, Lra−Lru) is substituted to the left side of equation (5). θi, θr, φi, and φr corresponding to the first non-specular geometry are substituted to model equations on the right side to generate equation (6).

Similarly, Lru in the second non-specular geometry, calculated in step S23, is subtracted from the measured Lrc. The remaining component (in other words, Lrc−Lru) is substituted to the left side of equation (5). θi, θr, φi, and φr corresponding to the second non-specular geometry are substituted to model equations on the right side to generate equation (7).

Further, Lru in the specular geometry, calculated in step S23, is subtracted from the measured Lrb. The remaining component (in other words, Lrb−Lru) is substituted to the left side of equation (5). θi, θr, φi, and φr corresponding to the specular geometry are substituted to model equations on the right side to generate equation (8).

Then, by solving equations (6) to (8), and (4), the unknown parameter ρ in the Oren-Nayar model and the parameter kss, ksp, kd indicating the allocation ratio are determined (step S29). The reflectance ρ of the small plane on the sample surface is never negative in the physical model; only positive values are employed (ρ>0).

The parameter ρ in Oren-Nayar model and the parameters kss, ksp, kd indicating the allocation ratio, which are all determined as above, are used to calculate the surface reflection light component Lrss, the colorant material particle reflection light component Lrsp, and the diffuse reflection light component Lrd in each geometry (step S30).

To describe it in more detail, $$Lrss = kss \times LrTSs$$

$$Lrsp = ksp \times LrTSp$$

$$Lrd = kd \times LrON$$

By substituting θi, θr, φi, and φr corresponding to each geometry to the model calculation equations in these equations, the upper layer surface reflection light component Lrss, the colorant material particle reflection light component Lrsp, and the diffuse reflection light component Lrd in each geometry are calculated.

Then, the lower layer reflection light component Lru obtained in step 23 and the upper layer surface reflection light component Lrss, the colorant material particle reflection light component Lrsp, and the diffuse reflection light component Lrd obtained in step S30, all in the same geometry, are added up to obtain the specular reflection light component (amount of specular reflection light) Lr. The specular reflection light component Lr is obtained for each geometry (step S31).

In embodiment 2 above, Lrss and Lrsp were both approximated to 0 in the calculation of the diffuse reflection light component Lrd (step S16). The present embodiment involves no such approximation. Accordingly, in the present embodiment, the reflection light components and the amount of the specular reflection light are obtained more precisely.

The aforementioned specular gloss simulation method takes every kind of image (low gloss image, low density image, etc.) into consideration, and therefore assumes separating a sample on which measurement is to be made into an upper layer portion and an lower layer portion. However, special measurement samples (high density, high gloss samples) may be treated differently. The specular reflection light component Lr may be calculated using only the reflection light component from only the upper layer portion (the surface reflection light component Lrss, the colorant material particle reflection light component Lrsp, and the diffuse reflection light component Lrd). This is because in this case, the lower layer reflection light component Lru is too small to affect the specular reflection light component Lr.

In addition, in the present embodiment, to calculate the specular reflection light component Lr for each geometry in step S31, the gonio data is measured for each geometry in step S22. This is however by no means limiting the present invention. For example, if the specular reflection light component is to be calculated only for one certain desired geometry, it is sufficient to measure in step S22 the gonio data for geometries corresponding to the desired geometry, the first non-specular reflection geometry, the second non-specular reflection geometry, and the specular reflection geometry. The "geometries corresponding to the desired geometry, the first non-specular reflection geometry, the second non-specular reflection geometry, and the specular reflection geometry" are those with the refractive index of the upper layer portion 34 taken into consideration. To describe in more detail, those geometries are such a reflection angle at which incident light to the light receiving section reflects from the lower layer portion 33 and such that the incident light angle at which the beam actually enters the lower layer portion 33 when the reflection of a beam shone onto the sample is measured with a light receiving section in the desired geometry, the first non-specular geometry, the second non-specular geometry, and the specular geometry. In addition, it is sufficient in this case to calculate in the reflection light components in a desired geometry also in steps S30, S31. This is similarly true with embodiments 1 and 2 above.

In the aforementioned specular gloss simulation method, steps S21 to S23 are a lower layer reflection light component forming step, steps S24 to S30 are an upper layer reflection light component forming step, and step S31 is a specular reflection light amount calculating step.

Next, an arrangement of a specular gloss simulation device according to the present invention is described below. The specular gloss simulation device according to the present embodiment calculates out the specular reflection light component of each specular reflection geometry by performing the process illustrated in the flowchart of FIG. 24. From the specular reflection light components thus obtained, the specular gloss simulation device simulates the specular gloss. In FIG. 25, an arrangement of a specular gloss simulation device 400 according to the present invention is illustrated.

As illustrated in FIG. 25, the specular gloss simulation device 400 is provided mainly with a calculating section 401, an operation input section 402, a storage 403, and a gonio data measuring section 404.

The calculating section 401 calculates out a specular reflection light component from (a) data of refractive index and transmittance, the variable of the density distribution on the sample, the variable of the surface coarseness of the sample (which has been inputted via the operation input section 402) of the upper portion (toner image) 34, (b) the first non-specular reflection geometry/the second non-specular reflection geometry/specular reflection geometry/being designated via the operation input section 402, and (c) gonio data being measured by the gonio data measuring section 404.

The calculating section 401 is provided with a lower layer reflection light component calculating section (lower layer reflection light component creating section) 411, an upper layer reflection light component calculating section (upper layer reflection light component creating section) 412, and a specular reflection light component calculating section (specular reflection light amount calculating section) 414. The lower layer reflection light component calculating section 411 is used for calculating a lower layer reflection light components (Lru). The internal reflection light component creating section 412 is used for calculating a diffuse reflection light component (Lrd), a surface reflection light component (Lrss), and a colorant material particle reflection light component (Lrsp). The specular reflection light component calculating section (specular reflection light amount calculating section) 414 is used for calculating a specular reflection light component (Lr).

The lower layer reflection light component calculating section 411 calculates the lower layer reflection light component (Lru) in each geometry from the above pieces of information and the gonio data of the lower layer portion only which are inputted via the operation input section 402, the gonio data being measured by using the gonio data measuring section 404.

The specular reflection light component calculating section 414 adds up the reflection light components of the same specular reflection geometry, which are calculated by using the lower layer reflection light component calculating section 411 and the upper layer reflection light component calculating section 412, thereby to calculate out the specular reflection light component in each specular reflection geometry. Note that, in the present embodiment, the specular reflection light component calculating section 414 calculates the specular reflection light component in each geometry.

Based on the measured gonio data of the lower layer portion only in one specular geometry and two non-specular geometries, the upper layer reflection light component calculating section 412 calculates the diffuse reflection light component (Lrd), the surface reflection light component (Lrss), and the colorant material particle reflection light component (Lrsp) of each geometry. More specifically, the upper layer reflection light component calculating section 412 includes a shape-parameter calculating section (parameter calculating section) 415 and a reflection light component calculating section 416. The shape-parameter calculating section 415 is used for calculating (i) unknown parameter $\rho$ in the Oren-Nayar model, and (ii) calculates Kss, Ksp, and Kd each of which indicating allocation of the diffuse reflection light component, the surface reflection light component, and the colorant material particle reflection light component, from a measured gonio data in one specular reflection geometry and two non-specular reflection geometries. The reflection light component calculating section calculates the diffuse reflection light component (Lrd), the surface reflection light component (Lrss), and the colorant material particle reflection light component (Lrsp) in each geometries, by using the parameter $\rho$, Kss, Ksp, and Kd.

The operation input section 402 is used for inputting various numerical values necessary for the calculation of the specular reflection light component, and for displaying a result of calculation performed by the calculating section 401. The operation input section 402 includes operation keys 421 for inputting numerical values and/or the like, and a display section 422 for displaying items such as information inputted via the operation keys 421, the result of calculation, and/or the like.

The storage section 403 is used for storing therein a result of the measurement performed by the gonio data measuring section 404, and the result of the calculation performed by the calculating section 401. The storage section 403 is provided with a first memory 451 (LUT 1) and a second memory 452 (LUT 2). The first memory 451 is for storing therein gonio data of a sample measured by the deviation angle measuring section 404, the sample having a lower layer portion (paper) 33 only. The second memory 452 is for storing therein each component light component calculated out by the calculating section 401.

The gonio data measuring section 404 measures the gonio data of the sample having the lower portion (paper) 33 only, and the gonio data of the sample having the two-layered structure, that is, having the lower layer portion 33 and the upper layer portion (toner image) 34. The gonio data measuring section 204 has an angular resolution of 1°, by which the gonio data measuring section 204 is able to measure the gonio data per degree.

For simulating the specular glossiness by using the specular gloss simulation device 200, the gonio data of the sample having the lower portion (paper) 33 only is measured per degree, meanwhile for the sample having the lower layer portion 33 and the upper layer portion 34, it is only required to measure the gonio data of one specular reflection geometry and one non-specular reflection geometry.

Next, how to simulate the specular gloss in each specular reflection geometry of a sample by using the specular gloss simulation device 400 is described below, referring to FIGS. 24 and 25.

Figure 24:
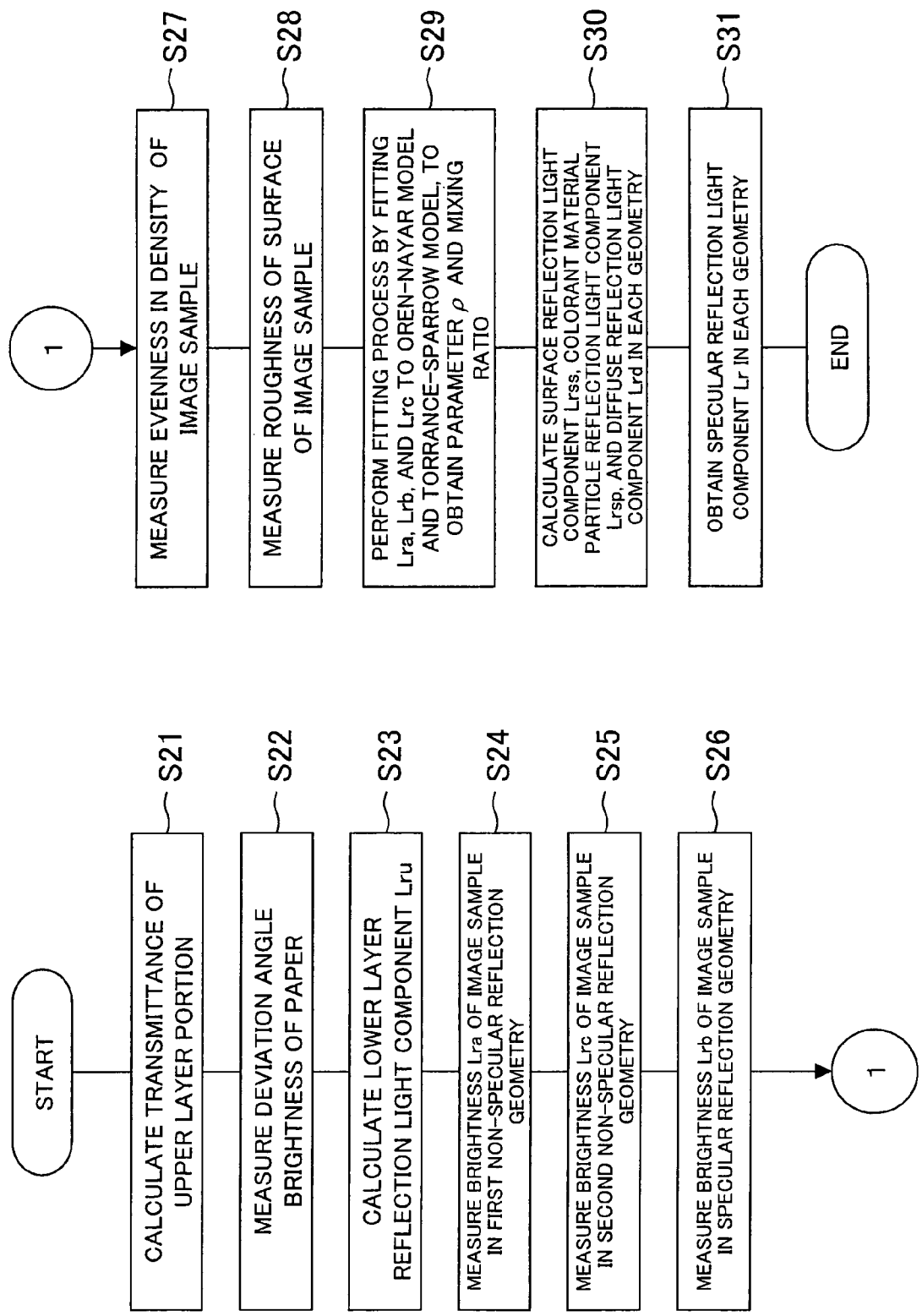
FIG. 24 is a flow chart of a process for calculating a specular reflection light component in each geometry from a measured value of luminance in a predetermined geometry in the embodiment 3.
Figure 25:
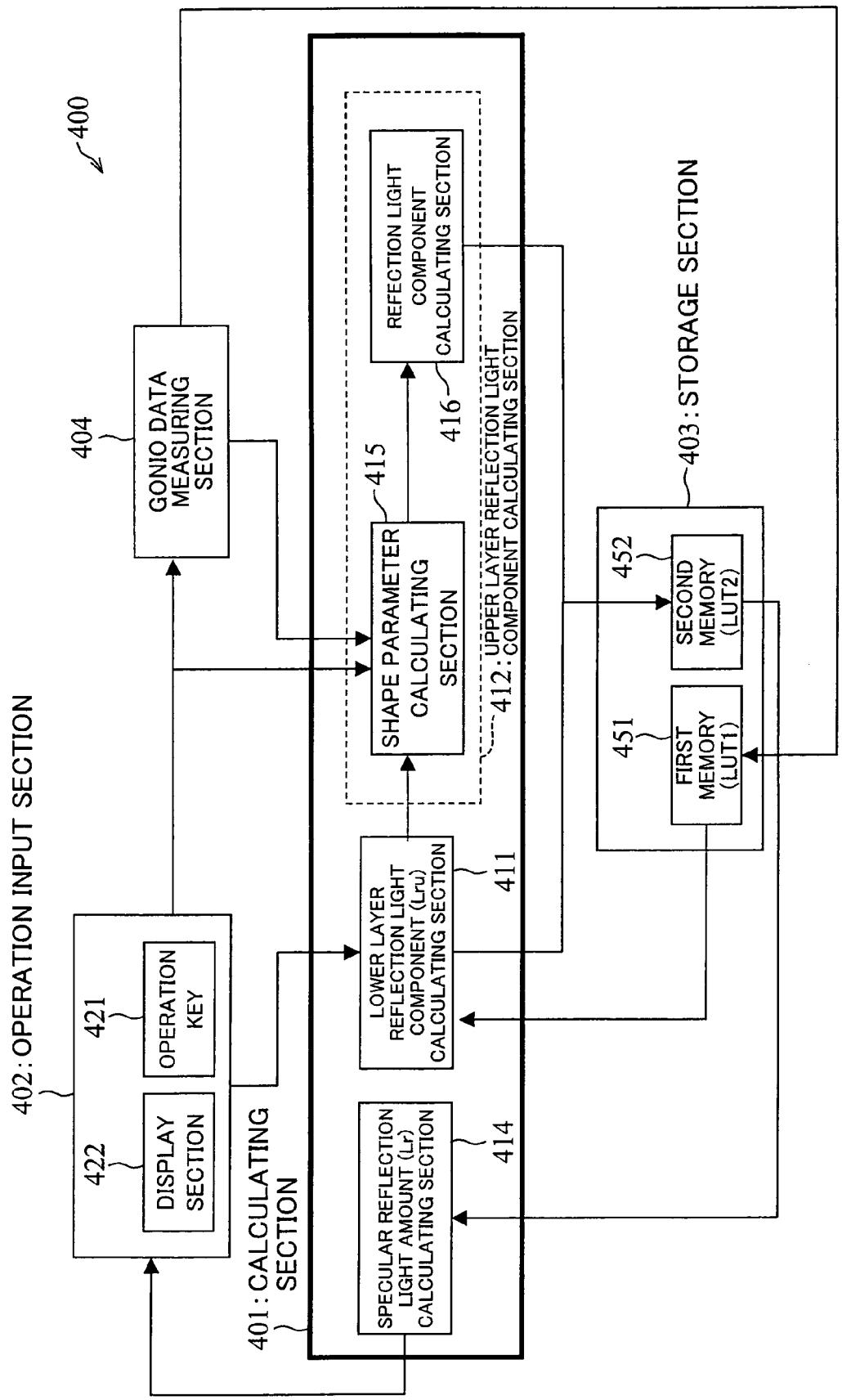
FIG. 25 is a block chart of an arrangement of a specular gloss simulation device, according to the embodiment 3 of the present invention.

Firstly, transmittance of an upper layer portion of a sample (toner image) is measured in advance by using a transmission density meter (at S1 in FIG. 24). The transmittance is to be inputted into the specular gloss simulation device 400 in order to measure the specular gloss component. Transmittance Tt is calculated out from Equation $Tt=10^{\wedge}(-Dt)$, where Dt is a transmission density of only the upper layer portion. The transmission density is worked out by obtaining a difference between transmission density of the sample on which the toner image is formed (i.e., the sample having the lower layer portion 33 and the upper layer portion 34) and that of the sample having the lower layer portion (paper) 33 only. A transmission density meter is used to measure the transmission density of the sample on which the toner image is formed (i.e., the sample having the lower layer portion 33 and the upper layer portion 34) and that of the sample having the lower layer portion (paper) 33 only. The measurement of the transmission density may be carried out with a X-rite model 820 transmission densitometer made by X-rite Inc.

The transmittance of the upper layer portion 34 is measured in S21 of the flowchart of FIG. 24. When using the specular gloss simulation device 400 of the present invention for evaluating the specular gloss, the transmittance is measured in advance by using a separate device, and the transmittance is inputted via the operation input section 402.

Next, a shape of the toner layer surface is measured, by using a shape-measuring microscope VK-9500(manufactured by KEYENCE corp.) and a variable of roughness of a surface of a toner layer is calculated based on height information (data regarding Z-axis direction, where a plane of the sample is an X,Y plane) obtained from the measurement. Slope of a microscopic surface of the toner layer surface is calculated based on the height information of an adjacent picture element. Then, after the slope of the microscopic surface is plotted in a histogram, a standard deviation of the slope of the microscopic surface is calculated within a range of $2\sigma$ (95.5% of the data) thereby to obtain the variable $\sigma s$ of roughness of the surface of the colorant material layer.

Meanwhile, a transmission image for the sample is obtained by using a CCD camera CS-3910 (manufactured by Tokyo Electronic Industry) and a transmission-use light source whose amount of light output is 200 W, and the variable of density distribution is calculated from the obtained transmission image data. The sample is placed between the CCD camera and the transmission-use light source. In other words, where the sample is X, Y plane, the CCD camera and the transmission-use light source are placed in the Z-direction. Then, the transmission image is obtained. Density of the picture elements of thus obtained transmission image is plotted in the histogram. Then, a standard deviation of transmission density is calculated within a range of 2σ (95.5% of the data thereby to obtain the variable σp of density distribution.

The variable σp of the density distribution and the variable σs of roughness of the surface shape of the sample are respectively measured in S27 and S28 of the flowchart of FIG. 24. When using the specular gloss simulation device 400 of the present invention for evaluating the specular gloss, the variables are measured in advance by using a separate device, and these variables are inputted at the same time the transmittance and the refractive index are inputted.

Next, the transmittance the variables σp and σs and the refractive index of the upper portion 34 of the sample thus measured by the above methods are inputted via the operation keys 421 of the operation input section 402. FIG. 26 illustrates an example of a data input screen displayed on the display section 422 of the specular gloss simulation device 400. On the data input screen illustrated in FIG. 27, an input item R20 for the refractive index of the upper portion of the sample to be measured and an input item R21 for transmittance (Tt) of the sample to be measured, an input item R22 for the variable of the roughness of the surface shape of the sample to be measured, and an input item R23 for the variable of density distribution of the sample to be measured are displayed. Further, an OK key R24, and a cancel key. R25 are displayed on the data input screen illustrated in FIG. 27, which are touch-panel keys. Via the operation keys 421, the transmittance, the refractive index, and the variables σp and σs thus obtained by the above methods are inputted respectively into the input items R21 to R23 on the display section 422. If the cancel key R25 is pressed on this data input screen, a measurement mode is terminated with the data input screen inactivated.

Then, a base material made of the same material as that of the base material of the sample to be measured (i.e., the sample having the lower layer portion) is put in the gonio data measuring section 404 of the specular gloss simulation device 400, then the OK key 24 is pressed. In this way, the gonio data measuring section 404 measures the gonio data (CIE 1976*a*b*L*) of the sample having only the lower portion (at S22 in FIG. 24). The gonio data thus measured is stored in the first memory 451 of the storage section 403.

As the gonio data measuring section 404, a gonio-photospectrometer GSP-2S (made by Murakami Color Research Laboratory) may be used, for example. Also, in the gonio data measurement in the case of a sample only having the lower layer portion, the angle resolution of the incident light angles and light reflection angles are 1°. For this reason, the first memory 451 stores the gonio data values which are measured in increments of 1° of the incident light angle and the light reflection angle. In the first memory 451, the gonio data values are associated with the corresponding incident light angles and light reflection angles.

Subsequently, based on the aforesaid refraction theory and attenuation theory, the lower layer reflection light component calculating section 411 calculates the lower layer reflection light components (Lru) of all geometries (the resolution is 1°, in the present example), in reference to (i) the refractive index and transmittance of the upper layer portion, which are supplied from the operation input section 402 and (ii) the gonio data values stored in the first memory 451 (S23 in FIG. 8). The lower layer reflection light components (Lru) thus calculated are stored in the second memory 452 in the storage section 403.

Then the first non-specular reflection geometry is selected, and the incident light angle and light reflection angle of the first non-specular reflection geometry are supplied from the operation input section 402. As a result, the gonio data measuring section 404 measures the gonio data Lra of the first non-specular reflection geometry (S24 in FIG. 8). Subsequently, the second non-specular reflection geometry is selected, the incident light angle and light reflection angle of the second non-specular reflection geometry are supplied from the operation input section 402, and the gonio data Lru of the second non-specular reflection geometry is measured (S25 in FIG. 24). Then the specular reflection geometry is further selected, the incident light angle and the light reflection angle of this specular reflection geometry are supplied from the operation input section 402, and the gonio data Lrb of the specular reflection geometry is measured (S26 in FIG. 24).

FIG. 27 shows an example of a data input screen displayed on the display section 422 in order to input the selected first non-specular reflection geometry, second non-specular reflection geometry, and specular reflection geometry. It is noted that although the first non-specular reflection geometry, second non-specular geometry, and specular reflection geometry are simultaneously input in the case above, the present invention is not necessarily limited to this arrangement. The data input screen shown in FIG. 27 displays: an input item R30 and an input item R31 for the incident light angle and the light reflection angle of the second non-specular reflection geometry. respectively; an input item R37 and an input item R38 for the incident light angle and the light reflection angle of the first non-specular reflection geometry, respectively; an input item R32 and an input item R33 for the incident light angle and the light reflection angle of the specular reflection geometry, respectively; an OK button R34; a cancel button R35; and a back button R36. In the present case, the OK button R34, cancel button R35, and back button R36 are touch-panel type. If the cancel button R35 is pushed, the data input screen finishes and the measurement mode is compulsorily terminated. If the back button R36 is pushed, the data input screen shown in FIG. 27 is shown again.

The incident light angles and the light reflection angles of the first and second non-specular reflection geometries must be individually specified. However, since the incident light angle is equal to the light reflection angle in the specular reflection geometry, the value of the incident light angle input in the input item R32 for the incident light angle is automatically displayed and set in the item R33 for the light reflection angle.

After the first non-specular reflection geometry, second non-specular reflection geometry, and specular reflection geometry are input as above and the sample in which a toner image is formed is set in the gonio data measuring section 404, the OK button R34 is pushed. In response to this, the gonio data values Lra, Lrb, and Lrc of each of the aforesaid geometries are measured.

The gonio data values Lra, Lrb, and Lrc of each geometry, which have been measured, are supplied to the upper layer reflection light component calculating section 412. In accordance with the gonio data values Lra, Lrb, and Lrc thus supplied, the upper layer reflection light component calculating section 412 performs the fitting with the Oren-Nayar model and the Torrance-Sparrow model, and calculates the diffuse reflection light components (Lrd), the surface reflection light components (Lrs), and the reflection light components (Lrsp) of the colorant material particles, of all geometries (Steps S29 and S30).

The following more specifically describes the process above. First, the gonio data value measured by the gonio data measuring section 404 is supplied to the configuration parameter calculating section 415 of the upper layer reflection light component calculating section 412. Also, the configuration parameter calculating section 415 obtains, from the second memory 452, the lower layer reflection light components Lru of the first non-specular reflection geometry, the second non-specular reflection geometry, and the specular reflection geometry. From the operation input section 402, roughness parameters σp and σs are supplied to the configuration parameter calculating section 415. The configuration parameter calculating section 415 then performs the fitting in accordance with the aforesaid method, so as to calculate (i) a parameter ρ indicating the reflectance on a microscopic surface in the case of the Oren-Nayar model, and (ii) parameters kss, ksp, and kd indicating the distribution ratio among the diffuse reflection light component, the surface reflection light component, and the reflection light component of the colorant material particles (Step S29).

The calculated values ρ, kss, ksp, and kd are supplied from the configuration parameter calculating section 415 to the reflection light component calculating section 416. By the aforesaid method, the reflection light component calculating section 416 calculates, for all geometries, the diffuse reflection light components (Lrd), the surface reflection light components (Lrs), and the reflection light components (Lrsp) of the colorant material particles (Step S30). Then the reflection light component calculating section 416 stores these reflection light components in the second memory 452. The reflection light components stored in the second memory 452 are associated with the corresponding geometries.

Figure 28:
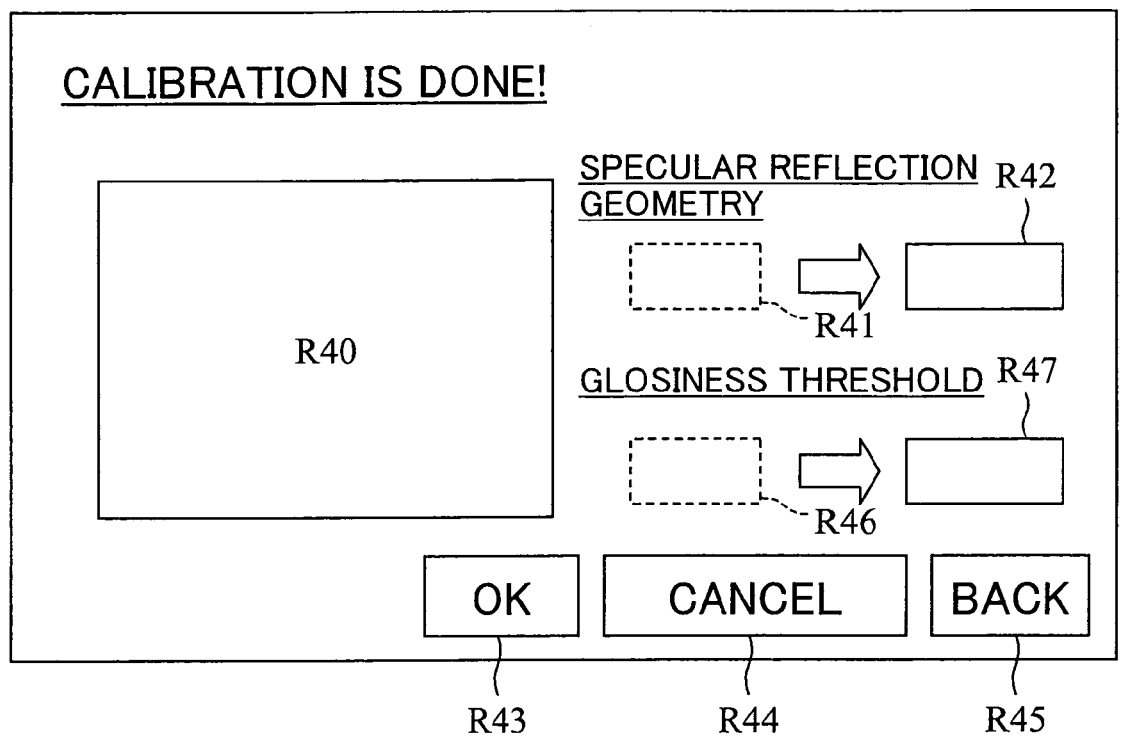
FIG. 28 is a diagram schematically illustrating an example of a screen displaying a result of a measurement, the result being displayed on a display section of the specular glossiness simulation device as illustrated in FIG. 25.

Subsequently, the specular reflection light component calculating section 414 obtains, for each geometry, the lower layer reflection light component (Lru), the diffuse reflection light component (Lrd), the surface reflection light component (Lrs) and the reflection light component (Lrsp) of the colorant material particles, from the second memory 452. The specular reflection light component calculating section 414 then adds up these components so as to calculate the specular reflection light component (Lr) (Step S31). In the present embodiment, the specular reflection light component (Lr) is calculated for each geometry. The calculated specular reflection light components (Lr) of all geometries are supplied to the display section 422 of the operation input section 402, letting the user see the result on the display section 422. FIG. 28 shows an example of the measurement result displayed on the display section 422.

As shown in FIG. 28, after the calculation of the specular reflection light components Lr, the display section 422 displays: a graph R40 of the specular reflection light components Lr; an input item R41 for the specular reflection geometry; a calculation result R42 of the specular reflection light component Lr of the geometry input in the input item R41; an input item R46 for a gloss threshold; a calculation result R47 of the specular reflection geometry indicating the threshold input in the input item R46; an OK button R43; a cancel button R44; and a back button R45. The graph R40 of the specular reflection light components Lr shows the list of all specular reflection light components Lr, in a case where the incident light angles are in the range of 10° and 80°. It is therefore possible to see what extent a sample specular reflection light component is dependent on the angle. The results shown in the graph R40 are calculated in the specular reflection light component calculating section 414 by adding up the lower layer reflection light components Lru, diffuse reflection light components Lrd, surface reflection light components Lrss, and reflection light components Lrsp of the colorant material particle, of all specular reflection geometries stored in the second memory 452.

In the specular gloss simulation device 400, an arbitrary angle is input in the input item R41 of the specular reflection geometry shown in FIG. 28, and the OK button R43 is pushed. With this, the value of the specular reflection light component of the angle thus input is obtained. The calculated value of this case is equal to a point on the graph R40 of the specular reflection light components Lr.

In the meanwhile, a desired specular reflection light component (corresponding to the gloss) is inputted in the input item R46 for the gloss threshold and the OK button R43 is pushed. With this, an angle corresponding to the specular reflection light component thus input is displayed as the calculation result R47. The calculation result proves that angles corresponding to the specular reflection light components higher than the component thus inputted are greater than the displayed angle. In other words, the specular gloss simulation device 400 of the present embodiment makes it possible to calculate the specular reflection light components of all specular reflection geometries. Therefore, by varying the specular reflection geometry (incident and light reflection angles), it is possible to confirm in which case the specular reflection light component exceeds a predetermined value. This can be effectively used as a novel valuation standard for the gloss.

If the cancel button R44 in the result screen shown in FIG. 28 is pushed, the result screen finishes and the measurement mode is compulsorily terminated. If the back button R45 is pushed, the data input screen shown in FIG. 27 is shown again.

In a case where the specular reflection light component simulated as above is converted to the gloss in conformity to Japanese Industrial Standards, the gloss is figured out in such a manner that a relative value is calculated based on a value in the case of a standard plate (glass plate with a refractive index of 1.567) specified as a standard sample.

The specular gloss simulation device 400 may be realized using a computer system. The computer system may be similar to the computer system 300 (see FIG. 12) of Embodiment 1.

As in the case of Embodiment 1, the processing steps performed by the calculating section 401 of the specular gloss simulation device 400 of the present embodiment and the processing steps performed by the lower layer reflection light component calculating section 411, the upper layer reflection light component calculating section 412, the specular reflection light component calculating section 414 in the calculating section 401 are realized by causing computing means such as a CPU to execute a program stored in storage means such as ROM (Read Only Memory) or RAM, so as to control the input means such as a keyboard, output means such as a display, or a communication means such as an interface circuit. On this account, the functions and processes of the specular gloss simulation device 400 can be realized only by causing the computer having the aforesaid means to read a storage medium storing the program and execute the program. If the program is stored in a removable storage medium, the aforesaid functions and processes can be realized on any computer.

The invention being thus described, it will be obvious that the same may be varied in many ways. Such variations are not to be regarded as a departure from the spirit and scope of the invention, and all such modifications as would be obvious to one skilled in the art intended to be included within the scope of the following claims.

EXAMPLE 1

In the present example, a sample was prepared by using a high concentration toner for forming a colorant material layer on a base material which was paper, and specular glossiness of the sample was evaluated by using the specular gloss simulation device 100 of Embodiment 1.

First, values were entered as follows in respective input items on a data input screen illustrated in FIG. 9. Namely, "1.55" was entered in a refractive index input item 20, and "6.4%" was entered in a transmission-factor input item 21. Meanwhile, a sample which was paper having no colorant material layer was set at a gonio data measuring section 104, and then gonio data was measured. Then, values were entered as follows in respective input items on a data input screen illustrated in FIG. 10. Namely, for a non-specular reflection geometry, "45°" was entered in an incident light angle input item 30, and "−60°" was entered in a reflection light angle input item 31. For a specular reflection geometry, "45°" was entered in an incident light angle input item 32. Meanwhile, the sample having the toner image was set at a gonio data measuring section 104, and then gonio data was measured.

FIG. 20(a) shows a graph 40 of FIG. 11 which was displayed as a result of the measurement. In the graph illustrated in FIG. 20(a), the horizontal axis indicates the incident light angle and the reflection light angle in the specular reflection geometry, and a vertical axis indicates a luminance value (L* of CIE1976L*a*b*) of a specular reflection light component. In the present example, a gonio-photo spectrometer was used so as to carry out, with respect to the same sample, an actual measurement of the geometric specular reflection light component in each specular reflection geometry. Then, the result of the actual measurement and the result of the foregoing measurement were compared with each other. In the graph of FIG. 20(a), the solid line indicates the result obtained from the calculation using the technique of the present invention, and the dotted line indicates the result obtained from the actual measurement. As indicated in the figure, the two results exhibited substantially identical behaviors. This proves that the technique of the present invention is highly accurate.

EXAMPLE 2

In the present example, a sample was prepared by using a low concentration toner for forming a colorant material layer on a base material which was paper, and specular glossiness of the sample was evaluated by using the specular gloss simulation device 100 of Embodiment 1.

First, values were entered as follows in respective input items on a data input screen illustrated in FIG. 9. Namely, "1.55" was entered in a refractive index input item 20, and "15%" was entered in a transmission-factor input item 21. Meanwhile, a sample which was paper having no colorant material layer was set at a gonio data measuring section 104, and then gonio data was measured. Then, values were entered as follows in respective input items on a data input screen illustrated in FIG. 10. Namely, for a non-specular reflection geometry, "45°" was entered in an incident light angle input item 30, and "−60°" was entered in a reflection light angle input item 31. For a specular reflection geometry, "45°" was entered in an incident light angle input item 32. Meanwhile, the sample having the toner image was set at a gonio data measuring section 104, and then gonio data was measured.

FIG. 20(b) shows a graph 40 of FIG. 11 which was displayed as a result of the measurement. In the graph illustrated in FIG. 20(b), the horizontal axis indicates the incident light angle and the reflection light angle in the specular reflection geometry, and a vertical axis indicates a luminance value (L* of CIE1976L*a*b*) of a specular reflection light component. In the present example, a gonio-photo spectrometer was used so as to carry out, with respect to the same sample, an actual measurement of the geometric specular reflection light component in each specular reflection geometry. Then, the result of the actual measurement and the result of the foregoing measurement were compared with each other. In the graph of FIG. 20(b), the solid line indicates the result obtained from the calculation using the technique of the present invention, and the dotted line indicates the result obtained from the actual measurement. As indicated in the figure, the two results exhibited substantially identical behaviors. This proves that the technique of the present invention is highly accurate, even if an influence from a luminance component of reflection from paper increases due to decrease in a toner concentration.

EXAMPLE 3

In the present example, paper of 67 g/m$^2$ or 128 g/m$^2$ is used as a base material. On this base material, a colorant material layer was formed by using a high concentration toner, thereby preparing a sample. Then, specular glossiness of the sample was evaluated by using the specular gloss simulation device 100 of Embodiment 1.

The evaluation of the specular glossiness was carried out as in Examples 1 and 2, except in that, in the transmission-factor input item 21 illustrated in FIG. 9, "7.5%" was entered when using the paper of 67 g/m$^2$, and "7.2%" was entered when using the paper of 128 g/m$^2$. FIG. 21(a) shows a result obtained in the case of using the paper of 67 g/m$^2$, and FIG. 21(b) shows a result obtained in the case of using the paper of 128 g/m$^2$. Note that, as in the foregoing examples, a gonio-photo spectrometer was also used in the present example, so as to carry out, with respect to the same sample, an actual measurement of the geometric specular reflection light component in each specular reflection geometry. Then, the result of the actual measurement and the result of the foregoing measurement were compared with each other.

As indicated in the figure, the calculation result and the actually-measured value were substantially identical to each other at all of the angles in the present example too. Further, it is found that an angle change causes a less amount of change in the luminance value, than a case of using paper. This is because a greater roughness of a toner layer surface causes wider scattering of a surface reflection light component Lrs, which consequently increases influence from an internal reflection light component Lri. As described, it is found that the technique of the present invention is highly accurate, even if the influence from the internal reflection light component Lri increases.

EXAMPLE 4

In the present example, a sample was prepared by using a high concentration toner for forming a colorant material layer on a base material which was paper, and specular glossiness of the sample was evaluated by using the specular gloss simulation device 200 of Embodiment 2.

First, values were entered as follows in respective input items on a data input screen illustrated in FIG. 17. Namely, "1.55" was entered in a refractive index input item 50, "6.4%" was entered in a transmission-factor input item 51, "0.205"

was entered in a surface coarseness input item 52, and "0.037" was entered in a density distribution input item 53. Meanwhile, a sample which was paper having no colorant material layer was set at a gonio data measuring section 204, and then gonio data was measured.

Then, values were entered as follows in respective input items on a data input screen illustrated in FIG. 18. Namely, for a non-specular reflection geometry, "45°" was entered in an incident light angle input item 60, and "−60°" was entered in a reflection light angle input item 61. For a specular reflection geometry, "45°" was entered in an incident light angle input item 62. Meanwhile, the sample having the toner image was set at a gonio data measuring section 204, and then gonio data was measured.

Figure 22:
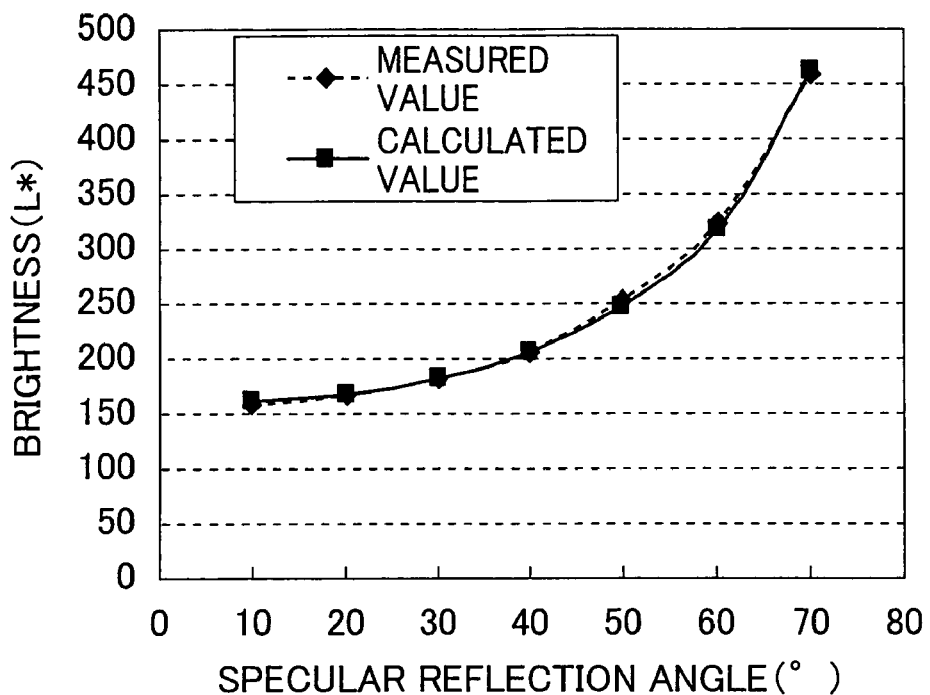
FIG. 22(a) is a graph illustrating a result of an example 4 (specular glossiness simulation by using a high-concentration toner sample)
FIG. 22(b) is a graph illustrating a result of an example 5 (specular glossiness simulation by using a toner sample having low concentration).
Figure 22:
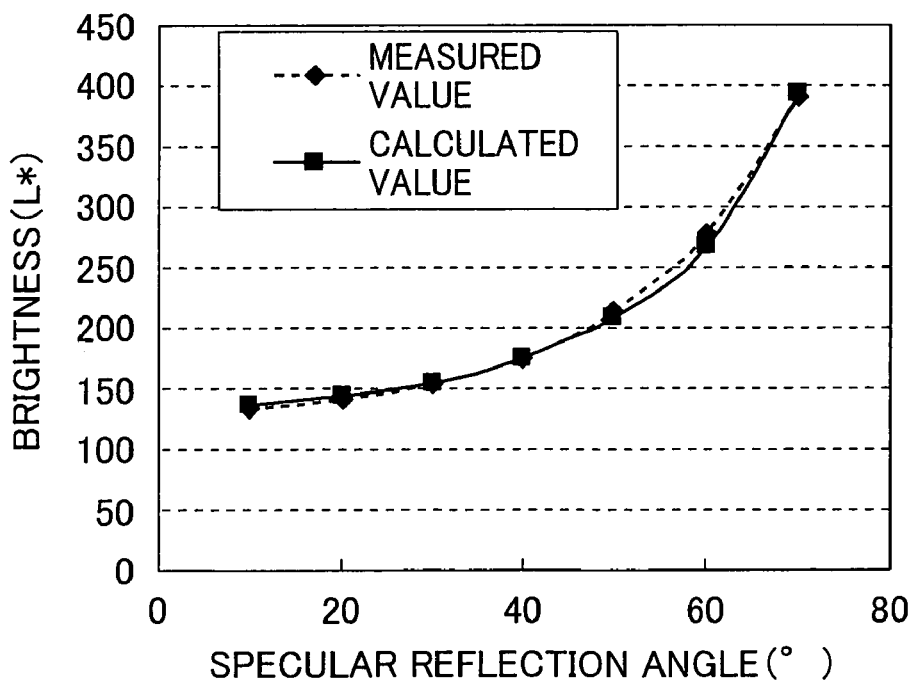

FIG. 22(*a*) shows a graph 70 of FIG. 19 which was displayed as a result of the measurement. In the graph illustrated in FIG. 22(*a*), the horizontal axis indicates the incident light angle and the reflection light angle in the specular reflection geometry, and a vertical axis indicates a luminance value (L* of CIE1976L*a*b*) of a specular reflection light component. In the present example, a gonio-photo spectrometer was used so as to carry out, with respect to the same sample, an actual measurement of the geometric specular reflection light component in each specular reflection geometry. Then, the result of the actual measurement and the result of the foregoing measurement were compared with each other. In the graph of FIG. 22(*a*), the solid line indicates the result obtained from the calculation using the technique of the present invention, and the dotted line indicates the result obtained from the actual measurement. As indicated in the figure, the two results exhibited substantially identical behaviors. This proves that the technique of the present invention is highly accurate.

Figure 20:
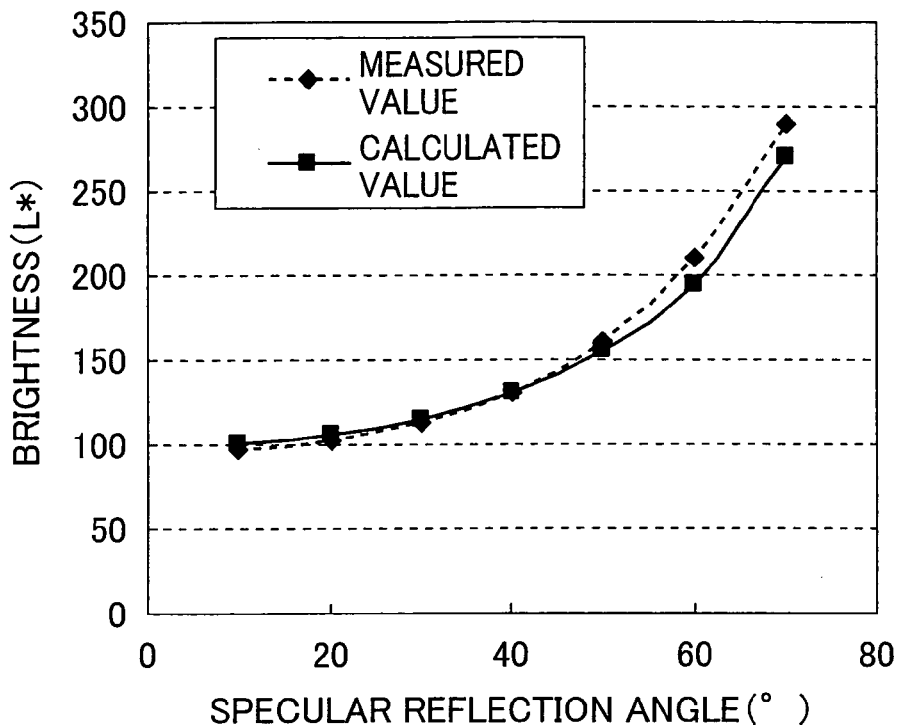
FIG. 20 (a) is a graph illustrating a result of an example 1 (specular glossiness simulation by using a high-concentration toner sample)
Figure 20:
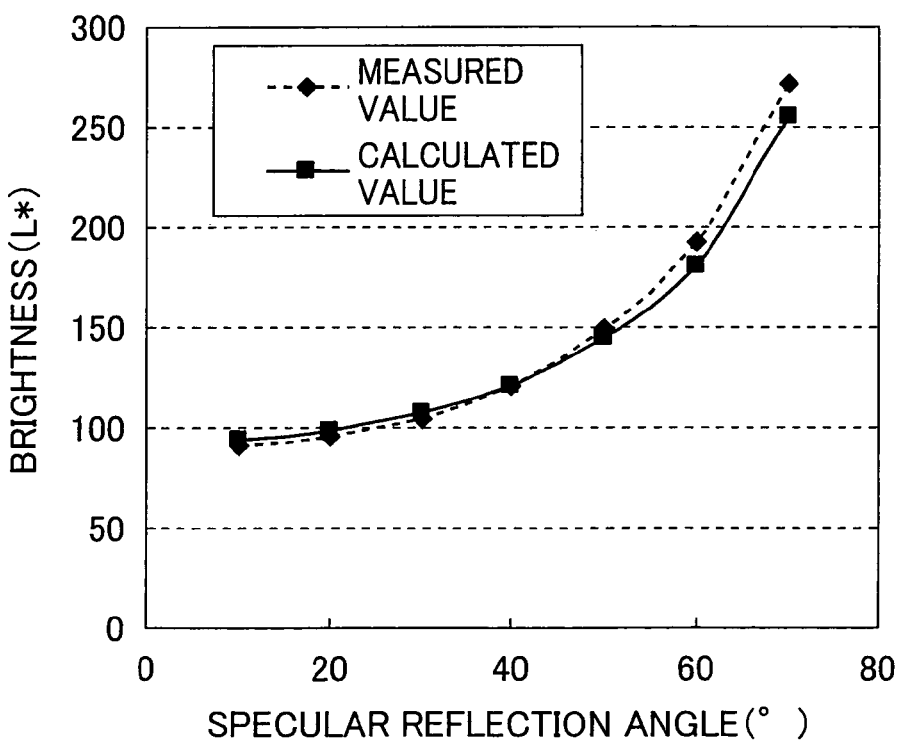

By comparing FIG. 20(*a*) and FIG. 22(*a*), it becomes apparent that the values calculated out in the present example are closer to the actually measured values than those calculated in Example 1 in which the specular gloss simulation device 100 of Embodiment 1 was used for evaluating the specular glossiness under the same conditions. In short, it is confirmed that the technique of the present example is more accurate than the technique of Example 1.

EXAMPLE 5

In the present example, a sample was prepared by using a low concentration toner for forming a colorant material layer on a base material which was paper, and specular glossiness of the sample was evaluated by using the specular gloss simulation device 200 of Embodiment 2.

First, values were entered as follows in respective input items on a data input screen illustrated in FIG. 17. Namely, "1.55" was entered in a refractive index input item 50, "15%" was entered in a transmission-factor input item 51, "0.222" was entered in a surface coarseness input item 52, and "0.047" was entered in a density distribution input item 53. Meanwhile, a sample which was paper having no colorant material layer was set at a gonio data measuring section 204, and then gonio data was measured.

Then, values were entered as follows in respective input items on a data input screen illustrated in FIG. 18. Namely, for a non-specular reflection geometry, "45°" was entered in an incident light angle input item 60, and "−60°" was entered in a reflection light angle input item 61. For a specular reflection geometry, "45°" was entered in an incident light angle input item 62. Meanwhile, the sample having the toner image was set at a gonio data measuring section 204, and then gonio data was measured.

FIG. 22(*b*) shows a graph 70 of FIG. 19 which was displayed as a result of the measurement. In the graph illustrated in FIG. 22(*b*), the horizontal axis indicates the incident light angle and the reflection light angle in the specular reflection geometry, and a vertical axis indicates a luminance value (L* of CIE1976L*a*b*) of a specular reflection light component. In the present example, a gonio-photo spectrometer was used so as to carry out, with respect to the same sample, an actual measurement of the geometric specular reflection light component in each specular reflection geometry. Then, the result of the actual measurement and the result of the foregoing measurement were compared with each other. In the graph of FIG. 22(*b*), the solid line indicates the result obtained from the calculation using the technique of the present invention, and the dotted line indicates the result obtained from the actual measurement. As indicated in the figure, the two results exhibited substantially identical behaviors. This proves that the technique of the present invention is highly accurate, even if an influence from a luminance component of reflection from paper increases due to decrease in a toner concentration.

By comparing FIG. 20(*b*) and FIG. 22(*b*), it becomes apparent that the values calculated out in the present example are closer to the actually measured values than those calculated in Example 2 in which the specular gloss simulation device 100 of Embodiment 1 was used for evaluating the specular glossiness under the same conditions. In short, it is confirmed that the technique of the present example is more accurate than the technique of Example 2.

EXAMPLE 6

In the present example, paper of 67 g/m$^2$ or 128 g/m$^2$ is used as a base material. On this base material, a colorant material layer was formed by using a high concentration toner, thereby preparing a sample. Then, specular glossiness of the sample was evaluated by using the specular gloss simulation device 200 of Embodiment 2.

Figure 23:
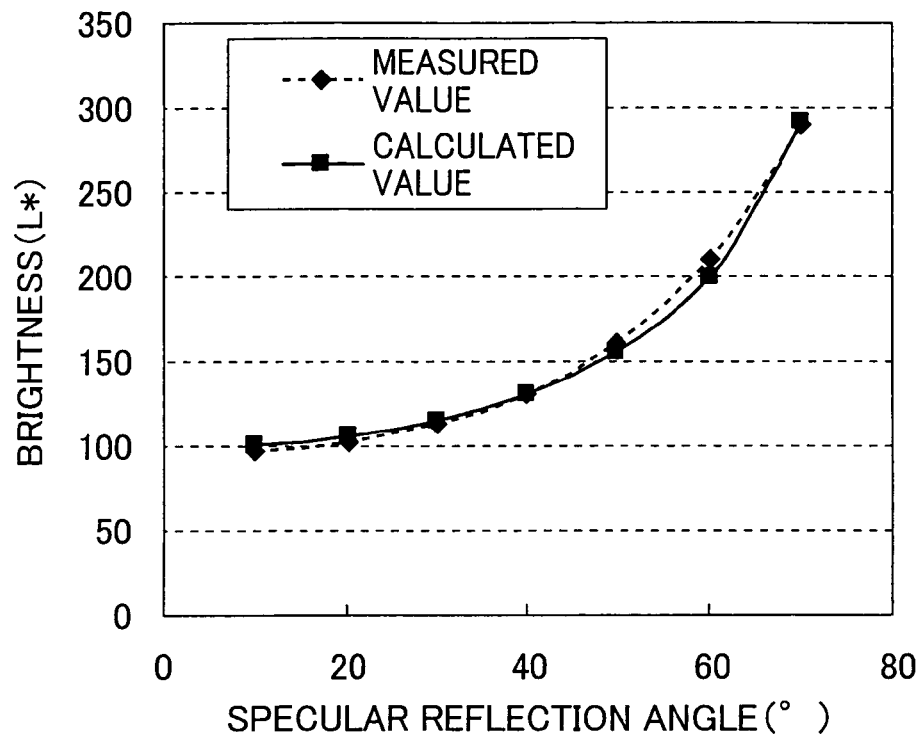
FIG. 23(a) and FIG. 23(b) are graphs illustrating results of an example 6.
Figure 23:
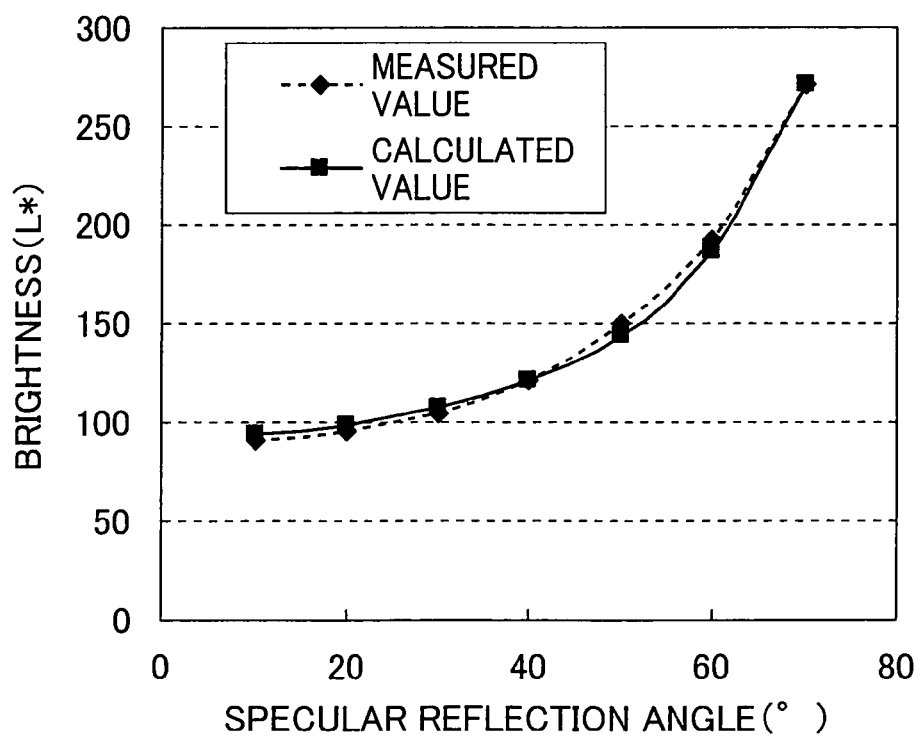

The evaluation of the specular glossiness was carried out as in Examples 4 and 5, except in that, in the transmission-factor input item 51 illustrated in FIG. 17, "7.5%" was entered when using the paper of 67 g/m$^2$, and "7.2%" was entered when using the paper of 128 g/m$^2$. FIG. 23(*a*) shows a result obtained in the case of using the paper of 67 g/m$^2$, and FIG. 23(*b*) shows a result obtained in the case of using the paper of 128 g/m$^2$. Note that, as in the foregoing examples, a gonio-photo spectrometer was also used in the present example, so as to carry out, with respect to the same sample, an actual measurement of the geometric specular reflection light component in each specular reflection geometry. Then, the result of the actual measurement and the result of the foregoing measurement were compared with each other.

As indicated in the figure, the calculation result and the actually-measured value were substantially identical to each other at all of the angles in the present example too. Further, it is found that an angle change causes a less amount of change in the luminance value, than a case of using paper. This is because a greater roughness of a toner layer surface causes wider scattering of a surface reflection light component Lrss and wider scattering of a reflection light component Lrsp from colorant material particle, which consequently increases an influence from a diffuse reflection light component Lrd. As described, it is found that the technique of the present invention is highly accurate, even if the influence from the diffuse reflection light component Lrd increases.

Figure 21:
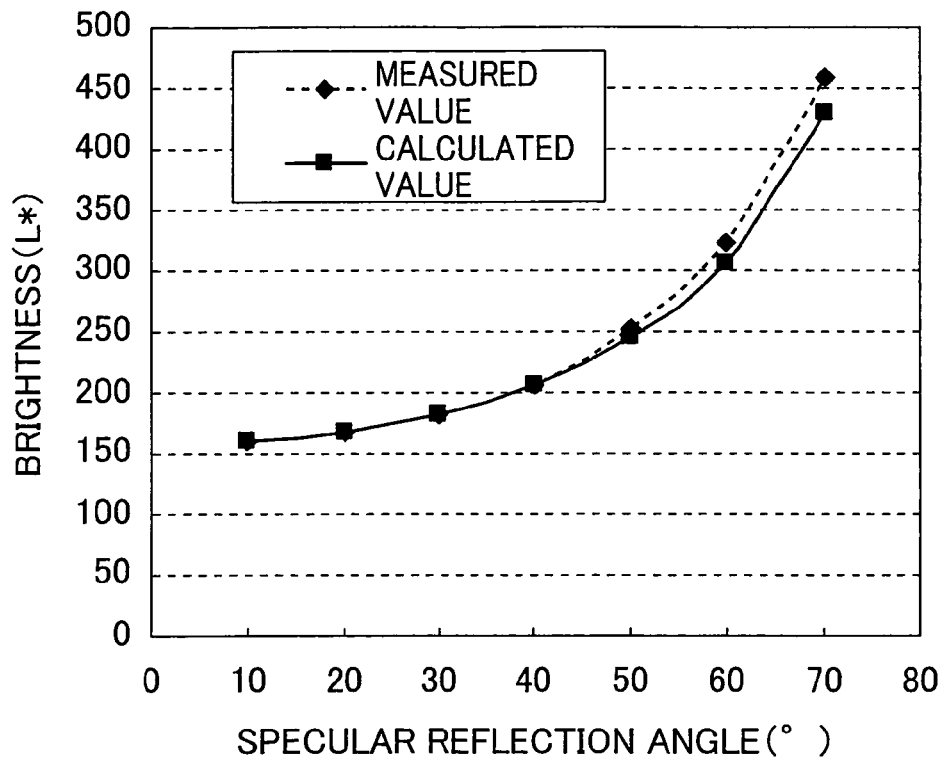
FIGS. 21(a) and 21(b) are graphs illustrating results of an example 3.
Figure 21:
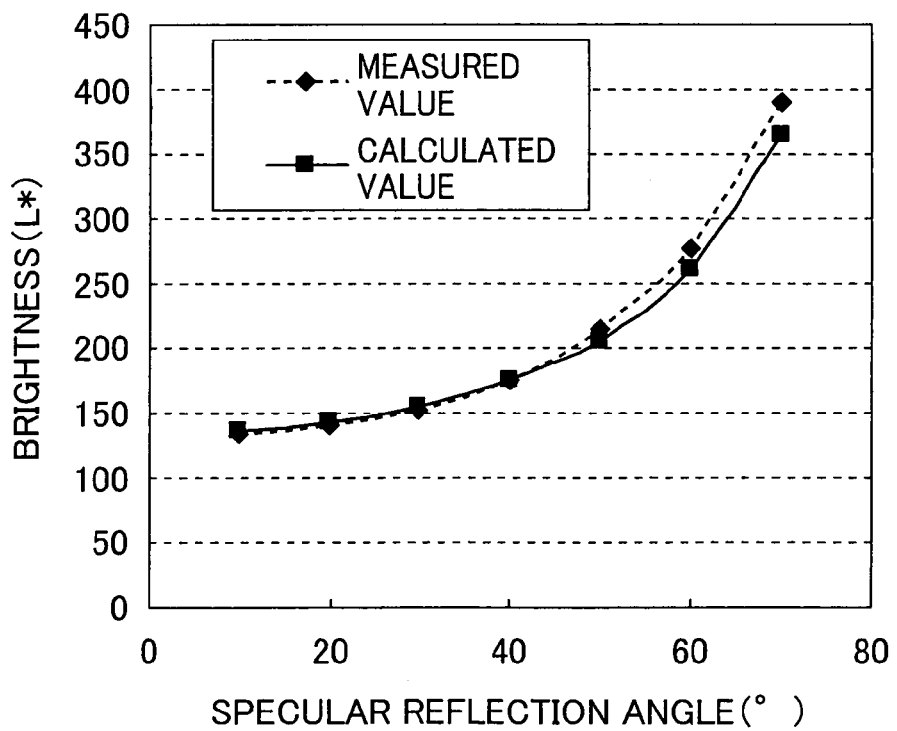

By comparing FIG. 21 and FIG. 23, it becomes apparent that the values calculated out in the present example are closer to the actually measured values than those calculated in Example 3 in which the specular gloss simulation device 100 of Embodiment 1 was used for evaluating the specular glossiness under the same conditions. In short, it is confirmed that the technique of the present example is more accurate than the technique of Example 3.

EXAMPLE 7

In the present example, a sample was prepared by using a high concentration toner for forming a colorant material layer on a base material which was paper, and specular glossiness of the sample was evaluated by using the specular gloss simulation device 400 of Embodiment 3.

First, values were entered as follows in respective input items on a data input screen illustrated in FIG. 17. Namely, "1.55" was entered in a refractive index input item R20, "6.4%" was entered in a transmission-factor input item R21, "0.205" was entered in a surface coarseness input item R22, and "0.037" was entered in a density distribution input item R23. Meanwhile, a sample which was paper having no colorant material layer was set at a gonio data measuring section 404, and then gonio data was measured.

Then, values were entered as follows in respective input items on a data input screen illustrated in FIG. 27. Namely, for a first non-specular reflection geometry, "45°" was entered in an incident light angle input item R30, and "−60°" was entered in a reflection light angle input item R31. For a second non-specular reflection geometry, "45°" was entered in an incident light angle input item R37, and "0°" was entered in a reflection light angle input item R38. For a specular reflection geometry, "45°" was entered in an incident light angle input item R32. Meanwhile, the sample having the toner image was set at a gonio data measuring section 404, and then gonio data was measured.

Figure 29:
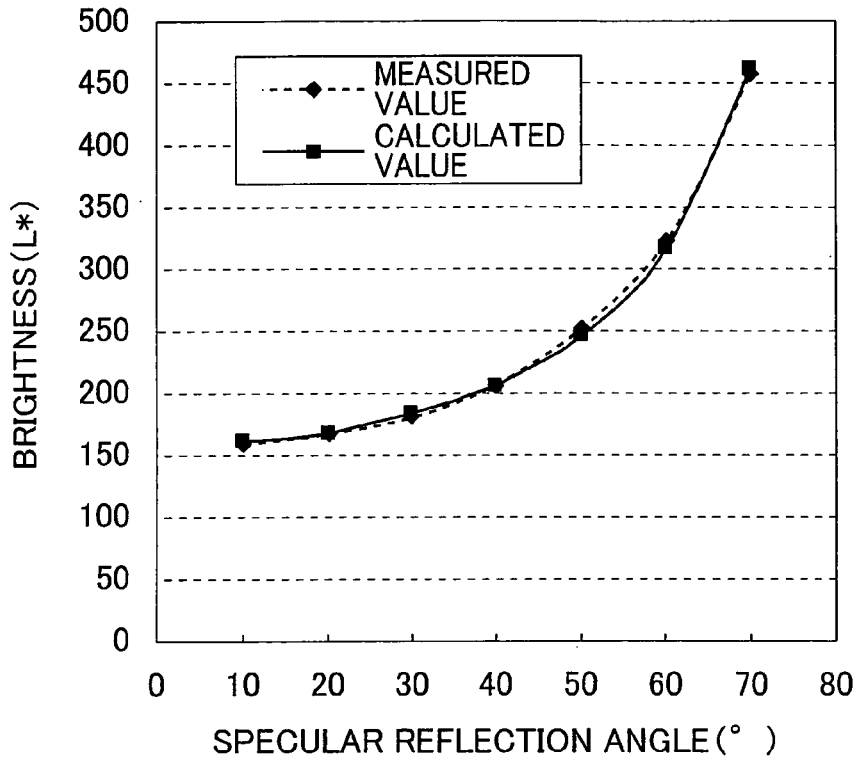
FIG. 29(a) is a graph illustrating a result of an example 7 (specular glossiness simulation by using a highly concentrated toner sample)
FIG. 29(b) is a graph illustrating a result of an example 8 (specular glossiness simulation by using a toner sample having low concentration).
Figure 29:
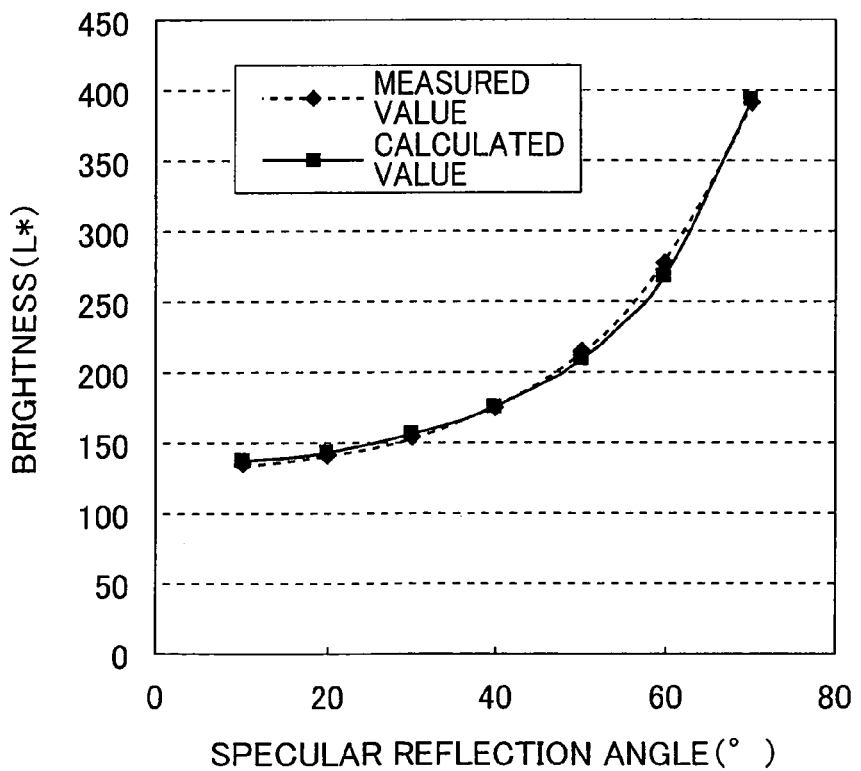

FIG. 29(*a*) shows a graph R40 of FIG. 28 which was displayed as a result of the measurement. FIG. 29(*a*) shows a result obtained in a case of using a high concentration toner sample. In the graph illustrated in FIG. 29(*a*), the horizontal axis indicates the incident light angle and the reflection light angle in the specular reflection geometry, and a vertical axis indicates a luminance value (L* of CIE1976L*a*b*) of a specular reflection light component. In the present example, a gonio-photo spectrometer was used so as to carry out, with respect to the same sample, an actual measurement of the geometric specular reflection light component in each specular reflection geometry. Then, the result of the actual measurement and the result of the foregoing measurement were compared with each other. In the graph of FIG. 29(*a*), the solid line indicates the result obtained from the calculation using the technique of the present invention, and the dotted line indicates the result obtained from the actual measurement. As indicated in the figure, the two results exhibited substantially identical behaviors. This proves that the technique of the present invention is highly accurate.

EXAMPLE 8

In the present example, a sample was prepared by using a low concentration toner for forming a colorant material layer on a base material which was paper, and specular glossiness of the sample was evaluated by using the specular gloss simulation device 400 of Embodiment 3.

First, values were entered as follows in respective input items on a data input screen illustrated in FIG. 26. Namely, "1.55" was entered in a refractive index input item R20, "15%" was entered in a transmission-factor input item R21, "0.222" was entered in a surface coarseness input item R22, and "0.047" was entered in a density distribution input item R23. Meanwhile, a sample which was paper having no colorant material layer was set at a gonio data measuring section 404, and then gonio data was measured.

Then, values were entered as follows in respective input items on a data input screen illustrated in FIG. 27. Namely, for a first non-specular reflection geometry, "45°" was entered in an incident light angle input item R30, and "−60°" was entered in a reflection light angle input item R31. For a second non-specular reflection geometry, "45°" was entered in an incident light angle input item R37, and "0°" was entered in a reflection light angle input item R38. For a specular reflection geometry, "45°" was entered in an incident light angle input item R32. Meanwhile, the sample having the toner image was set at a gonio data measuring section 404, and then gonio data was measured.

FIG. 29(*b*) shows a graph R40 of FIG. 28 which was displayed as a result of the measurement. FIG. 29(*b*) shows a result obtained in a case of using a toner sample whose concentration is lower than that used in Example 7. In the graph illustrated in FIG. 29(*b*), the horizontal axis indicates the incident light angle and the reflection light angle in the specular reflection geometry, and a vertical axis indicates a luminance value (L* of CIE1976L*a*b*) of a specular reflection light component. In the present example, a gonio-photo spectrometer was used so as to carry out, with respect to the same sample, an actual measurement of the geometric specular reflection light component in each specular reflection geometry. Then, the result of the actual measurement and the result of the foregoing measurement were compared with each other. In the graph of FIG. 29(*b*), the solid line indicates the result obtained from the calculation using the technique of the present invention, and the dotted line indicates the result obtained from the actual measurement. As indicated in the figure, the two results exhibited substantially identical behaviors. This proves that the technique of the present invention is highly accurate, even if an influence from a luminance component of reflection from paper increases due to decrease in a toner concentration.

EXAMPLE 9

In the present example, paper of 67 g/m² or 128 g/m² is used as a base material. On this base material, a colorant material layer was formed by using a high concentration toner, thereby preparing a sample. Then, specular glossiness of the sample was evaluated by using the specular gloss simulation device 400 of Embodiment 3.

Figure 30:
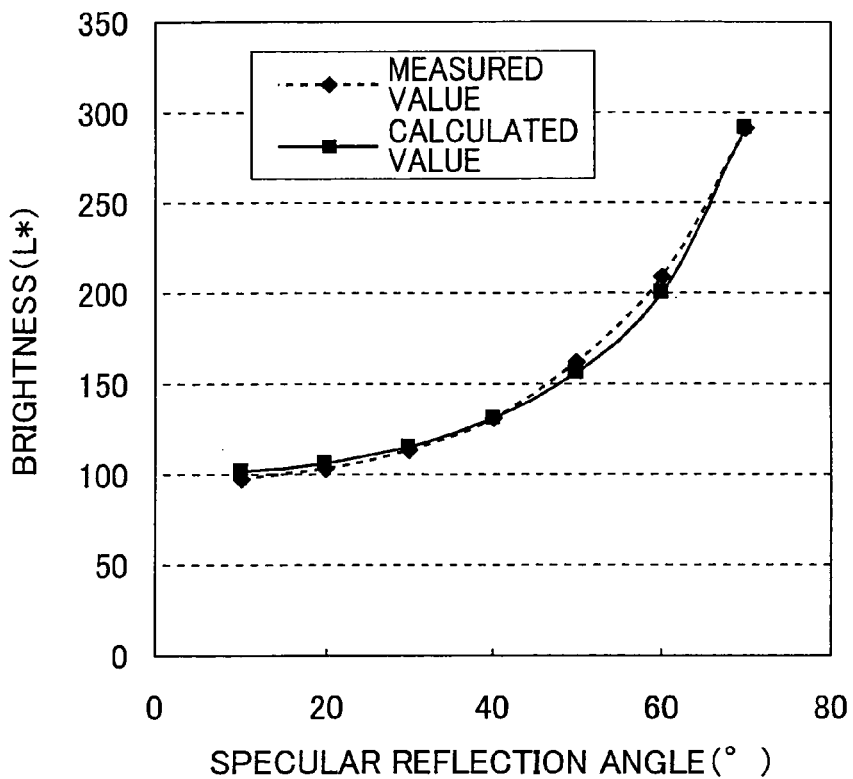
FIG. 30(a) and FIG. 30(b) are graphs illustrating results of an example 9.
Figure 30:
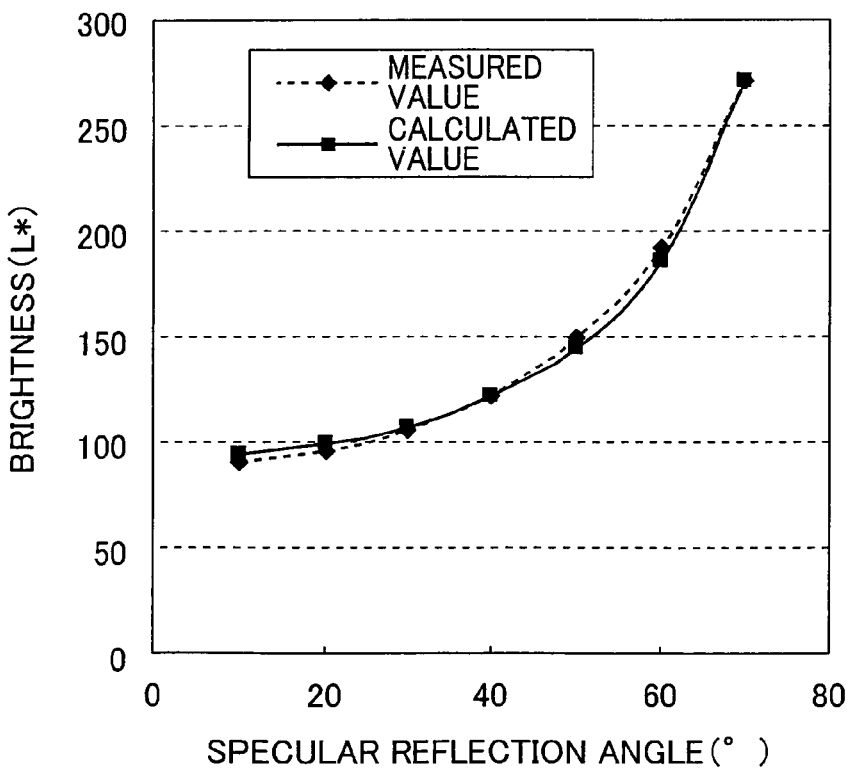

The evaluation of the specular glossiness was carried out as in Examples 7 and 8, except in that, in the transmission-factor input item R21 illustrated in FIG. 26, "7.5%" was entered when using the paper of 67 g/m², and "7.2%" was entered when using the paper of 128 g/m². FIG. 30(*a*) shows a result obtained in the case of using the paper of 67 g/m², and FIG. 30(*b*) shows a result obtained in the case of using the paper of 128 g/m². Note that, as in the foregoing examples, a gonio-photo spectrometer was also used in the present example, so as to carry out, with respect to the same sample, an actual measurement of the geometric specular reflection light component in each specular reflection geometry. Then, the result of the actual measurement and the result of the foregoing measurement were compared with each other.

As indicated in the figure, the calculation result and the actually-measured value were substantially identical to each other at all of the angles in the present example too. Further, it is found that an angle change causes a less amount of change in the luminance value, than a case of using paper.

This is because a greater roughness of a toner layer surface causes wider scattering of a surface reflection light component Lrss and wider scattering of a reflection light component Lrsp from colorant material particle, which consequently increases an influence from a diffuse reflection light component Lrd. As described, it is found that the technique of the present invention is highly accurate, even if the influence from the diffuse reflection light component Lrd increases.

OTHER

According to the present invention, it is possible to accurately evaluate specular gloss of an image formed in various ways. Therefore, the present invention can be applied to evaluation of images in quality.

As described above, a specular gloss simulating device according to the present invention for simulating specular gloss by measuring, in a given geometry, luminance of a sample that has a base material and a colorant material layer formed on the base material, and then simulating a specular reflection light amount in an other geometry from the thus measured luminance, is arranged to include: a lower layer reflection light component creating section for calculating a lower layer reflection light component from base material luminance, where the base material luminance is luminance of only the base material measured in a plurality of geometries, and the lower layer reflection light component is a component being reflected on the base material and transmitting through and out of the colorant material layer; an internal reflection light component creating section for measuring luminance of the sample in the given geometry, and for creating an internal reflection light component from the measured luminance and the lower layer reflection light component, where the internal reflection light component is a component being reflected from an interior of the colorant material layer; a surface reflection light component creating section for measuring luminance of the sample in the given geometry, and for creating a surface reflection light component from the measured luminance, the lower layer reflection light component, and the internal reflection light component, where the surface reflection light component is a component being reflected on a surface of the colorant material layer; and a specular reflection light amount calculating section for obtaining a specular reflection light amount of the sample from the components thus created by the lower layer reflection light component creating section, internal reflection light component creating section, and surface reflection light component creating section.

With the above arrangement, the simulation of the specular gloss is carried out by obtaining the specular reflection light amount of the sample by more effectively using the Bidirectional Reflectance Distribution Function model, taking the lower layer reflection light component and the internal reflection light component, as well as the surface reflection light component, into consideration. This makes it possible to calculate out the specular gloss with high accuracy for low-density image sample and low-gloss image sample for which accurate calculation of the specular gloss cannot be done with the conventional art.

The specular gloss simulating device according to the present invention is preferably arranged such that: the lower layer reflection light component creating section measures the base material luminance in the plurality of geometries, and calculates out the lower layer reflection light component from the thus measured luminance; the internal reflection light component creating section measures the luminance of the sample in a non-specular reflection geometry, calculates out the internal reflection light component from the thus measured luminance and the lower layer reflection light component, and simulates an internal reflection light component in the other geometry by using a Bidirectional Reflectance Distribution Function model; and the surface reflection light component creating section measures the luminance of the sample in a specular reflection geometry, calculates out the surface reflection light component from the thus measured luminance, the lower layer reflection light component, and the internal reflection light component, and simulates the surface reflection light component in an other specular reflection geometry than the geometry by using a Bidirectional Reflectance Distribution Function model.

The specular gloss simulation device of the present invention is used for simulating, by using the Bidirectional Reflectance Distribution Function model, a specular reflection light amount of a sample in each geometry, the sample having, as a sample image, the colorant material layer on the base material, where the base material may be paper, an OHP film or the like, and the colorant material layer contains toner, pigment ink, dye ink or the like. From the thus simulated specular reflection light amount, the specular gloss component of the sample is simulated in the method according to the present invention.

In the specular gloss simulating device, not only the surface reflection light component reflected on the surface of the colorant material layer, but also the internal reflection light component reflected from the interior of the colorant material layer and the lower layer reflection light component reflected on the base material are taken into consideration. So, the specular reflection light amount of the sample is calculated from the surface reflection light component, the internal reflection light component, and the lower layer reflection light component thus calculated out.

Here, the "geometry" is a positional relationship of a light source, image sample, and a photoreceptor in the measurement of the reflection light amount from the image sample to evaluate the specular gloss or the like. More specifically, what is meant by the term "geometry" is the incident light angle 1 and the reflection light angle 2.

Here, the term "incident light angle" is an angle between (a) a light beam from the light source and being incident on the sample, and (b) a normal vector of a plane of the sample at a point at which the light beam is incident on the plane of the sample. The "reflection light angle" is an angle between a light beam reflected on the plane of the sample and the normal vector. Therefore, a "given geometry" has a predetermined incident light angle 1 and a predetermined reflection light angle 2.

Moreover, Among given geometries, the "specular reflection geometry" is a geometry whose incident light angle and the reflection light angle are for the specular reflection of the incident light on the sample. The incident light angle 1 and the reflection light angle 2 (illustrated in FIG. 2) of this geometry are identical with each other.

Moreover, Among given geometries, the "non-specular reflection geometry" is any geometry other than the specular reflection geometry.

In the present invention, it is possible to select any "specular reflection geometry" and "non-specular reflection geometry" which satisfy the above conditions. In the embodiments, the non-specular reflection geometry in which the light source incident light angle qi=45° and the reflection light angle qr=−60° (see FIG. 5) is selected, while the specular reflection geometry in which the light source incident light angle qi=45° and the reflection light angle qr=45° (see FIG. 5) is selected.

The "plurality of geometries" for use in the measurement of the luminance of the base material only for the calculation of the lower layer reflection light component are geometries varied in the light source incident light angle and the reflection light angle by a constant angle. The "plurality of geometries" are so varied that all positional relationships possible under measurement environment are included. A specific example of the "plurality of geometries" is the "each geometry" used in the embodiments in which the geometries are varied in the light source incident light angle and the reflection light angle by angular resolution of 1°.

In the present specification, the term "each geometry (or all geometry)" may encompass any geometry possible under the measurement environment literally. However, in the present Specification, this terms "each geometry (or all geometry)" is also used to mean the "geometries varied in the light source incident light angle and the reflection light angle by a constant angle". A specific example of the "each geometry (or all geometry)" is the geometries varied in the light source incident light angle and the reflection light angle by angular resolution of 1° to include all the positional relationships possible under the measurement environment. Further, the term "each specular reflection geometry" is geometries among the "each geometry (or all geometry)", especially.

In this arrangement, the internal reflection light component and the surface reflection light component of each geometry are not actually measured for the calculation of the specular reflection light amount of the sample. The reflection light component (i.e., lower layer reflection light component) from only the lower layer portion (that is, the base material), which can be actually measured is measured in the plurality of geometries (i.e., each geometry) varied in the light source incident light angle and the reflection light angle at the constant angle. From the thus measured lower layer reflection light component, the specular reflection light amount of the sample can be calculated with high accuracy with this arrangement. Further, with this arrangement, the simulation of the specular gloss is carried out by obtaining the specular reflection light amount of the sample by more effectively using the Bidirectional Reflectance Distribution Function model, taking the lower layer reflection light component and the internal reflection light component, as well as the surface reflection light component, into consideration. This makes it possible to calculate out the specular gloss with high accuracy for low-density image sample and low-gloss image sample for which accurate calculation of the specular gloss cannot be done with the conventional art.

The specular gloss simulating device may be preferably arranged such that the Bidirectional Reflectance Distribution Function model used by the surface reflection light component creating section for simulating the surface reflection light component in the other specular reflection geometry is a Torrance-Sparrow model.

The Torrance-Sparrow model is on assumption that the light is scattered anisotropically. With this arrangement, the use of Torrance-Sparrow model allows accurate simulation of the surface reflection light component in each specular reflection geometry from the measurement result obtained in one predetermined specular reflection geometry. Moreover, the Torrance-Sparrow model is easy to use because it required a small number of parameters.

The specular gloss simulating device according to the present invention may be preferably arranged such that the Bidirectional Reflectance Distribution Function model used by the internal reflection light component creating section for simulating the internal reflection light component in the other geometry is an Oren-Nayar model.

The Oren-Nayar model is on assumption that the light is scattered anisotropically. With this arrangement, the use of Oren-Nayar model allows accurate simulation of the internal reflection light component in each geometry from the measurement result obtained in one predetermined non-specular reflection geometry. Moreover, the Oren-Nayar model is easy to use because it required a small number of parameters.

The specular gloss simulating device according to the present invention may be preferably arranged such that the lower layer reflection light component creating section calculates out the lower layer reflection light component from the measured luminance of the base material, and transmittance and refractive index of the colorant material layer.

This arrangement makes it possible to accurately reproduce the incident light angle and light amount of the light reaching the base material portion of the sample, the reflection light amount of the light reflected from the base material portion with attenuation due to refraction. Therefore, it becomes possible to calculate out the reflection light component from the lower layer portion with higher accuracy.

The specular gloss simulating device may be arranged such that the internal reflection light component creating section also functions as a diffuse reflection light component creating section for simulating diffuse reflection light component which is a component being diffused among colorant material particles contained in the colorant material layer and transmitting out of the colorant material layer; the internal reflection light component creating section comprises: a colorant material particle reflection light component creating section (a) for measuring luminance of the sample in the specular reflection geometry, (b) for calculating out a colorant material particle reflection light component from the thus measured luminance, the lower layer reflection light component, and the diffuse reflection light component, and (c) for simulating a colorant material particle reflection light component in the other geometry by using the Bidirectional Reflectance Distribution Function model, where the colorant material particle reflection light component is a component reflected from the colorant material particles; and a shape parameter calculating section for deciding a mixing ratio between the colorant material particle reflection light component and the surface reflection light component from the results of the calculations performed by the surface reflection light component creating section and the colorant material particle reflection light component creating section, and the thus measured luminance of the sample in the specular reflection geometry, and the specular reflection light amount calculating section obtains the specular reflection light amount by adding up the components thus created respectively by the lower layer reflection light component creating section, diffuse reflection light component creating section, and the components which are created respectively by the colorant material particle reflection light component creating section and the surface reflection light component creating section and whose mixing ratio is decided by the shape parameter calculating section.

With this arrangement, it is possible to accurately simulate specular gloss of a sample having a colorant material layer containing colorant material particles relatively large in diameter (that is, in case where the colorant material particles are pigment). Moreover, with this arrangement, it is possible to simulate, with sufficient accuracy, the specular gloss of the sample in a geometry having a large zenith angle which glossiness becomes higher for a low-gloss image and the simulation accuracy cannot be sufficient even if the lower layer reflection light component and internal reflection light component are taken in consideration.

The specular gloss simulating device may be preferably arranged such that the surface reflection light component creating section uses a Torrance-Sparrow model as the Bidirectional Reflectance Distribution Function, and uses, in the Torrance-Sparrow model, a variable of surface roughness of the sample as a parameter for defining an extent of a reflection light component.

Here, what is meant by the "variable of the roughness of the surface shape of the sample" is a standard deviation (distribution range) of slopes of facets, the standard deviation being calculated with a range of 2 s (about 95.5% of data) from information of height of top surfaces (a boundary between the surface of the colorant material layer and the air layer) of the sample where the information of the height of the top surfaces is the length along the Z axis when the sample is positioned in a XYZ coordinate space (see FIG. 5).

With this arrangement, the use of Torrance-Sparrow model which is on assumption that the light is scattered anisotropically allows highly-accurate calculation of the surface reflection light component. Moreover, the Torrance-Sparrow model is easy to use because it requires a small number of other parameters. Further, if the variable in the roughness of the surface shape of the sample is used as the parameter for defining the extent of the reflection light component, the Torrance-Sparrow model can be used with high accuracy.

The specular gloss simulating device may be preferably arranged such that the colorant material particle reflection light component creating section uses a Torrance-Sparrow model as the Bidirectional Reflectance Distribution Function, and uses, in the Torrance-Sparrow model, a variable of density distribution evenness of the sample as a parameter for defining an extent of a reflection light component.

Here, the "variable of density distribution evenness" is a standard deviation (distribution range) of transmission density calculated with a range of 2 s (about 95.5% of data) from the histogram of the density of each pixel of transmission image of the sample (the transmission image is an image taken, in the space the sample is positioned in a XYZ coordinate space (see FIG. 5), for example, where a camera (light receiver) is positioned on the positive side of the Z axis and the light source is positioned on the negative side of the Z axis)

With this arrangement, the use of Torrance-Sparrow model which is on assumption that the light is anisotropically scattered allows highly-accurate calculation of the colorant material particle reflection light component. Moreover, the Torrance-Sparrow model is easy to use because it requires a small number of other parameters. Further, if the variable of the evenness in density of the sample as the parameter for defining the extent of the reflection light component, the Torrance-Sparrow model can be used with high accuracy.

As described above, another specular gloss simulating device according to the present invention for simulating specular gloss by measuring, in a given geometry, luminance of a sample that has a base material and a colorant material layer which is formed on the base material and contains colorant material particles, and then simulating a specular reflection light amount in an other geometry from the thus measured luminance, is arranged to include: a lower layer reflection light component creating section for calculating lower layer reflection light components in the given geometry and the other geometry from base material luminance, where the base material luminance is luminance of only the base material measured in a plurality of geometries, and the lower layer reflection light component is a component being reflected on the base material and transmitting through and out of the colorant material layer; an upper layer reflection light component creating section for calculating a diffuse reflection light component, a colorant material particle reflection light component, and a surface reflection light component in the other geometry from the luminance of the sample measured in the given geometry and the lower layer reflection light component in the given geometry, the lower layer reflection light component being calculated out by the lower layer reflection light component creating section, where the diffuse reflection light component is a component being diffused among the colorant material particles contained in the colorant material layer and transmitting out of the colorant material layer, the colorant material particle reflection light component is a component being reflected on the colorant material particles, and the surface reflection light component is a component being reflected on a surface of the colorant material layer; and a specular reflection light amount calculating section for calculating out a specular reflection light amount of the sample in the other geometry from the components in the other geometry which are thus calculated out by the lower layer reflection light component creating section and the upper layer reflection light component creating section. With the above arrangement, the simulation of the specular gloss is carried out by obtaining the specular reflection light amount of the sample by effectively using the Bidirectional Reflectance Distribution Function model, taking the lower layer reflection light component and the internal reflection light component, as well as the surface reflection light component, into consideration. This makes it possible to calculate out the specular gloss with high accuracy for low-density image sample and low-gloss image sample for which accurate calculation of the specular gloss cannot be done with the conventional art.

The another specular gloss simulating device according to the present invention may be preferable arranged such that the upper reflection light component creating section calculates out the diffuse reflection light component, the colorant material particle reflection light component, and the surface reflection light component in the other geometry by using a Bidirectional Reflectance Distribution Function model.

The use of the Bidirectional Reflectance Distribution Function model makes it possible for the upper layer reflection light component creating section to obtain the diffuse reflection light component, colorant material particle reflection light component, and surface reflection light component with accuracy, and consequently makes it possible to evaluate the specular glossiness with high accuracy.

The another specular gloss simulating device may be preferably arranged such that the lower layer reflection light component creating section calculates out the lower layer reflection light components in the other geometry and at least three kinds of the given geometries; the upper layer reflection light component creating section includes: a parameter calculating section for deciding (a) a parameter to be used in the Oren-Nayar model, and (b) a mixing ratio among the diffuse reflection light component, the colorant material particle reflection light component, and the surface reflection light component, from (i) luminance of the sample measured in the at least three kinds of the given geometries, and (ii) the lower layer reflection light components in the at least three kinds of the given geometries, the lower layer reflection light components being calculated by the lower layer reflections light component creating section; and a reflection light component calculating section for calculating the colorant material particle reflection light component and the surface reflection light component in the other geometry according to the mixing ratio, and calculating the diffuse reflection light component in the other geometry according to the mixing ratio and from the parameter by using the Oren-Nayar model.

The mixing ratio among the diffuse reflection light component, colorant material particle reflection light component, and surface reflection light component, which are contained in the reflection light component can be expressed with two parameter where the entire reflection light component is put as 1. Moreover, for calculating out the diffuse reflection light component by using the Oren-Nayar model, it is necessary to find an unknown parameter that describes a reflection ratio of the facet.

In this arrangement, for obtaining the reflection light components of the upper layer reflection light, the parameter calculating section uses the density of the sample measured in the at least three given geometries, and the lower layer reflection light components in the at least three given geometries. The upper layer reflection light component is obtained by subtracting the lower layer reflection light component from the specular reflection light component from the lower layer reflection light component. Therefore, three conditional equations as to the at least three given geometries can be created. With the three conditional equations, the unknown parameter in the Oren-Nayar model and two parameter that describes the mixing ratio. That is, it is possible to obtain, without approximation, the components contained in the upper reflection light component. Therefore, it is possible to accurately obtain the diffuse reflection light component, colorant material particle reflection light component, and surface reflection light component contained in the upper layer reflection light component, and consequently, it is possible to evaluate the specular glossiness with high accuracy.

The another specular gloss simulating device according to the present invention may be preferably arranged such that the reflection light component calculating section calculates the colorant material particle reflection light component and the surface reflection light component in the other geometry according to the mixing ratio and by using the Torrance-Sparrow model.

The use of the Torrance-Sparrow model makes it possible to accurately obtain the colorant material particles reflection light component and the surface reflection light component contained in the upper layer reflection light component. Consequently, it becomes possible to evaluate the specular gloss with high accuracy.

The any of the (another) specular gloss simulating device may be controlled by a computer. Thus, the scope of the present invention encompasses a computer-readable recording medium in which a control program is stored, the control program being for operating the (another) specular gloss simulating device and the control program causing a computer to function as each of the sections.

With the control program according to the present invention the control function of the specular gloss simulating device having any of these arrangement can be realized with a computer. Moreover, the recording medium according to the present invention is a recording medium in which the control program is stored. As a result, it is possible to provide the portable recording medium storing the control program for carrying out the specular simulation method of the present invention.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A specular gloss simulation device for simulating specular gloss by measuring, in a given geometry, luminance of a sample that has a base material and a colorant material layer formed on the base material, and then simulating a specular reflection light amount in an other geometry from the thus measured luminance, the specular gloss simulation device comprising:

a lower layer reflection light component creating section for calculating a lower layer reflection light component from base material luminance, where the base material luminance is luminance of only the base material measured in a plurality of geometries, and the lower layer reflection light component is a component being reflected on the base material and transmitting through and out of the colorant material layer;

an internal reflection light component creating section for measuring luminance of the sample in the given geometry, and for creating an internal reflection light component from the measured luminance and the lower layer reflection light component, where the internal reflection light component is a component being reflected from an interior of the colorant material layer;

a surface reflection light component creating section for measuring luminance of the sample in the given geometry, and for creating a surface reflection light component from the measured luminance, the lower layer reflection light component, and the internal reflection light component, where the surface reflection light component is a component being reflected on a surface of the colorant material layer; and a specular reflection light amount calculating section for obtaining a specular reflection light amount of the sample from the components thus created by the lower layer reflection light component creating section, internal reflection light component creating section, and surface reflection light component creating section.

2. A specular gloss simulation device as set forth in claim 1, wherein:

the lower layer reflection light component creating section measures the base material luminance in the plurality of geometries, and calculates out the lower layer reflection light component from the thus measured luminance;

the internal reflection light component creating section measures the luminance of the sample in a non-specular reflection geometry, calculates out the internal reflection light component from the thus measured luminance and the lower layer reflection light component, and simulates an internal reflection light component in the other geometry by using a Bidirectional Reflectance Distribution Function model; and the surface reflection light component creating section measures the luminance of the sample in a specular reflection geometry, calculates out the surface reflection light component from the thus measured luminance, the lower layer reflection light component, and the internal reflection light component, and simulates the surface reflection light component in an other specular reflection geometry than the geometry by using a Bidirectional Reflectance Distribution Function model.

3. A specular gloss simulation device as set forth in claim 2, wherein:

the Bidirectional Reflectance Distribution Function model used by the surface reflection light component creating section for simulating the surface reflection light component in the other geometry is a Torrance-Sparrow model.

4. A specular gloss simulation device as set forth in claim 2, wherein:
the Bidirectional Reflectance Distribution Function model used by the internal reflection light component creating section for simulating the internal reflection light component in the other geometry is an Oren-Nayar model.

5. A specular gloss simulation device as set forth in claim 2, wherein:
the lower layer reflection light component creating section calculates out the lower layer reflection light component from the measured luminance of the base material, and transmittance and refractive index of the colorant material layer.

6. A specular gloss simulation device as set forth in claim 2, wherein:
the internal reflection light component creating section also functions as a diffuse reflection light component creating section for simulating diffuse reflection light component which is a component being diffused among colorant material particles contained in the colorant material layer and transmitting out of the colorant material layer;
the internal reflection light component creating section comprises:
a colorant material particle reflection light component creating section (a) for measuring luminance of the sample in the specular reflection geometry, (b) for calculating out a colorant material particle reflection light component from the thus measured luminance, the lower layer reflection light component, and the diffuse reflection light component, and (c) for simulating a colorant material particle reflection light component in the other geometry by using the Bidirectional Reflectance Distribution Function model, where the colorant material particle reflection light component is a component reflected from the colorant material particles; and
a shape parameter calculating section for deciding a mixing ratio between the colorant material particle reflection light component and the surface reflection light component from the results of the calculations performed by the surface reflection light component creating section and the colorant material particle reflection light component creating section, and the thus measured luminance of the sample in the specular reflection geometry, and
the specular reflection light amount calculating section obtains the specular reflection light amount by adding up the components thus created respectively by the lower layer reflection light component creating section, diffuse reflection light component creating section, and the components which are created respectively by the colorant material particle reflection light component creating section and the surface reflection light component creating section and whose mixing ratio is decided by the shape parameter calculating section.

7. A specular gloss simulation device as set forth in claim 6, wherein:
the surface reflection light component creating section uses a Torrance-Sparrow model as the Bidirectional Reflectance Distribution Function, and uses, in the Torrance-Sparrow model, a variable of surface roughness of the sample as a parameter for defining an extent of a reflection light component.

8. A specular gloss simulation device as set forth in claim 6, wherein:
the colorant material particle reflection light component creating section uses a Torrance-Sparrow model as the Bidirectional Reflectance Distribution Function, and uses, in the Torrance-Sparrow model, a variable of density distribution evenness of the sample as a parameter for defining an extent of a reflection light component.

9. A specular gloss simulation device for simulating specular gloss by measuring, in a given geometry, luminance of a sample that has a base material and a colorant material layer formed on the base material, and then simulating a specular reflection light amount in an other geometry from the thus measured luminance, the specular gloss simulation device comprising:
a lower layer reflection light component creating section for calculating a lower layer reflection light component from base material luminance, where the base material luminance is luminance of only the base material measured in a plurality of geometries, and the lower layer reflection light component is a component being reflected on the base material and transmitting through and out of the colorant material layer;
an internal reflection light component creating section for creating an internal reflection light component from luminance of the sample and the lower layer reflection light component, where the internal reflection light component is a component being reflected from an interior of the colorant material layer, and the luminance of the sample is measured in the given geometry;
a surface reflection light component creating section for creating a surface reflection light component from the luminance of the sample, the lower layer reflection light component, and the internal reflection light component, where the surface reflection light component is a component being reflected on a surface of the colorant material layer, and the luminance of the sample is measured in the given geometry; and
a specular reflection light amount calculating section for obtaining a specular reflection light amount of the sample from the components thus created by the lower layer reflection light component creating section, internal reflection light component creating section, and surface reflection light component creating section.

10. A specular gloss simulation device for simulating specular gloss by measuring, in a given geometry, luminance of a sample that has a base material and a colorant material layer which is formed on the base material and contains colorant material particles, and then simulating a specular reflection light amount in an other geometry from the thus measured luminance, the specular gloss simulation device comprising:
a lower layer reflection light component creating section for calculating lower layer reflection light components in the given geometry and the other geometry from base material luminance, where the base material luminance is luminance of only the base material measured in a plurality of geometries, and the lower layer reflection light component is a component being reflected on the base material and transmitting through and out of the colorant material layer;
an upper layer reflection light component creating section for calculating a diffuse reflection light component, a colorant material particle reflection light component, and a surface reflection light component in the other geometry from the luminance of the sample measured in the given geometry and the lower layer reflection light component in the given geometry, the lower layer reflection light component being calculated out by the lower layer reflection light component creating section, where the diffuse reflection light component is a component being diffused among the colorant material particles contained in the colorant material layer and transmitting out of the colorant material layer, the colorant material particle reflection light component is a component being reflected on the colorant material particles, and the surface reflection light component is a component being reflected on a surface of the colorant material layer; and a specular reflection light amount calculating section for calculating out a specular reflection light amount of the sample in the other geometry from the components in the other geometry which are thus calculated out by the lower layer reflection light component creating section and the upper layer reflection light component creating section.

11. A specular gloss simulation device as set forth in claim 10, wherein:

the upper reflection light component creating section calculates out the diffuse reflection light component, the colorant material particle reflection light component, and the surface reflection light component in the other geometry by using a Bidirectional Reflectance Distribution Function model.

12. A specular gloss simulation device as set forth in claim 11, wherein:

the lower layer reflection light component creating section calculates out the lower layer reflection light components in the other geometry and at least three kinds of the given geometries;

the upper layer reflection light component creating section includes:

a parameter calculating section for deciding (a) a parameter to be used in the Oren-Nayar model, and (b) a mixing ratio among the diffuse reflection light component, the colorant material particle reflection light component, and the surface reflection light component, from (i) luminance of the sample measured in the at least three kinds of the given geometries, and (ii) the lower layer reflection light components in the at least three kinds of the given geometries, the lower layer reflection light components being calculated by the lower layer reflection light component creating section; and a reflection light component calculating section for calculating the colorant material particle reflection light component and the surface reflection light component in the other geometry according to the mixing ratio, and calculating the diffuse reflection light component in the other geometry according to the mixing ratio and from the parameter by using the Oren-Nayar model.

13. A specular gloss simulation device as set forth in claim 12, wherein:

the reflection light component calculating section calculates the colorant material particle reflection light component and the surface reflection light component in the other geometry according to the mixing ratio and by using the Torrance-Sparrow model.

14. A specular gloss simulation method for simulating specular gloss by simulating a specular reflection light amount of a sample having a base material and a colorant material layer formed on the base material, the method comprising:

(i) creating a lower layer reflection light component by calculating out the lower layer reflection light component from base material luminance where the base material luminance is luminance of only the base material measured in a plurality of geometries which are varied in incident light angle and reflection light angle by a constant angle, the lower layer reflection light component is a component being reflected on the base material and transmitting through and out of the colorant material layer;

(ii) creating an internal refection light component by simulating, by using a Bidirectional Reflectance Distribution Function model, the internal refection light component in the other geometry from an internal reflection light component calculated out from luminance of the sample measured in one non-specular reflection geometry and the lower layer reflection light component, where the internal reflection light component is a component being reflected from an interior of the colorant material layer;

(iii) creating a surface reflection light component by simulating, by using a Bidirectional Reflectance Distribution Function model, the surface reflection light component in the other geometry from a surface reflection light component calculated out from luminance of the sample measured in one non-specular reflection geometry, the lower layer reflection light component, and the internal reflection light component, where the surface reflection light component is a component being reflected on a surface of the colorant material layer; and (iv) calculating out a specular reflection light amount of the sample from the lower layer reflection light component, internal reflection light component, and surface reflection light component thus obtained.

15. A specular gloss simulation method for simulating specular gloss by simulating a specular reflection light amount of a sample having a base material and a colorant material layer which is formed on the base material and contains colorant material particles, the method comprising:

(i) creating lower layer reflection light components in the given geometry and the other geometry by calculating out the lower layer reflection light components from base material luminance where the base material luminance is luminance of only the base material measured in a plurality of geometries, the lower layer reflection light component is a component being reflected on the base material and transmitting through and out of the colorant material layer;

(ii) calculating out a diffuse reflection light component, a colorant material particle reflection light component, and a surface reflection light component from the luminance of the sample measured in the given geometry and the lower layer reflection light component in the given geometry, the lower layer reflection light component being calculated out in the step (i), where the diffuse reflection light component is a component being diffused among the colorant material particles contained in the colorant material layer and transmitting out of the colorant material layer, the colorant material particle reflection light component is a component being reflected on the colorant material particles, and the surface reflection light component is a component being reflected on a surface of the colorant material layer; and (iii) calculating out a specular reflection light amount of the sample in the other geometry from the diffuse reflection light component, the lower layer reflection light component in the other geometry, which is thus calculated in the step (i) and the colorant material particle reflection light component, and the surface reflection light component thus calculated in the step (ii).

16. A computer-readable storage medium in which a control program is stored, the control program being for operating a specular gloss simulation device for simulating specular gloss by measuring, in a given geometry, luminance of a sample having a base material and a colorant material layer formed on the base material, and then simulating a specular reflection light amount in an other geometry from the thus measured luminance, the specular gloss simulation device comprising:

a lower layer reflection light component creating section for calculating a lower layer reflection light component from base material luminance, where the base material luminance is luminance of only the base material measured in a plurality of geometries, and the lower layer reflection light component is a component being reflected on the base material and transmitting through and out of the colorant material layer;

an internal reflection light component creating section for measuring luminance of the sample in the given geometry, and for creating an internal reflection light component from the measured luminance and the lower layer reflection light component, where the internal reflection light component is a component being reflected from an interior of the colorant material layer;

a surface reflection light component creating section for measuring luminance of the sample in the given geometry, and for creating a surface reflection light component from the measured luminance, the lower layer reflection light component, and the internal reflection light component, where the surface reflection light component is a component being reflected on a surface of the colorant material layer; and a specular reflection light amount calculating section for obtaining a specular reflection light amount of the sample from the components thus created by the lower layer reflection light component creating section, internal reflection light component creating section, and surface reflection light component creating section, and the control program causing a computer to function as each of the sections.

17. A computer-readable storage medium in which a control program is stored, the control program being for operating a specular gloss simulation device for simulating specular gloss by measuring, in a given geometry, luminance of a sample having a base material and a colorant material layer formed on the base material, and then simulating a specular reflection light amount in an other geometry from the thus measured luminance, the specular gloss simulation device comprising:

a lower layer reflection light component creating section for calculating a lower layer reflection light component from base material luminance, where the base material luminance is luminance of only the base material measured in a plurality of geometries, and the lower layer reflection light component is a component being reflected on the base material and transmitting through and out of the colorant material layer;

an internal reflection light component creating section for creating an internal reflection light component from luminance of the sample and the lower layer reflection light component, where the internal reflection light component is a component being reflected from an interior of the colorant material layer, and the luminance of the sample is measured in the given geometry;

a surface reflection light component creating section for creating a surface reflection light component from the luminance of the sample, the lower layer reflection light component, and the internal reflection light component, where the surface reflection light component is a component being reflected on a surface of the colorant material layer, and the luminance of the sample is measured in the given geometry; and a specular reflection light amount calculating section for obtaining a specular reflection light amount of the sample from the components thus created by the lower layer reflection light component creating section, internal reflection light component creating section, and surface reflection light component creating section, and the control program causing a computer to function as each of the sections.

18. A computer-readable storage medium in which a control program is stored, the control program being for operating a specular gloss simulation device for simulating specular gloss by measuring, in a given geometry, luminance of a sample having a base material and a colorant material layer which is formed on the base material and contains colorant material particles, and then simulating a specular reflection light amount in an other geometry from the thus measured luminance, the specular gloss simulation device comprising:

a lower layer reflection light component creating section for calculating lower layer reflection light components in the given geometry and the other geometry from base material luminance, where the base material luminance is luminance of only the base material measured in a plurality of geometries, and the lower layer reflection light component is a component being reflected on the base material and transmitting through and out of the colorant material layer;

an upper layer reflection light component creating section for calculating a diffuse reflection light component, a colorant material particle reflection light component, and a surface reflection light component in the other geometry from the luminance of the sample measured in the given geometry and the lower layer reflection light component in the given geometry, the lower layer reflection light component being calculated out by the lower layer reflection light component creating section, where the diffuse reflection light component is a component being diffused among the colorant material particles contained in the colorant material layer and transmitting out of the colorant material layer, the colorant material particle reflection light component is a component being reflected on the colorant material particles, and the surface reflection light component is a component being reflected on a surface of the colorant material layer; and a specular reflection light amount calculating section for calculating out a specular reflection light amount of the sample in the other geometry from the components in the other geometry which are thus calculated out by the lower layer reflection light component creating section and the upper layer reflection light component creating section, and the control program causing a computer to function as each of the sections.

* * * * *